US007759134B2

(12) United States Patent
Chin et al.

(10) Patent No.: US 7,759,134 B2
(45) Date of Patent: Jul. 20, 2010

(54) MAGNETOSTRICTIVE LIGAND SENSOR

(75) Inventors: Bryan A. Chin, Auburn, AL (US);
Zhongyang Cheng, Auburn, AL (US);
Vitaly J. Vodyanoy, Auburn, AL (US);
James Barbaree, Dadeville, AL (US);
Valery A. Petrenko, Auburn, AL (US);
Tung-Shi Huang, Auburn, AL (US);
Howard C. Wikle, III, Auburn, AL (US)

(73) Assignee: Auburn University, Auburn, AL (US)

( * ) Notice: Subject to any disclaimer, the term of this patent is extended or adjusted under 35 U.S.C. 154(b) by 538 days.

(21) Appl. No.: 10/923,414

(22) Filed: Aug. 20, 2004

(65) Prior Publication Data
US 2005/0074904 A1 Apr. 7, 2005

Related U.S. Application Data

(60) Provisional application No. 60/501,953, filed on Sep. 11, 2003.

(51) Int. Cl.
*G01N 33/553* (2006.01)

(52) U.S. Cl. ............... 436/525; 436/518; 436/524; 422/50; 422/68.1; 422/82.01; 422/82.02; 435/283.1; 435/287.1

(58) Field of Classification Search ............... 436/518, 436/524, 525; 422/50, 68.1, 82.01, 82.02; 435/283.1, 287.1
See application file for complete search history.

(56) References Cited

U.S. PATENT DOCUMENTS

| 4,265,855 | A | * | 5/1981 | Mandle et al. | 422/65 |
| 5,023,452 | A | * | 6/1991 | Purcell et al. | 850/15 |
| 5,043,693 | A | | 8/1991 | Edelstein | |
| 5,406,153 | A | * | 4/1995 | Flatau et al. | 310/26 |
| 5,671,155 | A | * | 9/1997 | Edens et al. | 702/38 |
| 5,773,156 | A | | 6/1998 | Inomata et al. | |
| 5,821,129 | A | | 10/1998 | Grimes et al. | |
| 5,981,297 | A | | 11/1999 | Baselt | |
| 5,998,995 | A | | 12/1999 | Osiander et al. | |
| 6,093,337 | A | | 7/2000 | McCallum et al. | |
| 6,273,965 | B1 | | 8/2001 | Pulvirenti et al. | |
| 6,352,649 | B1 | | 3/2002 | McCallum et al. | |
| 6,359,444 | B1 | | 3/2002 | Grimes | |
| 6,393,921 | B1 | | 5/2002 | Grimes et al. | |
| 6,397,661 | B1 | | 6/2002 | Grimes et al. | |
| 6,470,760 | B2 | * | 10/2002 | Shinozaki et al. | 73/863.33 |

(Continued)

FOREIGN PATENT DOCUMENTS

| EP | 0 453 228 A2 | 10/1991 |
| GB | 2 383 846 A | 7/2003 |
| WO | WO 95/06248 | 3/1995 |

OTHER PUBLICATIONS

Anjanappa, M. and Y. Wu, "Magnetostrictive Particulate Actuators: Configuration, Modeling and Characterization," *Smart Mater. Struct.*, 1997, pp. 393-402, vol. 6.

(Continued)

*Primary Examiner*—Melanie J. Yu
(74) *Attorney, Agent, or Firm*—Andrus, Sceales, Starke & Sawall, LLP

(57) ABSTRACT

A magnetostrictive ligand sensor device (MLSD), system and method are provided having at least one magnetostrictive particle (MSP) to which is bound at least one binding element. The MSP may be dispersed in a sample containing a target ligand such that the target ligand binds thereto. A driver is also provided to emit a varying magnetic field such that the MSP produces a resonance response detectable by a measurement device configured to receive and detect changes in the resonance response that are due to alterations of the binding element. The MLSD and assays find use in identifying and quantitating ligands as well as chemicals and environmental conditions in a sample or patient.

23 Claims, 30 Drawing Sheets

U.S. PATENT DOCUMENTS

| | | | |
|---|---|---|---|
| 6,548,311 B1* | 4/2003 | Knoll | 436/524 |
| 6,579,612 B1 | 6/2003 | Lille | |
| 6,649,419 B1* | 11/2003 | Anderson | 436/526 |
| 6,884,351 B1* | 4/2005 | Lytal | 210/601 |
| 7,302,829 B2* | 12/2007 | Zribi | 73/29.01 |
| 7,309,439 B2* | 12/2007 | Fernandez et al. | 210/695 |
| 2002/0137119 A1* | 9/2002 | Katz | 435/23 |
| 2002/0166382 A1* | 11/2002 | Bachas et al. | 73/579 |
| 2004/0126620 A1* | 7/2004 | Viehland et al. | 428/692 |
| 2004/0137607 A1* | 7/2004 | Tanaami et al. | 435/287.2 |

OTHER PUBLICATIONS

Anjanappa, M.A., Y. Wu, "Experimental Study of the Macroscopic Behavior of Magnetostrictive Particulate Actuators," *Proceedings of SPIE—The International Society for Optical Engineering*, 1997, pp. 874-879, vol. 3041.

Barandiaran, J.M., et al., "New Sensors Based on the Magnetoelastic Resonance of Metallic Glasses," *Sensors and Actuators*, 2000, pp. 154-157, vol. 81.

Batt, A.J., et al., "Giant Magnetostriction Behaviour of Melt-Spun Ribbon and Pressed Compacts of $Sm(Fe_{1-x}CO_x)_2$ Alloys," *Sensors and Actuators*, 2000, pp. 170-173, vol. 81.

Cai, Q.Y. and C.A. Grimes, "A Salt-Independent pH Sensor," *Sensors and Actuators B*, 2001, pp. 144-149, vol. 79.

Cai, Q.Y. and G.A. Grimes, "A Salt-Independent pH Sensor," *Sensors and Actuators B 79*, 2001. pp. 144-149.

Cai, Q.Y., et al., "A Wireless, Remote Query Magnetoelastic $CO_2$ Sensor," *J. Environ. Monit.*, 2000, pp. 556-560, vol. 2.

Cai, Q.Y., et al., "A Wireless, Remote Query Magnetoelastic $CO^2$ Sensor," *J. Environ. Monitor.*, 2000, pp. 556-560, vol. 2.

Chiriac, H., et al., "Design and Fabrication of Microminiature Delay Line Using Thin Film Technology," *Sensors and Actuators A*, 1997, pp. 280-284, vol. 59.

Chiriac, H., et al., "Fe-Based Amorphous Thin Film as a Magnetoelastic Sensor Material," *Sensors and Actuators*, 2000, pp. 166-169, vol. 81.

Chiriac, H., et al., "Magneto-Surface-Acoustic-Waves Microdevice Using Thin Film Technology: Design and Fabrication Process," *Sensors and Actuators A*, 2001, pp. 107-111, vol. 91.

Duenas, T., et al., "Micro-Sensor Coupling Magnetostriction and Magnetoresistive Phenomena," *Journal of Magnetism and Magnetic Materials*, 2002, pp. 1132-1135, vol. 242-245.

Duenas, T.A., et al., "Magnetostrictive Composite Material Systems Analytical/Experimental," *Materials Research Society Symposium—Proceedings*, 1997, pp. 527-543, vol. 459.

Feng, X., et al., "Predicting Effective Magnetostriction and Moduli of Magnetoresistive Composites by Using the Double-Inclusion Method," *Mechanics of Materials*, 2003, pp. 623-631, vol. 35.

Frommberger, M., et al., "Processing and Application Of Magnetoelastic Thin Films in High-Frequency Devices," *Microelectronic Engineering*, 2003, pp. 588-594, vols. 67-68.

Germano, R., et al., "Direct Magnetostriction and Magnetoelastic Wave Amplitude to Measure a Linear Displacement," *Sensors and Actuators*, 2000, pp. 134-136, vol. 81.

Grabham, N.J., et al., "Thick-Film Magnetostrictive Material for MEMS," *Electronics Letters*, 2000, pp. 332-334, vol. 36(4).

Greenough, R.D., et al., "The Properties and Applications of Magnetostrictive Rare-Earth Compounds," *Journal of Magnetism and Magnetic Materials*, 1991, pp. 75-80, vol. 101.

Guitérrez, J. and J.M. Barandiarián, "High Magnetostriction Metallic Glasses Used as Magnetoelastic Labels," *IEEE Transactions on Magnetics*, 1995, pp. 3146-3148, vol. 31(6).

Hornreich, R.M., et al., "Magnetostrictive Phenomena in Metallic Materials and Some of Their Device Applications," *IEEE Transactions on Magnetics*, 1971, pp. 29-48, vol. 7(1).

Hristoforou, E., "Magnetostrictive Delay Lines and Their Applications," *Sensors and Actuators*, 1997, pp. 183-191, vol. A 59.

Hristoforou, E., "Magnetostrictive Delay Lines: Engineering Theory and Sensing Applications," *Measurement: Science & Technology*, 2003, pp. R15-R47, vol. 14.

Hristoforou, E., et al., "An Alternative Method for Determining the $\lambda(H)$ Function in Magnetostrictive Amorphous Alloys," 1998, pp. 49-54, vol. A 67.

Hristoforou, E., et al., "Improving the Magnetostrictive Delay Line Resolution," *Sensors and Actuators*, 1997, pp. 84-88, vol. A 59.

Hristoforou, E., et al., "On the Calibration of Position Sensors Based on Magnetic Delay Lines," *Sensors and Actuators*, 1997, pp. 89-93, vol. A 59.

Hristoforou, E., et al., "Thin Film Thickness Sensor Based on a New Magnetostrictive Delay Line Arrangement," *Sensors and Actuators*, 1999, pp. 156-161, vol. 76.

Hudson, J., "Dynamic Magneto-Mechanical Properties of Epoxy-Bonded Terfandol-D Composites," *Sensors and Actuators*, 2000, pp. 294-296, vol. 81.

Ilic, B., et al., "Mechanical Resonant Immunospecific Biological Detector," *Applied Physics Letters*, 2000, pp. 450-452, vol. 77(3).

Ilic, B., et al., "Single Cell Detection with Micromechanical Oscillators," *J. Vac. Sci. Technol.*, 2001, pp. 2825-2828, vol. B 19(6).

Ilic, et al., "Single Cell Detection with Micromechanical Oscillators," *J. Vac. Sci. Technol. B.*, 2001, pp. 2825-2828, vol. 19(b).

Ishiyama, K., et al., "Smart Actuator with Magneto-Elastic Strain Sensor," *Journal of Magnetism and Magnetic Materials*, 2002, pp. 1163-1165, vol. 242-245.

Jain, M.K., et al., "A Wireless Micro-Sensor for Simultaneous Measurement of pH, Temperature, and Pressure," *Smart Mater. Struct.*, 2001, pp. 347-353, vol. 10.

Jain, M.K., et al., "Magneto-Acoustic Sensors for Measurement of Liquid Temperature, Viscosity and Density," *Applied Acoustics*, 2001, pp. 1001-1011, vol. 62.

Kaniusas, E., et al., "Magnetostrictive Amorphous Bilayers and Trilayers for Thermal Sensors," *Journal of Magnetism and Magnetic Materials*, 2003, pp. 624-626, vol. 254-255.

Karagiannis, V., et al., "Position Sensors Based on the Delay Line Principle," *Sensors and Actuators*, 2003 (*Article in Press*) pp. 1-4.

Kim, C.K., "The Relationship Between Microstructure and Magnetoelastic Response in the Magnetostrictive Amorphous Alloy $Co_{47.4}Fe_{31.6}Si_2B_{19}$ After Magnetic Field Annealing," *Materials Science and Engineering*, 1995, pp. 1-6, vol. B34.

Klinger, T., et al., "Magnetostrictive Amorphous Sensor for BioMedical Monitoring," *IEEE Transactions on Magnetics*, 1992, pp. 2400-2402, vol. 28(5).

Kraus, L., et al., "Amorphous CoFeCrSiB Ribbons for Strain Sensing Applications," *Journal of Magnetism and Magnetic Materials*, 2002, pp. 241-243, vol. 242-245.

Ludwig, A., et al., "High-Frequency Magnetoelastic Materials for Remote-Interrogated Stress Sensors," *Journal of Magnetism and Magnetic Materials*, 2002, pp. 1126-1131, vol. 242-245.

Manassis, C., et al., "Optimized Distributed Field Sensor Based on Magnetostrictive Delay Lines," *Sensors and Actuators*, 2003, (*Article in Press*), pp. 1-4.

Mehnen, L., et al., "Displacement Sensor Based on an Amorphous Bilayer Including a Magnetostrictive Component," *Journal of Magnetism and Magnetic Materials*, 2003, pp. 627-629, vol. 254-255.

Mehnen, L., et al., "Magnetostrictive Amorphous Bimetal Sensors," *Journal of Magnetism and Magnetic Materials*, 2000, pp. 779-781, vol. 215-216.

Michelena, M.D., et al., "New Hybrid Magnetometric Sensor," *Sensors and Actuators*, 2002, pp. 153-159, vol. A 100.

Michelena, M.D., et al., "Piezoelectric-Magnetostrictive Magnetic Sensor Using Stripe Actuators," *Journal of Magnetism and Magnetic Materials*, 2002, pp. 1160-1162, vol. 242-245.

Mohle-Eldin, M-E.Y. and L. Gunther, "Anomalous Mössbaur Fraction in Small Magnetic Particles Due to Magnetostriction," *Journal of Magnetism and Magnetic Materials*, 1993, pp. 346-358, vol. 127(3).

Muratsugu, M., et al., "Quartz Crystal Microbalance for the Detection of Microgram Quantities of Human Serum Albumin: Relationship Between the Frequency Change and the Mass of Protein Adsorbed," *Anal. Chem.*, 1993, pp. 2933-2937, vol. 65.

Na, S.M., et al., "Magnetostrictive Properties of Polymer-Bonded Fe-Co Based Alloy Composites," *J. Appl. Physics*, 2003, pp. 8501-8503, vol. 93.

Or, S.W., et al., "Effect of Combined Magnetic Bias and Drive Fields on Dynamic Magnetomechnical Properties of Terfendol-D/epoxy 1-3 Composites," *Journal of Magnetism and Magnetic Materials*, 2003, pp. L-181-L185, vol. 262.

Petrenko, V.A. and V.J. Vodyanoy, "Phage Display for Detection of Biological Threat Agents," *Journal of Microbiological Methods*, 2003, pp. 253-262, vol. 53.

Puckett, L.G., et al., "Monitoring Blood Coagulation with Magnetoelastic Sensors," *Biosensors and Bioelectronics*, 2003, pp. 675-681, vol. 18.

Pulliam, W., et al., "Recent Advances in Magnetostrictive Particulate Composite Technology," *Proceedings of SPIE—The International Society for Optical Engineering*, 2002, pp. 271-281, vol. 4698.

Quandt, E., "Giant Magnetostrictive Thin Film Materials and Applications," *Journal of Alloys and Compounds*, 1997, pp. 126-132, vol. 258.

Ruan, C., et al. "A Wireless pH Sensor Based on the Use of Salt-Independent Micro-Scale Polymer Spheres" *Sensors and Actuators*, 2003, (*Article in Press*), pp. 1-9, vol. Bxxx.

Shieh, J., et al., "The Selection of Sensors," *Progress in Materials Science*, 2001, pp. 461-504, vol. 46.

Smith, C.H., et al., "*Magnetic Biosensors,*" *Sensors Online*, 2003, pp. 1-4.

Stoyanov, P.G., and C.A. Grimes, "A remote query magnetostrictive viscosity sensor," *Sensors and Actuators*, 2000, pp. 8-14, vol. 80.

Thundat, T., et al., "Microcantilever Sensors," *Microscale Thermophysical Engineering*, 1997, pp. 185-199, vol. 1.

Tiercelin, N., et al., "Giant Magnetostriction Thin Films for Multi-Cantilever Micro-Structures Driving," *Sensors and Actuators*, 2000, pp. 162-165, vol. 81.

Vassiliev, A., "Magnetically Driven Shape Memory Alloys," *Journal of Magnetism and Magnetic Materials*, 2002, pp. 66-67, vol. 242-245.

Wang, D., et al., "Homogenization of Magnetostrictive Particle-Filled Elastomers Using an Interface-Enriched Reproducing Kernel Particle Method," *Finite Elements in Analysis and Design*, 2003, pp. 765-782, vol. 39.

Wing Or, S., et al., "Effect of Combined Magnetic Bias and Drive Fields on Dynamic Magnetomechanical Properties of Terfenol-D/Epoxy 1-3 Composites," *Journal of Magnetism and Magnetic Materials*, 2003, pp. L181-L185, vol. 262.

Wu, Y. and M.A. Anjanappa, "Modeling of Embedded Magnetostrictive Particulate Actuators," *Proceedings of SPIE—The International Society for Optical Engineering*, 1996, pp. 517-527, vol. 2717.

Yi, J.W., et al., "In situ Cell Detection Using Piezoelectric Lead Zirconate Titanate-Stainless Steel Cantilevers," *Journal of Applied Physics*, 2003, pp. 619-625, vol. 93(1).

Yi, J.W., et al., "Effect of Length, Width, and Mode on the Mass Detection Sensitivity of Piezoelectric Unimorph Cantilevers," *Journal of Applied Physics*, 2002, pp. 1686-1686, vol. 91(3).

Ruan, C., et al., "A Staphylococcal Enterotoxin B Magnetoelastic Immunosensor," *Biosensors & Bioelectronics*, 2004, p. 585-591, vol. 20.

\* cited by examiner

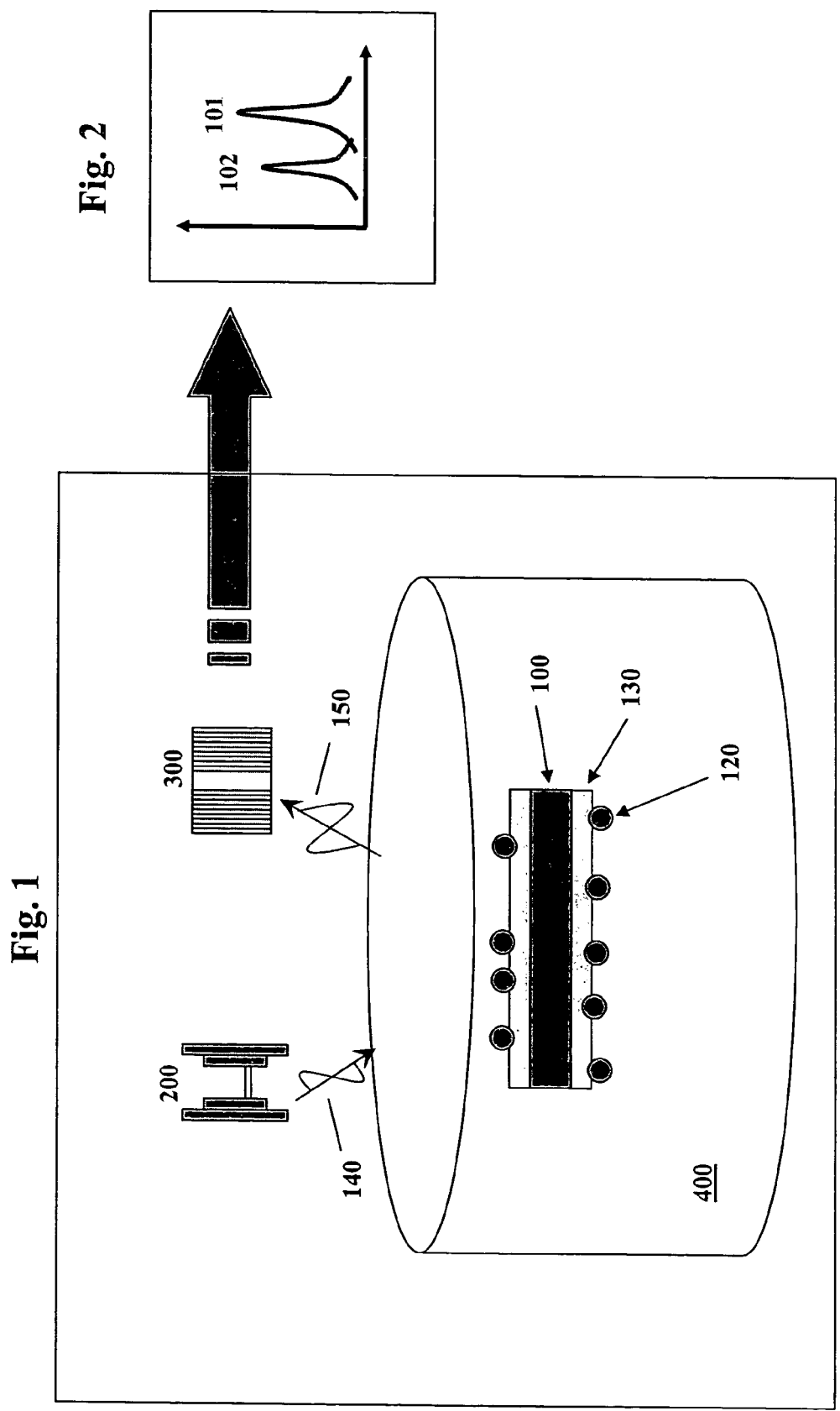

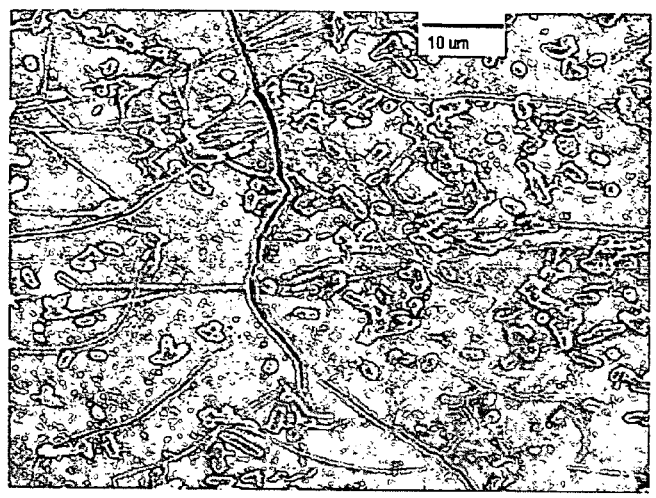
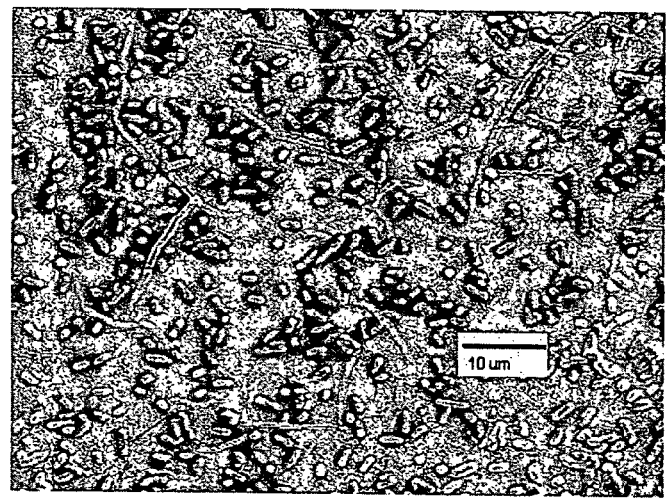
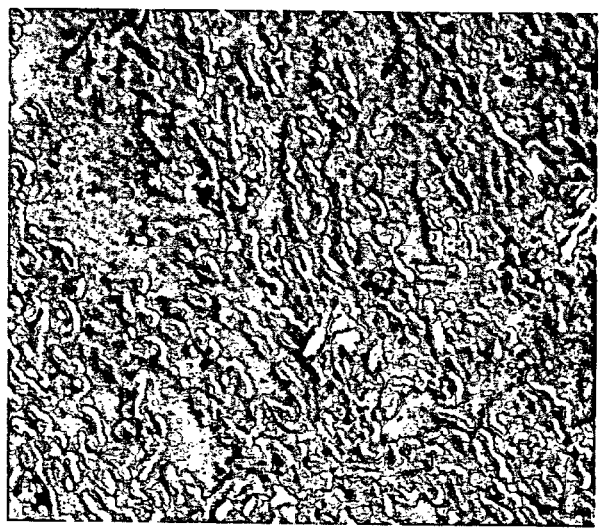
Figure 14

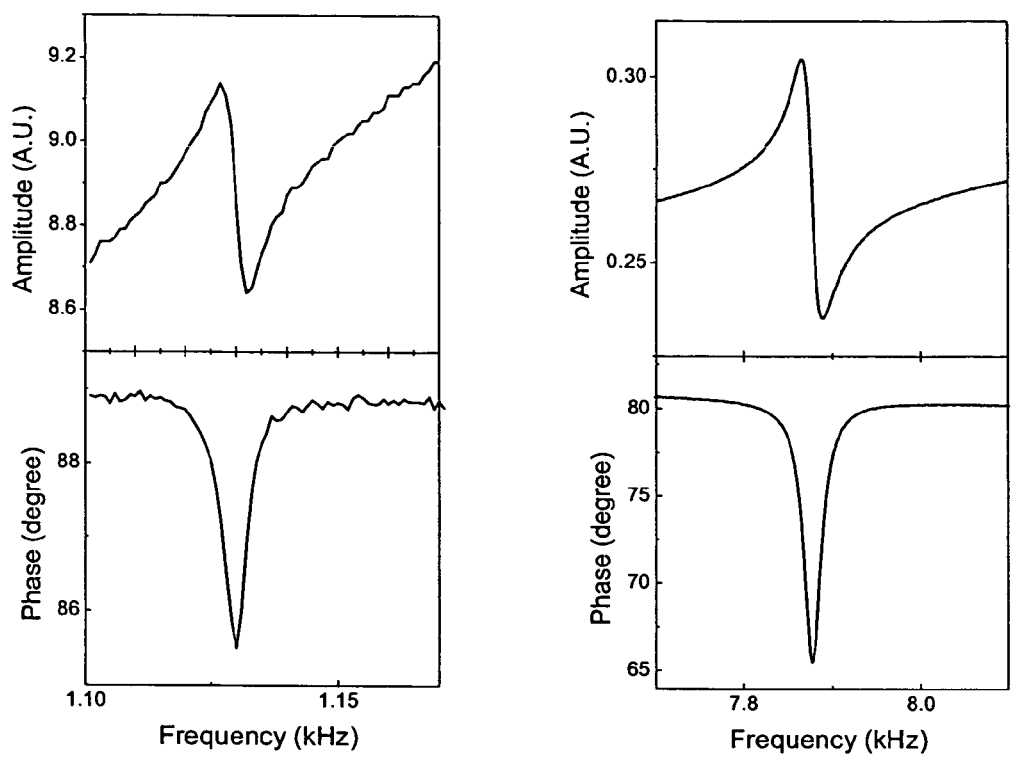
C
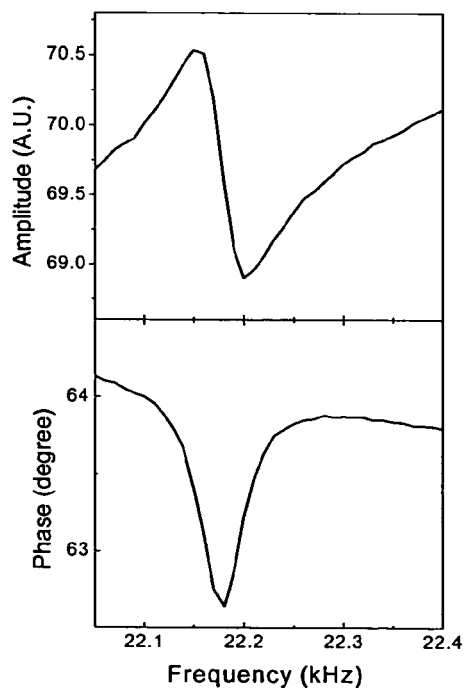
Figure 18

MAGNETOSTRICTIVE LIGAND SENSOR

CROSS-REFERENCE PARAGRAPH

This application claims the benefit of U.S. Provisional Application No. 60/501,953, filed Sep. 10, 2003, which is hereby incorporated herein in its entirety by reference.

FIELD OF THE INVENTION

The invention relates to a magnetostrictive ligand sensor device (MLSD) and system for the analysis of substances using the resonance response of magnetostrictive particles (MSPs).

BACKGROUND OF THE INVENTION

Many applications require detection and identification of ligands, or molecules having particular binding properties. The binding properties of a particular ligand may be detected and characterized by the use of appropriate sensors. "Biosensors" have been reported in the literature and provide an alternative model for molecular screening. Biosensors are often made up of an analytical platform and a binding entity to which the ligand may bind. The detection of a ligand by a biosensor requires a ligand which binds the binding entity and an analytical platform or sensor which generates a detectable signal that can be measured. The analytical platforms measure changes in mass, capacitance, resistance, surface plasma resonance, reflectometric interference, etc. resulting from the interaction of the ligand with the binding entity.

There are particular applications for which functional biosensors would be especially useful but for which biosensors currently in the art are not ideally suited. For example, sensors could be used to screen airplane passenger luggage for trace amounts of pathogens as part of the enhanced national security effort. As another example, sensors could be used to detect pathogens in the food supply. It is estimated that 76 million Americans become ill annually due to ingesting foodborne pathogens and toxins and as many as 5,200 of these individuals will die, with an additional 325,000 being hospitalized. The U.S. Department of Agriculture estimates the cost of foodborne illness to be up to $30 billion in direct medical expenses, lost productivity, and health expenses annually (The Center for Disease Control and Prevention (CDC), News Release, 16 Sep. 1999).

There exist several methods for the general identification of target ligands, such as microbial strains, in water and food. Such methods, however, present challenges, especially when the target ligands are present in relatively small quantities. Thus, for example, many analytical techniques culture live biological target ligands so that they are present in larger, more detectable quantities prior to employing an identification method. Other methods seek to isolate the target ligands using selective binding means.

Polymerase chain reaction (PCR) methods are widely known and used for detection and identification of minute amounts of microbes in a sample. The PCR technique is effective for microbial detection; however, it presents many drawbacks and has special requirements such as a two-hour minimum run time, rigorous sample preparation, complex reactive components having limited shelf life, a precise temperature window, sophisticated PCR hardware, and highly-trained personnel.

Immuno-magnetic separation (IMS) methods seek to concentrate target ligands prior to their analysis and identification in order to provide a more sensitive means for detecting target ligands in a given specimen. In IMS methods, magnetic beads are coated with binding agents that are tailored to bind with the target ligand. The magnetic beads are then circulated within the sample so as to provide an opportunity for the target microbes to bind to their respective surfaces. Magnetic fields are then applied to separate the magnetic beads and the bound target ligands from the specimen sample. The target ligands can then be removed from the beads and analyzed. IMS systems allow the user to remotely manipulate the magnetic beads by the application of a variable magnetic field to the specimen container.

Antibodies are often used as probes and/or binding agents for the detection of target ligands due to their relatively high selectivity. Antibodies against a range of bacteria are widely available, but antibodies are relatively fragile molecules that are subject to denaturation and a consequent loss of sensitivity and other binding characteristics when exposed to unfavorable environments. In addition, the quality of antibodies can vary with production variables such as different animals. In addition, for use in biosensors, antibodies require affinity purification and stabilization, which greatly increases their cost.

Different types of analytical platforms are being used and developed for use as bases for biosensors configured to detect target microbes. Many of these sensor platforms utilize antibodies as binding agents for a target ligand. In order to identify and quantify the capture of target ligands such as pathogens or spores in antibodies or phages, various methods have been used, such as acoustic wave sensors (Pathirana et al. (2000) *Biosensors & Bioelectronics* 15:135-141; Xu et al. (2001) *Sensors and Actuators B* 75:29; Lucklum and Haauptmann (2000) *Sensors and Actuators B* 70:30; Wong et al. (2002) *Biosensors and Bioelectronics* 17:676; Babacan et al. (2000) *Biosensors and Bioelectronics* 15:615), micromachined cantilever force sensors (Baselt et al. (1996) *J. Vac. Sci. Technol.* B142:789; Raiteri et al. (2001) *Sensors and Actuators B* 79:115), and other sensors based on magnetic materials and fiber optics (U.S. Pat. No. 5,981,297; Chio et al. (2000) *Sensors and Actuators B* 68:34).

Some microscale biosensors utilize microcantilevers as analytical platforms, wherein the microcantilevers respond mechanically by deflecting and/or changing resonance frequency when matter attaches, via a specific receptor, to the cantilever's surface (see FIG. 7). One of the schemes for transducing this interaction has been through optical laser systems that resolve the nanometer scale cantilever deflections involved. Although the sensitivity of laser detection is very high, the required equipment is complicated, expensive, and occupies a significant amount of space, which is contrary to the development of compact and cost-effective detection devices. An additional drawback of optical-based measurements is the inability to effectively perform in situ solution measurements.

Other microcantilever analytical platforms utilize microelectromechanical systems (MEMS) that operate by frequency-shift-by-mass-attachment schemes. In these MEMS systems, the microcantilever is driven by an attached oscillator circuit to exhibit oscillatory deflections at a resonance frequency. Changes in the resonance frequency of the oscillating microcantilever caused by the attachment of a target particle are then detected by circuitry attached to the microcantilever. Such MEMS-based systems, however, have several limitations: (1) each sensor requires an attached oscillator circuit and an internal power source to drive the device, (2) the sensor requires the target microbe to be brought to the surface of the sensor (and its associated circuitry and power sources) before detection can occur; and (3) these systems exhibit limited quality merit factors (Q-values) and thus exhibit less-defined resonance response peaks, especially in liquid environments (see, e.g., FIG. 24). These limitations make the detection of target microbes in low concentrations in a specimen very difficult, as it is difficult to bring the components of the entire volume of specimen into contact with the microcantilever surface. In addition, these limitations prevent MEMS systems from detecting target microbes effectively in liquid environments, such as, for example, a water supply.

The current state of the art in biosensor technology includes a number of biosensor designs. For example, U.S. Pat. No. 6,241,863 (with inventor Monbouquette) describes the development of amperometric biosensors based on redox enzymes. U.S. Pat. No. 6,239,255 describes surface plasmon resonance biosensors. Still other biosensors have been described, including biosensors which utilize functionalized microspheres for optical diffraction (U.S. Pat. No. 6,221,579), mass-sensitive biosensors (U.S. Pat. No. 6,087,187), hybrid biosensors (U.S. Pat. No. 6,051,422), metal oxide matrix biosensors (U.S. Pat. No. 5,922,183), silicon-based biosensors (U.S. Pat. No. 5,874,047), solid-supported membrane biosensors (U.S. Pat. No. 5,846,814), fiber-optic chemiluminescent biosensors (U.S. Pat. No. 5,792,621), and others.

Sensors made of magnetostrictive materials are currently used commercially to prevent the theft of high dollar value foods and merchandise (U.S. Pat. No. 6,426,700). Magnetostrictive materials produce a mechanical strain in response to a magnetic field, and also may produce a magnetic field in response to mechanical strain. This transduction/actuation scheme is both inexpensive and robust. A remote sensor for viscosity and temperature has already been developed using magnetostrictive materials (U.S. Pat. No. 6,393,921 (the "'921 patent") and U.S. Pat. No. 6,397,661 (the "'661 patent")). The sensor disclosed in the '661 patent is also capable of sensing an analyte using a chemically responsive outer layer comprising a hydrogel or absorbent polymer. In addition, a similar sensor has been developed for measuring pH and $CO_2$ levels; this sensor makes use of a change in the mass of a polymer (Jain et al. (2001) *Smart Materials and Structures* 12:347; Cai et al. (2000) *J. of Environmental Monitoring* 2:556). Thus, magnetostrictive sensors are useful not only as biosensors but also are useful in a variety of other applications.

Magnetostrictive materials are generally known in the art, as are methods for evaluating and modifying their properties. Similarly, sensors comprising magnetostrictive materials are known in the art. See, for example, the '661 patent, the '921 patent, U.S. Pat. Nos. 6,579,612; 6,352,649; 6,273,965; 6,093,337; 5,821,129; 5,773,156; 5,043,693; Wing Or et al. (2003) *J. Magnetism and Magnetic Materials* 262: L181-L185; Na et al. (2003) *J. App. Physics* 93: 8501-8503; Kaniusas et al. (2003) *J. Magnetism and Magnetic Materials* 254-255: 624-626; Vassiliev (2002) *J. Magnetism and Magnetic Materials* 242-245: 66-67; Ludwig et al. (2002) *J. Magnetism and Magnetic Materials* 242-245: 1126-1131; Kraus et al. (2002) *J. Magnetism and Magnetic Materials* 242-245: 269-272; Ishiyama et al. (2002) *J. Magnetism and Magnetic Materials* 242-245: 1163-1165; Duenas et al. (2002) *J. Magnetism and Magnetic Materials* 242-245: 1132-1135; Jain et al. (2001) *Applied Acoustics* 62: 1001-1011; Jain et al. (2001) *Smart Materials and Structures* 10: 347-353; Cobeno et al. (2001) *Sensors and Actuators A: Physical* 91: 95-98; Chiriac et al. (2001) *Sensors and Actuators A: Physical* 91: 107-111; Mehnen et al. (2000) *J. Magnetism and Magnetic Materials* 215-216:779-781; Hristoforou (2000) *Sensors and Actuators A: Physical* 81: 142-146; Chiriac et al. (2000) *Sensors and Actuators A: Physical* 81: 166-169; Batt et al. (2000) *Sensors and Actuators A: Physical* 81: 170-173; Barandiaran et al. (2000) *Sensors and Actuators A: Physical* 81:154-157; Quandt (1997) *J. Alloys and Compounds* 258: 126-132; Hristoforou et al. (1997) *Sensors and Actuators A: Physical* 59: 84-88; Hristoforou et al. (1997) *Sensors and Actuators A: Physical* 59: 89-93; Atkinson and Duhaj (1996) *J. Magnetism and Magnetic Materials* 157-158: 156-158; Gutierrez and Barandiaran (1995) *IEEE Transactions on Magnetics* 31: 3146-3148; Klinger et al. (1992) *IEEE Transactions on Magnetics* 28: 2400-2402; Greenough et al. (1991) *J. Magnetism and Magnetic Materials* 101: 75-80; Hornreic et al. (1971) *IEEE Transactions on Magnetics* MAG7: 29; Mungle et al. (2002) *Sensors and Actuators A: Physical* 101: 143-149; Michelena et al. (2002) *Sensors and Actuators A: Physical* 100: 153-159; Cai and Grimes (2001) *Sensors and Actuators B: Chemical* 79: 144-149; Hristoforou et al. (1998) *Sensors and Actuators A: Physical* 67: 49-54; Kim (1995) *Materials Science and Engineering B* 34: 1-6. Thus, those of skill in the art know how to modify the composition and construction of magnetostrictive sensors to achieve the desired end result. See also, for example, Shieh et al. (2001) *Progress in Materials Science* 46: 461-504; Germano et al. (2000) *Sensors and Actuators A: Physical* 81: 134-136; Hristoforou (1997) *Sensors and Actuators A: Physical* 59: 183-191; Feng et al. (2003) *Mechanics of Materials* 35: 623-631.

However, the need remains for magnetostrictive biosensors for the detection and quantification of target ligands wherein the biosensors are small, sensitive, readily prepared, and have robust binding elements. For many applications, remotely interrogable or wireless sensors would be particularly useful. The need also exists for the development of a range of sensors that are capable of detecting very small amounts of various liquid- and foodborne pathogens that may be present in various liquids, gases, beverages, and foods during processing, storage, transportation, and marketing. In addition, a need exists for remotely interrogable, wireless sensors having an improved sensitivity for a variety of applications, including in-package monitoring of food and beverages. Such wireless sensors would be useful not only in detecting biological agents but also in evaluating environmental conditions such as, for example, temperature and humidity.

SUMMARY OF THE INVENTION

Provided are sensors as well as sensor systems and methods of use. The sensors include devices referred to herein as "magnetostrictive ligand sensor devices" ("MLSDs"). MLSDs comprise at least one magnetostrictive particle which has a characteristic resonance response and which is coupled to a binding element. The binding element may comprise a single substance such as, for example, a hydrogel, or the binding element may comprise multiple substances. In some embodiments, the binding element comprises a binding agent (such as, for example, a peptide) that binds selectively to at least one target ligand. The sensor systems further provide a measurement device configured to detect the resonance response of the magnetostrictive particle. The measurement device detects changes in the resonance response of the magnetostrictive particle that occur due to changes in the binding element and/or as a result of interactions between the binding element and its environment, including substances that come into contact with the binding element.

In some embodiments, a varying magnetic field is applied to the magnetostrictive particle by a remote driver that induces the magnetostrictive particle to oscillate at a characteristic resonance frequency, which in turn produces the resonance response in the form of a time-varying magnetic field. The sensor system may also include a remote pick-up coil for detecting the time-varying magnetic field produced by the magnetostrictive particle. Thus, in some embodiments, the sensor system is capable of wireless remote detection and quantification of the target ligand within a sample by, for instance, remotely interrogating at least one magnetostrictive particle.

In this manner, the invention provides assays for the rapid discovery of ligands specific to various binding elements and also finds use in the detection of a wide range of biological, organic, chemical, and other materials present in small amounts.

BRIEF DESCRIPTION OF THE SEVERAL VIEWS OF THE DRAWINGS

Having thus described the invention in general terms, reference will now be made to the accompanying drawings, which are not necessarily drawn to scale.

FIG. 1 shows a schematic of an embodiment of the magnetostrictive ligand sensor device (MLSD) of the present invention.

FIG. 2 shows a comparative graph of two different resonance responses of a magnetostrictive particle according to one embodiment of the present invention.

Figure 3:
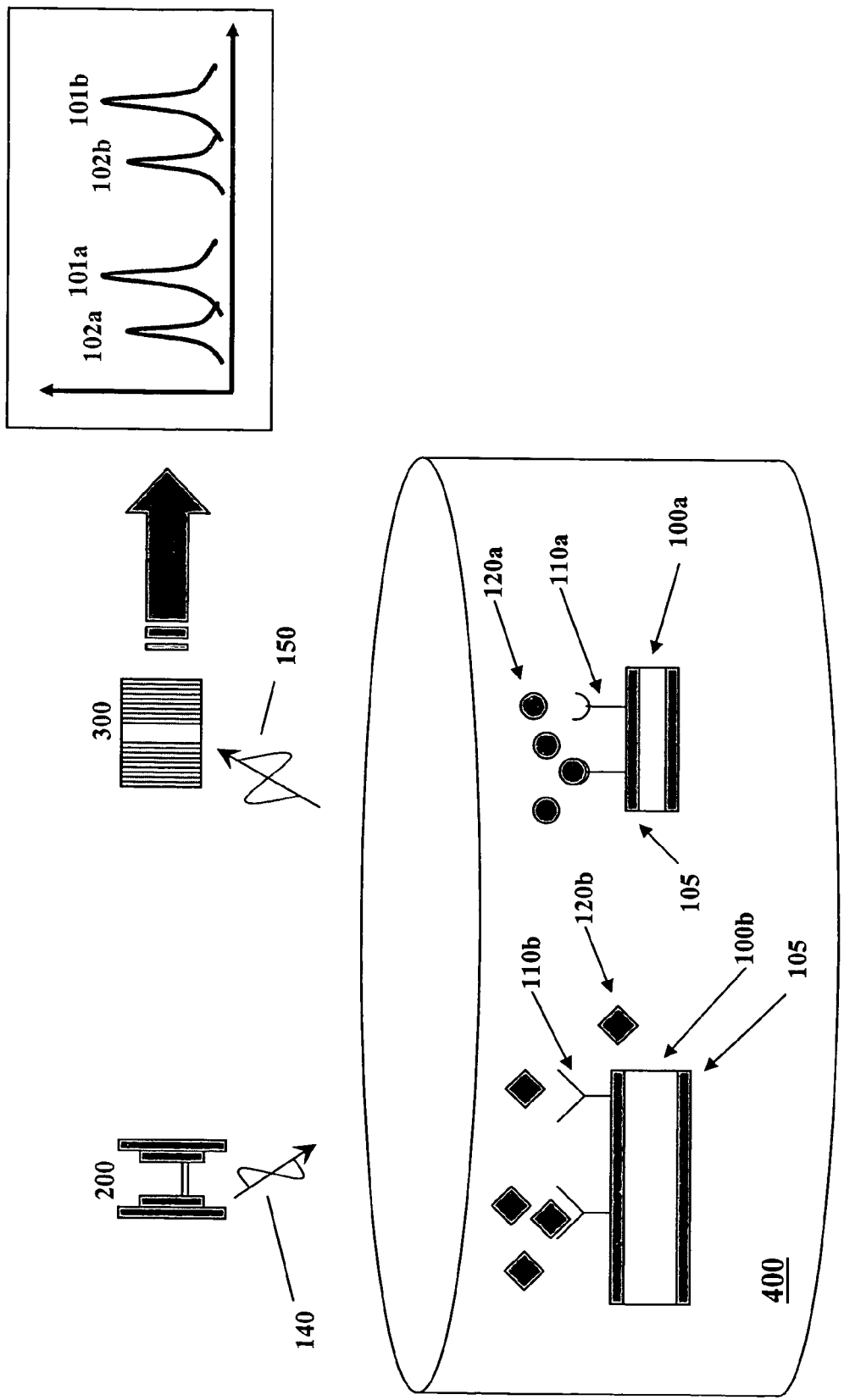

FIG. 3 shows a comparative graph of two different resonance responses of two different magnetostrictive particle sizes and an accompanying schematic of the two magnetostrictive particles and their corresponding binding elements and target ligands.

Figure 4:
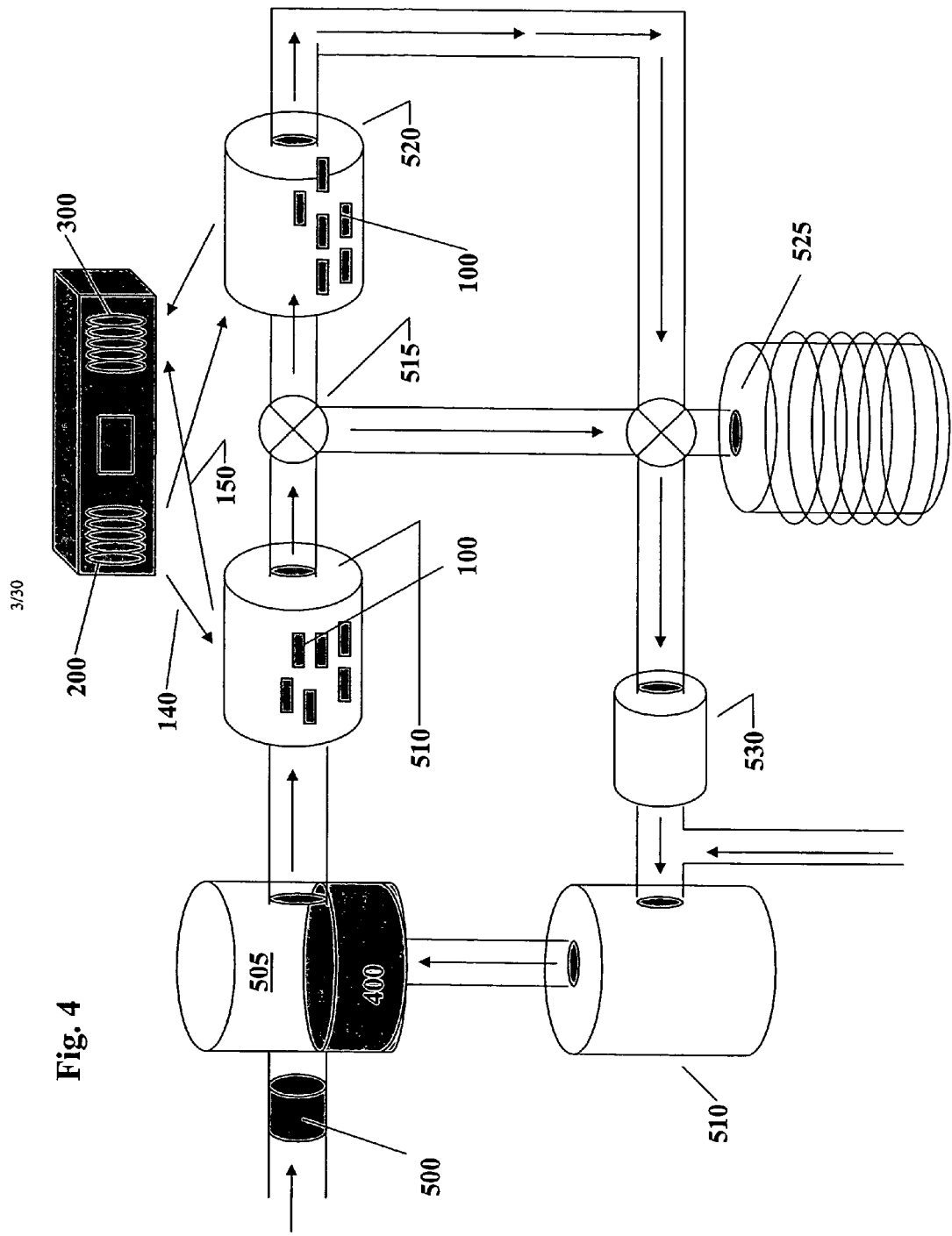

FIG. 4 shows a schematic of one embodiment of a sensor system according to the present invention including an air-to-liquid concentrator and a dual chamber detection and characterization stage for detection and quantification of the target ligands in, for instance, an air sample.

Figure 5:
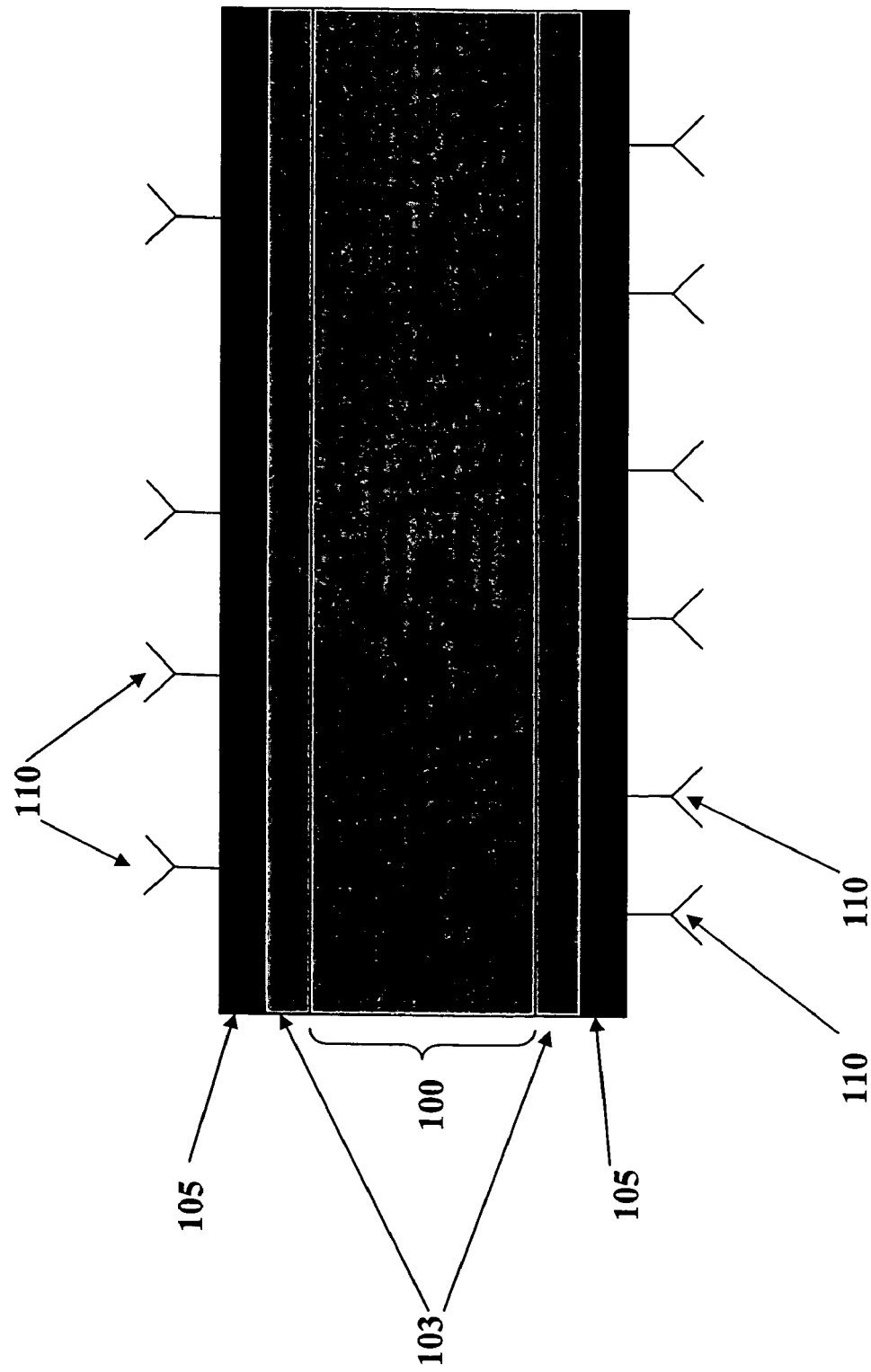

FIG. 5 shows a schematic of one embodiment of a magnetostrictive ligand sensor device (MLSD) of the present invention including a coating and coupling composition layer applied to a magnetostrictive particle (MSP).

Figure 6:
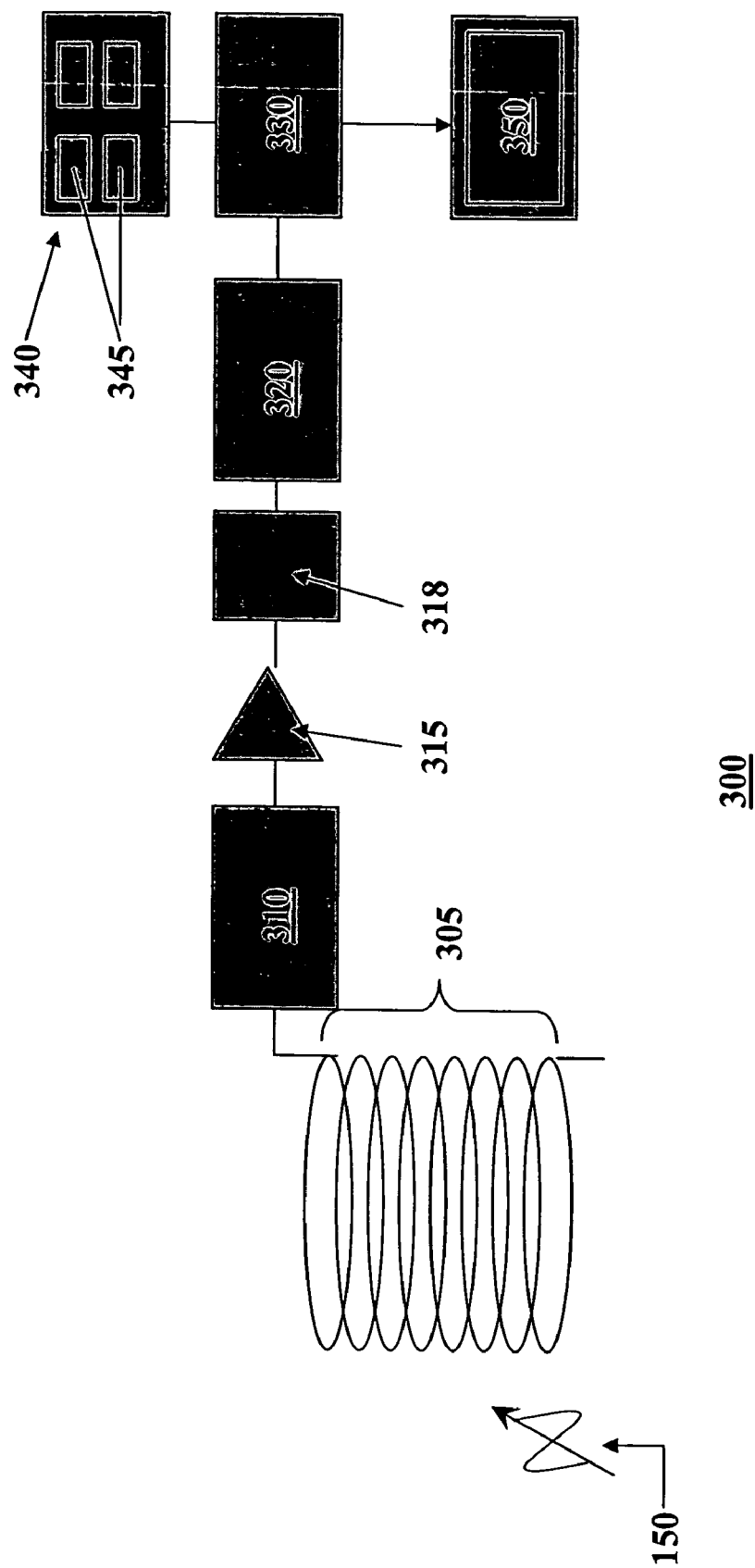

FIG. 6 shows a schematic of the pick up coil and associated circuitry according to one embodiment of the measurement device of the present invention.

Figure 7:
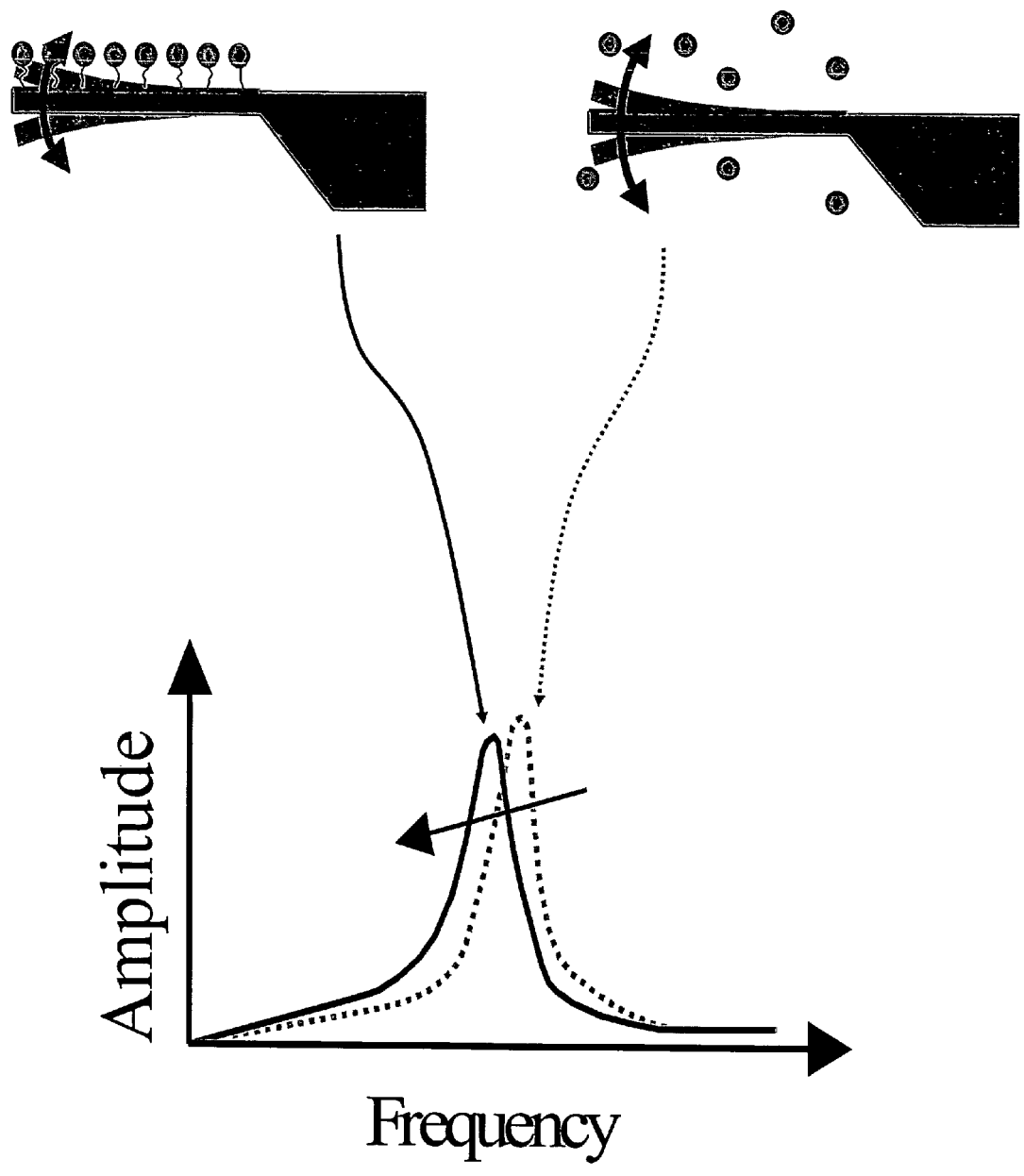

FIG. 7 illustrates the change in behavior of a microcantilever when matter attaches via a specific receptor to the surface of the microcantilever.

Figure 8:
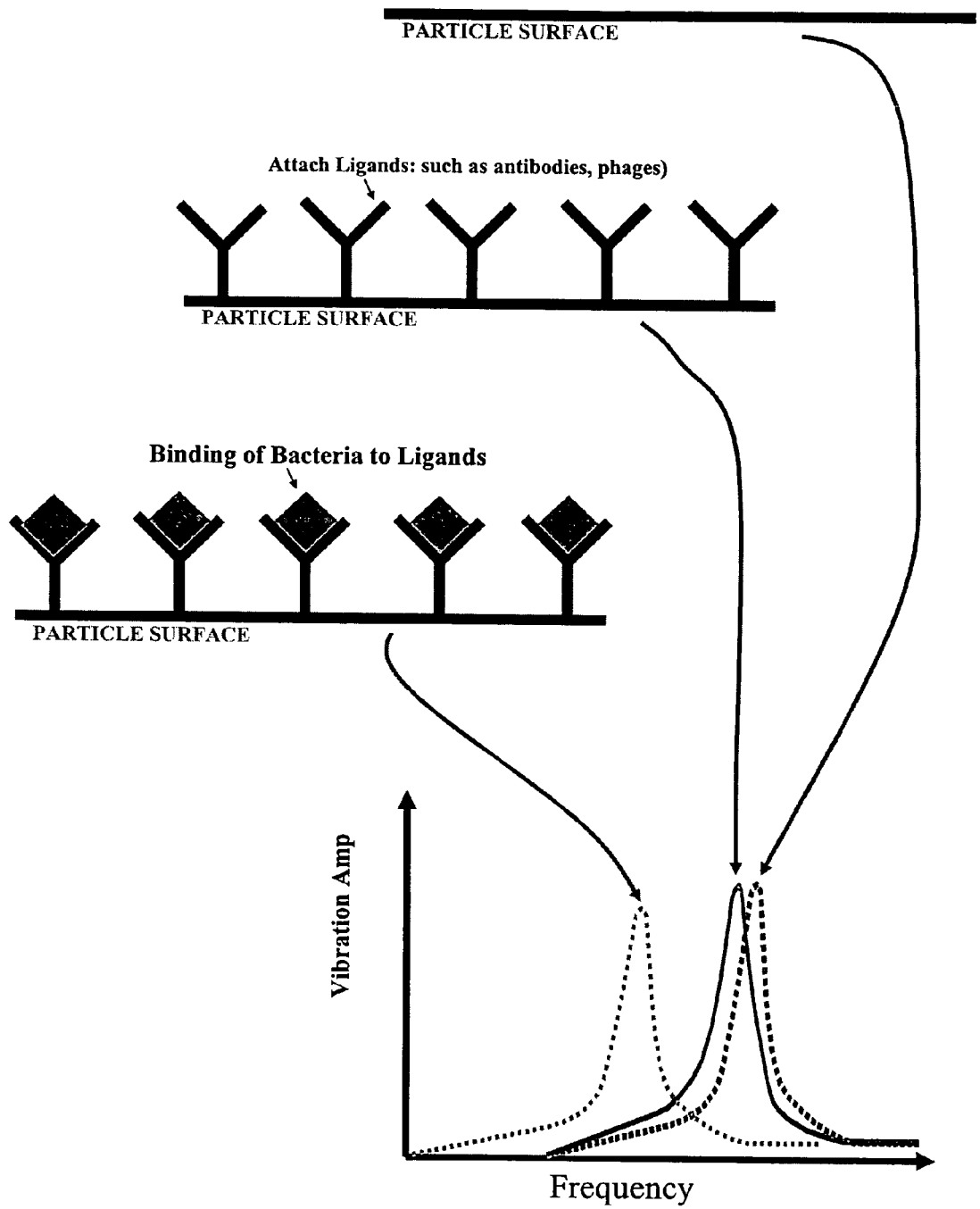

FIG. 8 illustrates changes in resonance frequency of a particle that are observed when a magnetostrictive particle is used to create an MLSD of the invention by attaching a binding element and then binding a particular ligand to that binding element.

Figure 9:
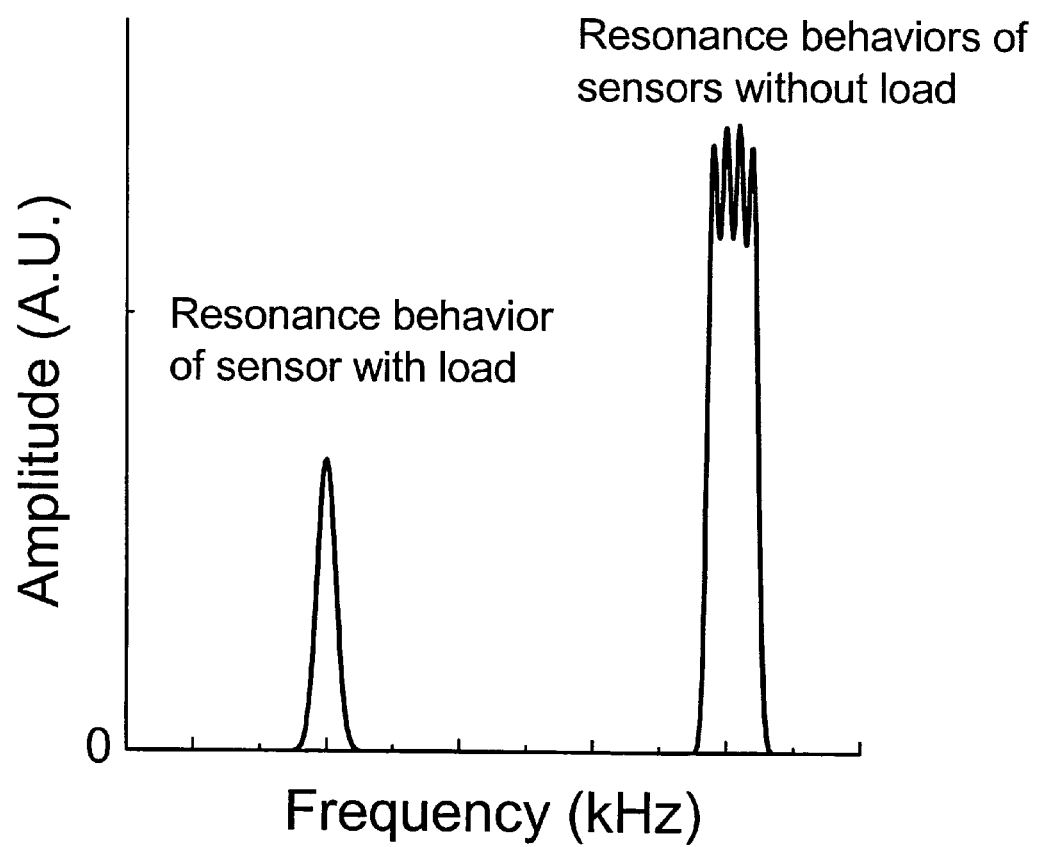

FIG. 9 illustrates that when multiple magnetostrictive particles are evaluated by a frequency scan, a magnetostrictive particle with a ligand attached thereto will be detectable by a shift in resonance frequency.

Figure 10:
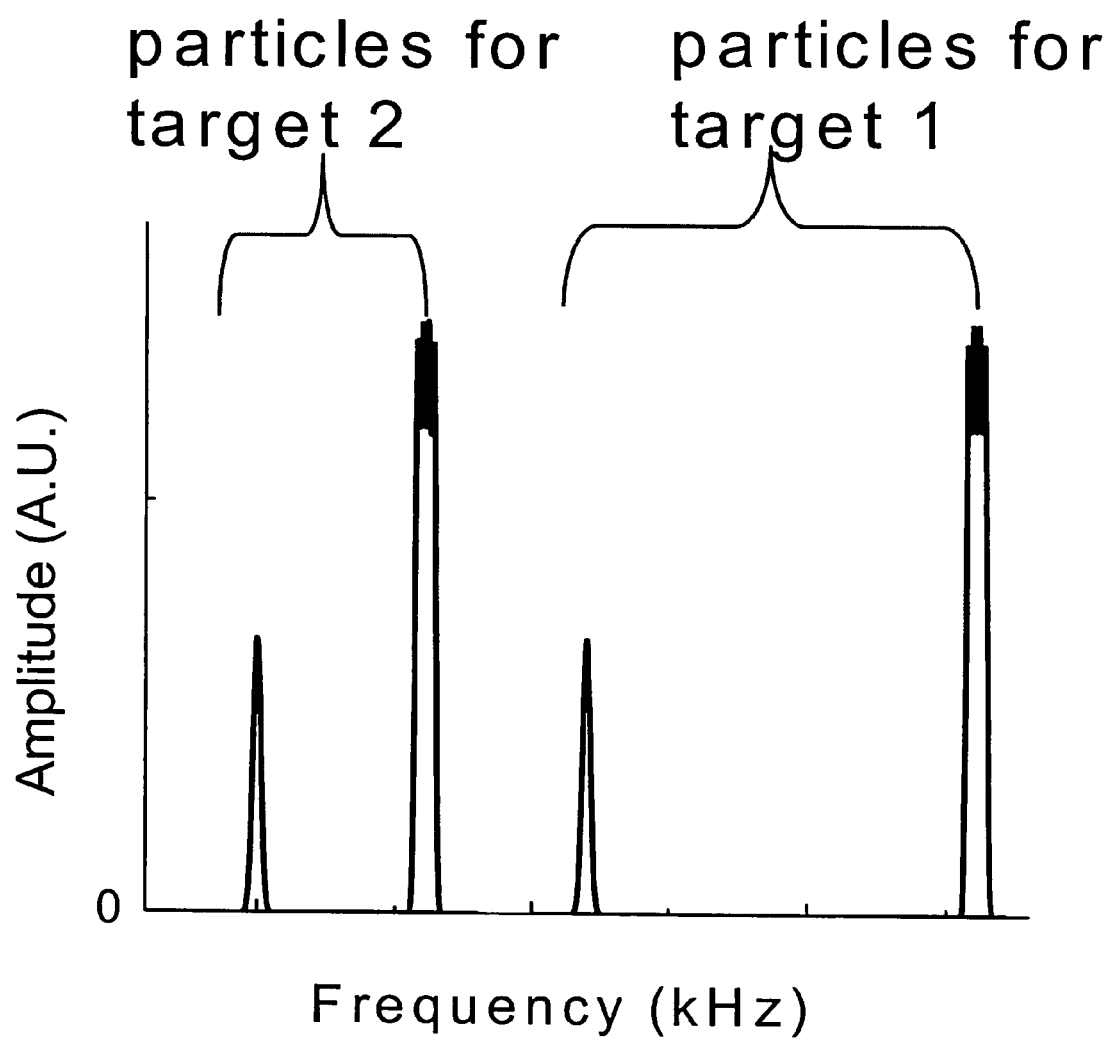

FIG. 10 illustrates the use of different magnetostrictive particles in an MLSD. Where the sensor device comprises more than one type of magnetostrictive particle, the known characteristic resonance frequencies of the different particle types can be analyzed for the appearance of new peaks resulting from the binding of a ligand, as shown.

Figure 11:
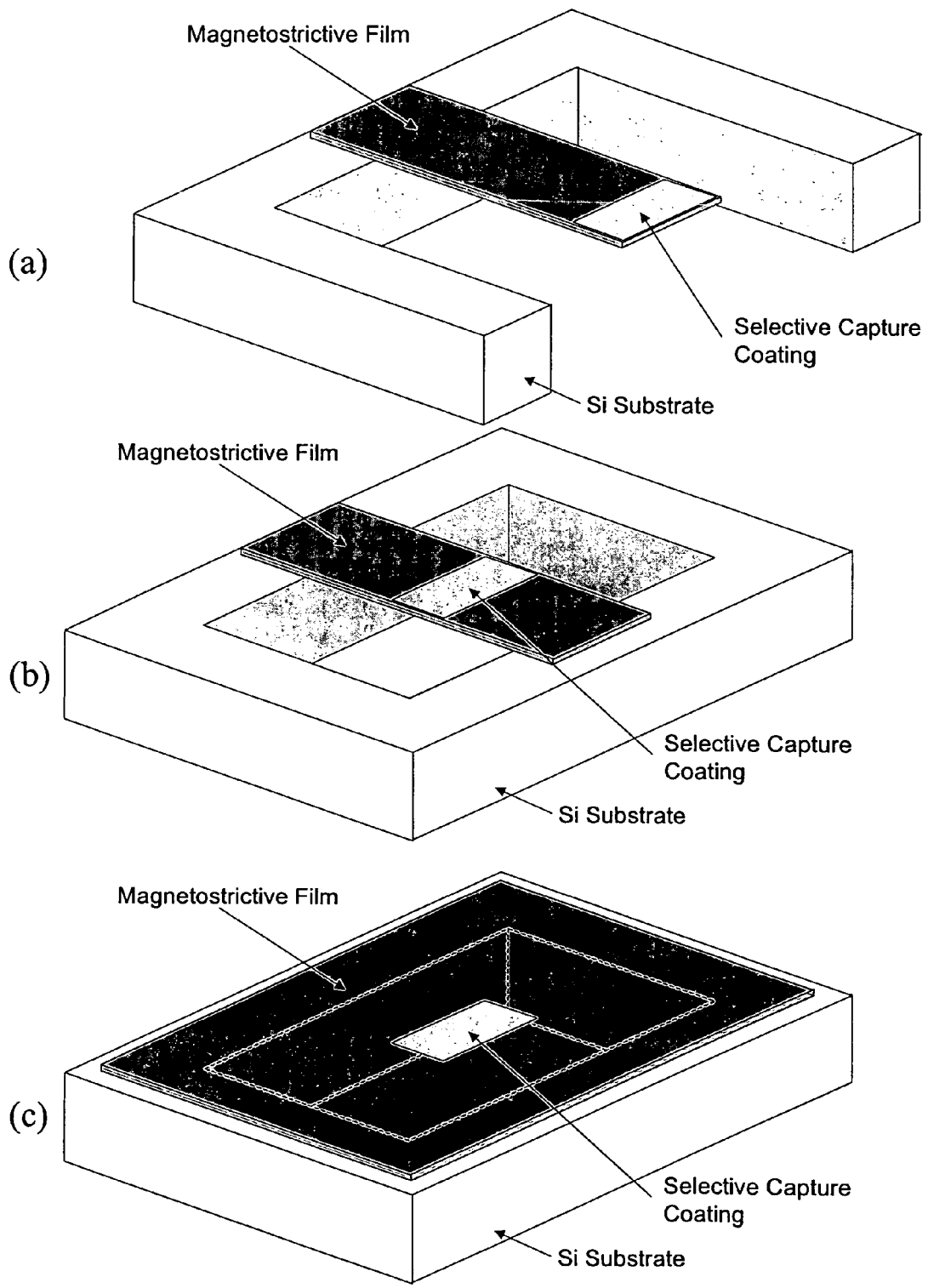

FIG. 11 is a schematic representation of the cantilever (a), bridge (b), and membrane (c) configurations for microsensor MLSDs.

Figure 12:
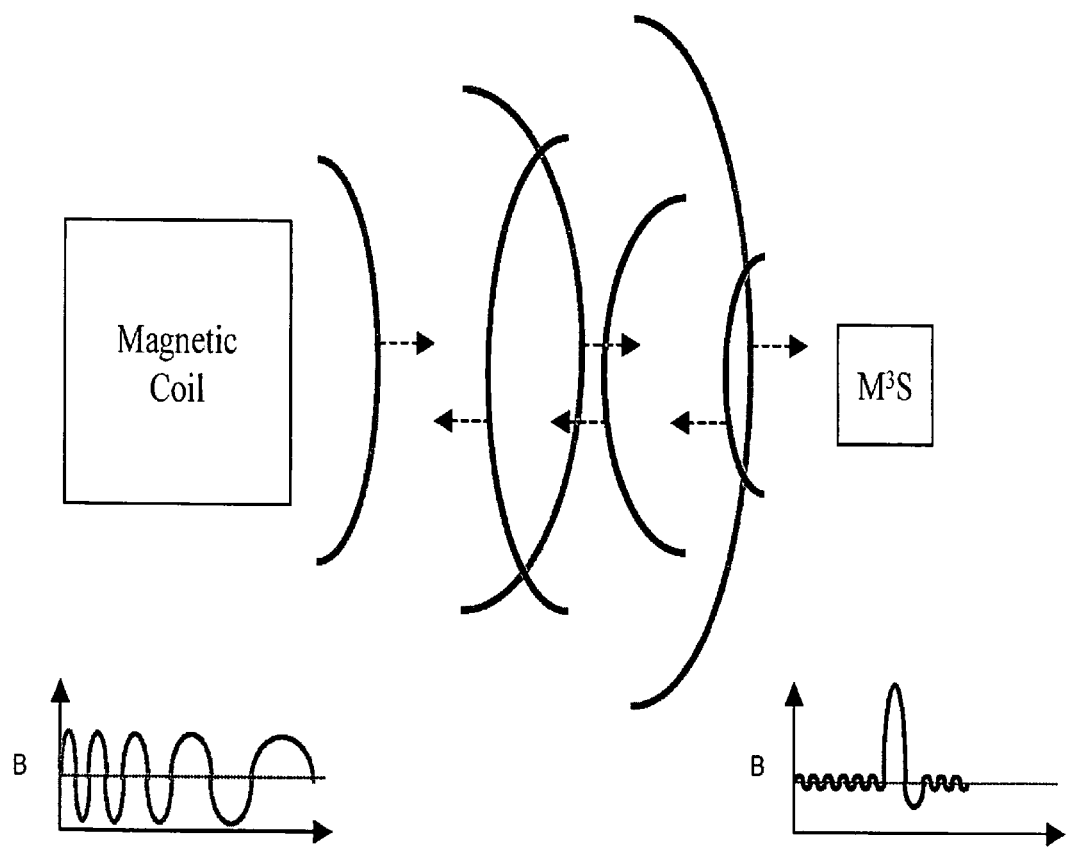

FIG. 12 illustrates the driving and reading magnetic fields for a microsensor device ("M$^3$S").

Figure 13:
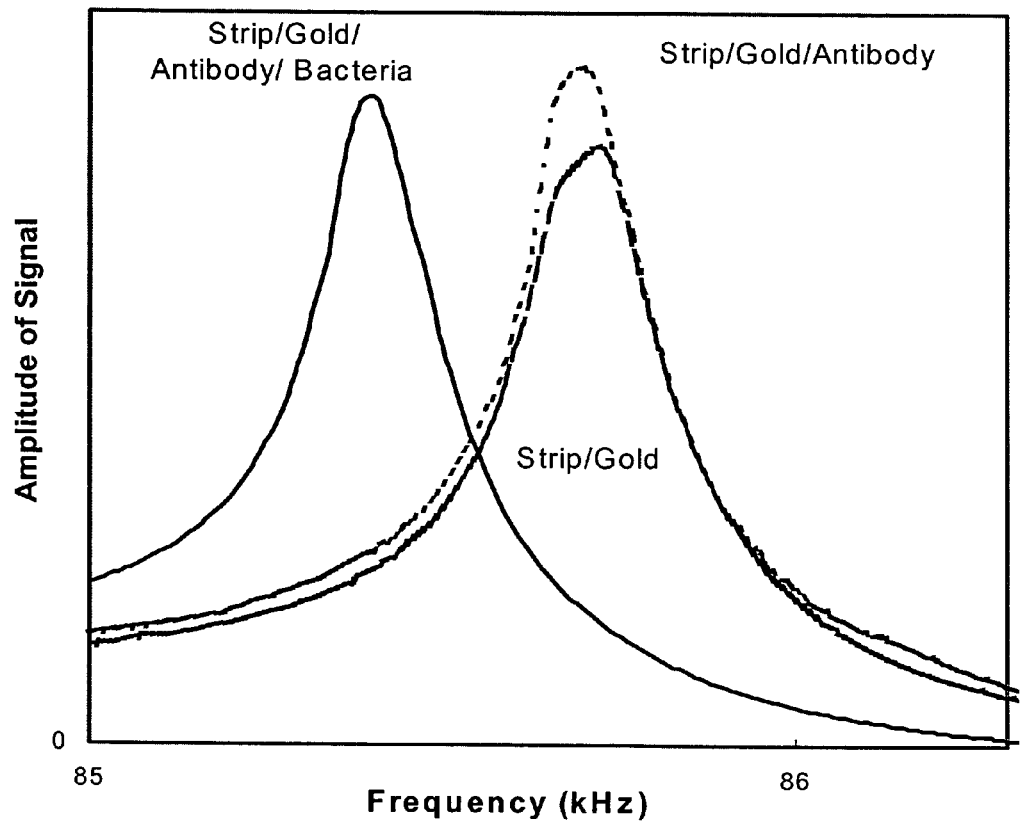

FIG. 13 illustrates the amplitude of magnetic signal from an MLSD having a strip-like conformation. The signal was remotely measured using a pickup coil. The line labeled "Strip/Gold" was obtained from the magnetostrictive strip coated with only gold. The curve labeled "Strip/Gold/Antibody" was obtained from the gold-coated magnetostrictive strip with antibodies immobilized onto it to create an MLSD. The curve labeled "Strip/Gold/Antibody/Bacteria" was obtained after exposure of the MLSD to a liquid sample with a known concentration of *Salmonella*. The difference in resonance frequency between Strip/Gold and Strip/Gold/Antibody is <20 Hz, while that between Strip/Gold/Antibody and Strip/Gold/Antibody/Bacteria is 310 Hz.

FIGS. 14A, 14B, and 14C show micrographs of scanning electron microscopic (SEM) examination of three magnetostrictive resonators exposed to different concentrations of *Salmonella typhimurium* bacteria. The capture of *Salmonella typhimurium* bacteria by the immobilized antibody layer results in a shift of resonance frequency of: 110 Hz for low concentration ($10^4$ cells/ml; FIG. 14A), 310 Hz for medium concentration ($10^6$ cells/ml; FIG. 14B), and 550 Hz for high concentration ($10^8$ cells/ml; FIG. 14C). The image (b) corresponds to the data shown in FIG. 13 (see also Example 1).

Figure 15:
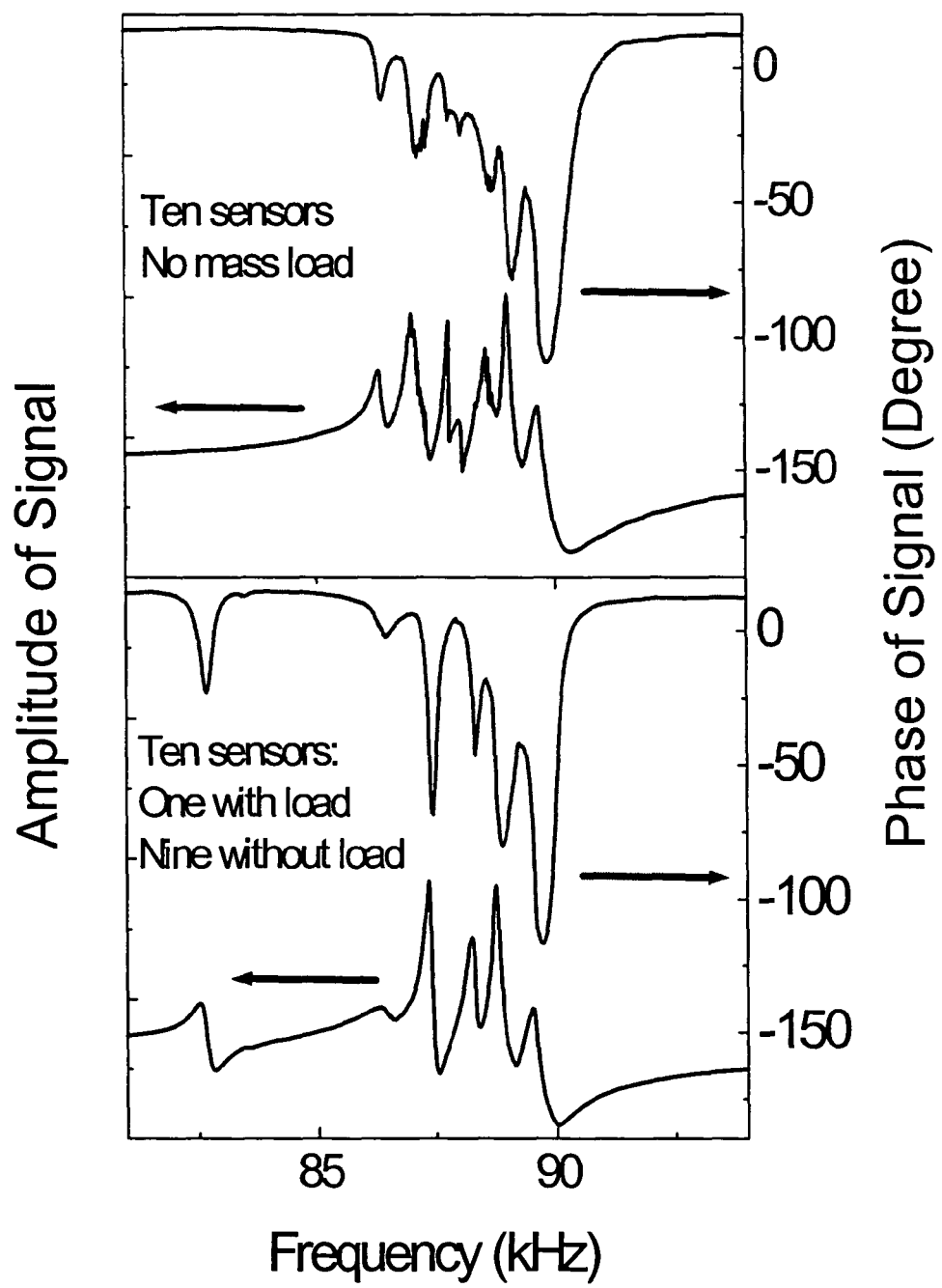

FIG. 15 shows results from an experiment involving the simultaneous use of multiple particles as sensors. In this experiment, ten particles nearly identical in size were prepared and coated with gold. These sensors were placed together and simultaneously measured in the absence of mass load (data shown in top graph in FIG. 15). The ten particles show similar resonance frequencies clustering over a narrow range of frequencies. One particle was then removed and a mass was added to it; the particle was then replaced into the group and measurements were taken again. The lower curve in FIG. 15 clearly shows the appearance of one peak at a lower frequency due to the mass loading.

Figure 16:
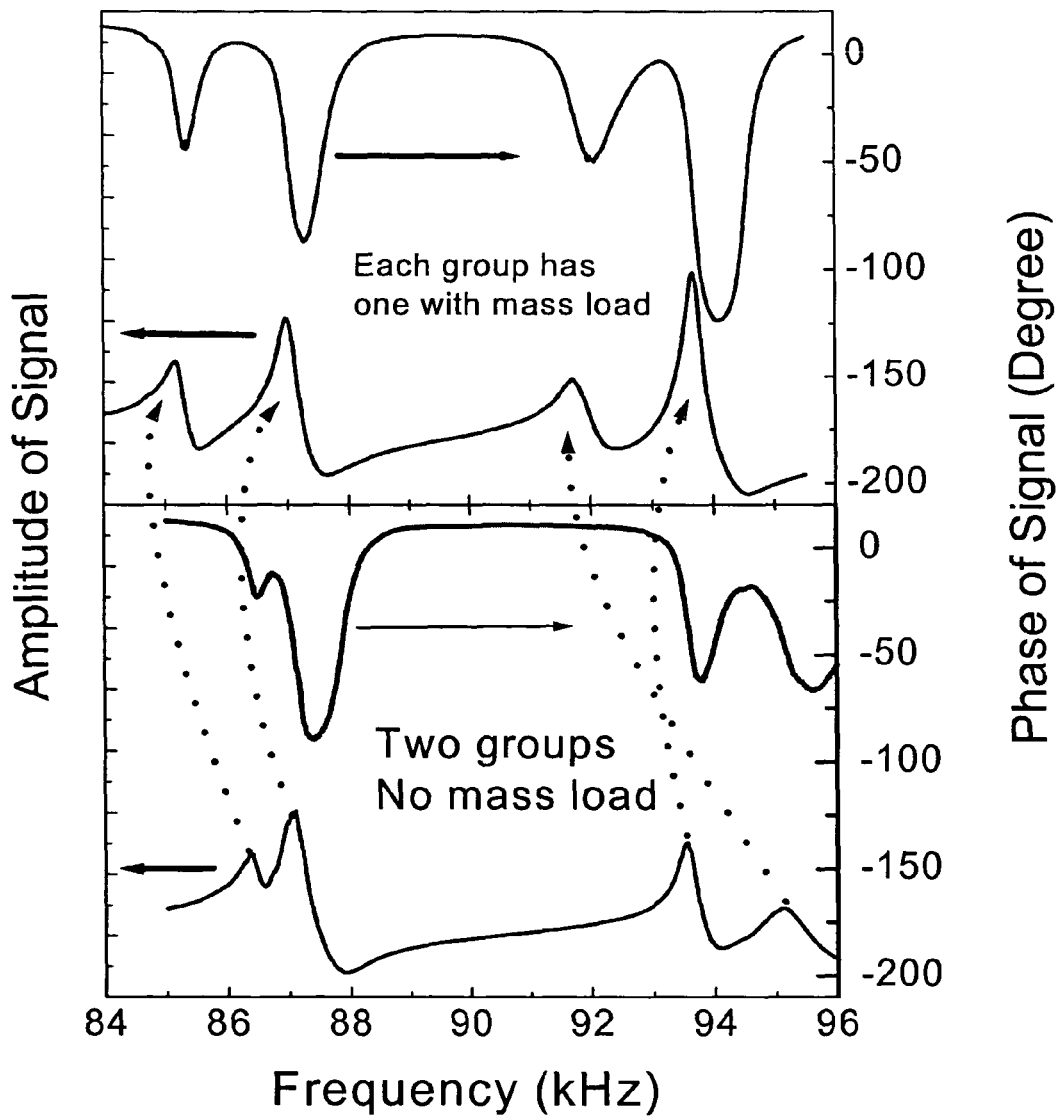

FIG. 16 shows the results of an experiment to analyze the presence of multiple ligands simultaneously using MLSDs comprising particles. Two sets (i.e., collections) of particles were designed and created to have different resonance frequencies of 87 and 94 kHz. The bottom figure represents the resonance frequencies when no mass load was present, and the top figure shows the resonance frequencies when one of two sensors in each set was loaded with a mass.

Figure 17:
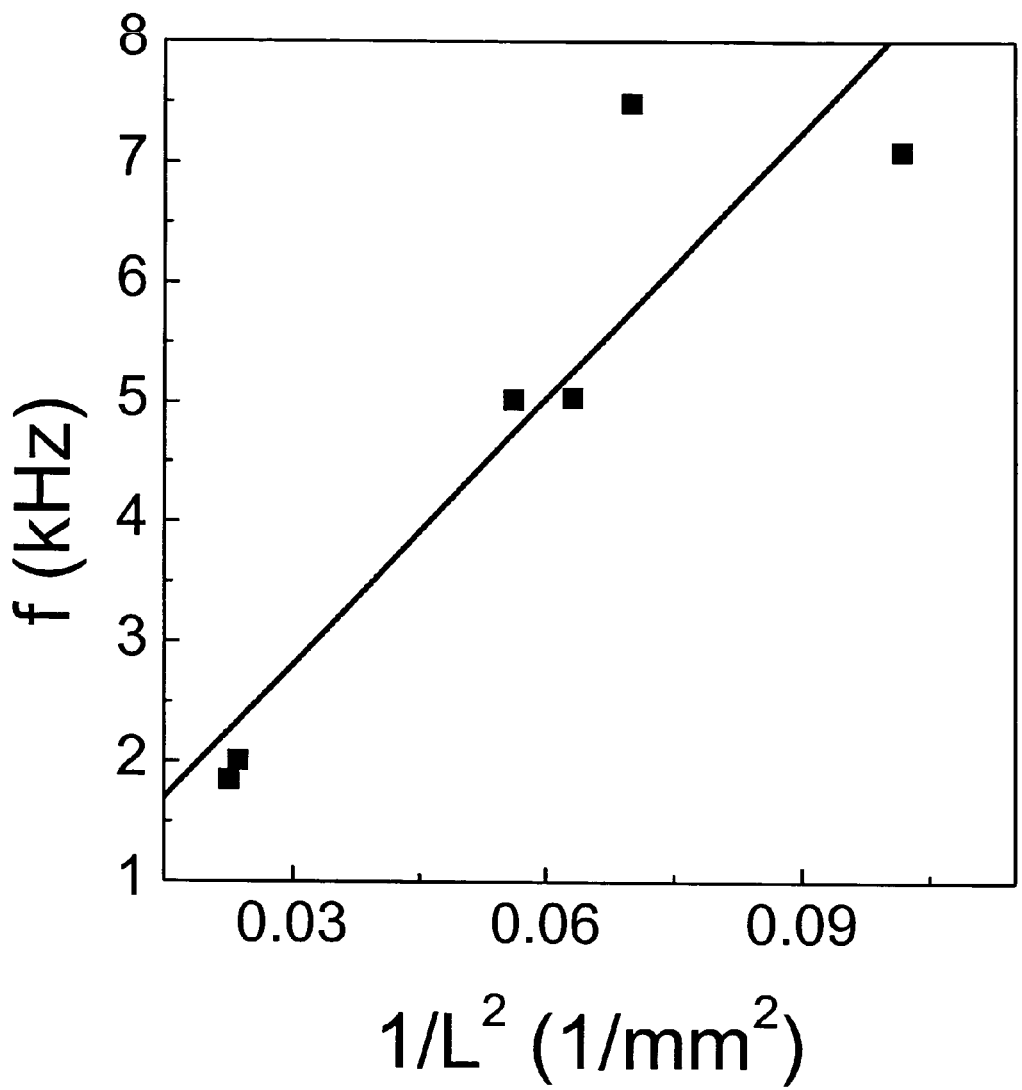

FIG. 17 shows results from a micro-cantilever experiment in which a unimorph-like device was created by bonding magnetostrictive film with metal film; the figure shows the relationship between the resonance frequency (f in kHz) and the length of the cantilever (L in mm).

FIGS. 18A, 18B, and 18C show the resonance behavior of a micro-cantilever. FIG. 18A shows a first harmonic with a resonance frequency of 1.13 kHz, Q=282.5; FIG. 18B shows a second harmonic with a resonance frequency of 7.87 kHz, Q=508; and FIG. 18C shows a third harmonic with a resonance frequency of 22.16 kHz, Q=554.

Figure 19:
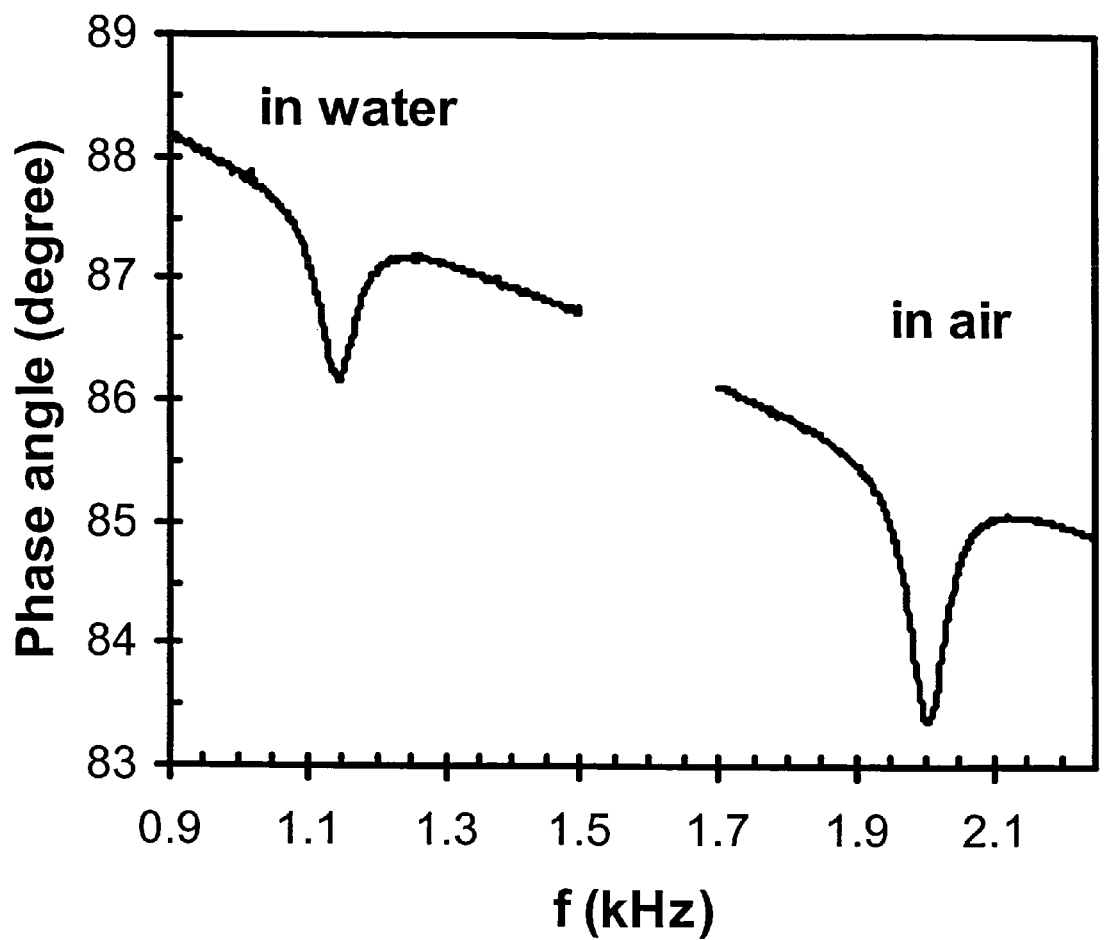

FIG. 19 compares the resonance behavior of micro-cantilever MLSD in both liquid and air, and illustrates that this MLSD functions well in both.

Figure 20:
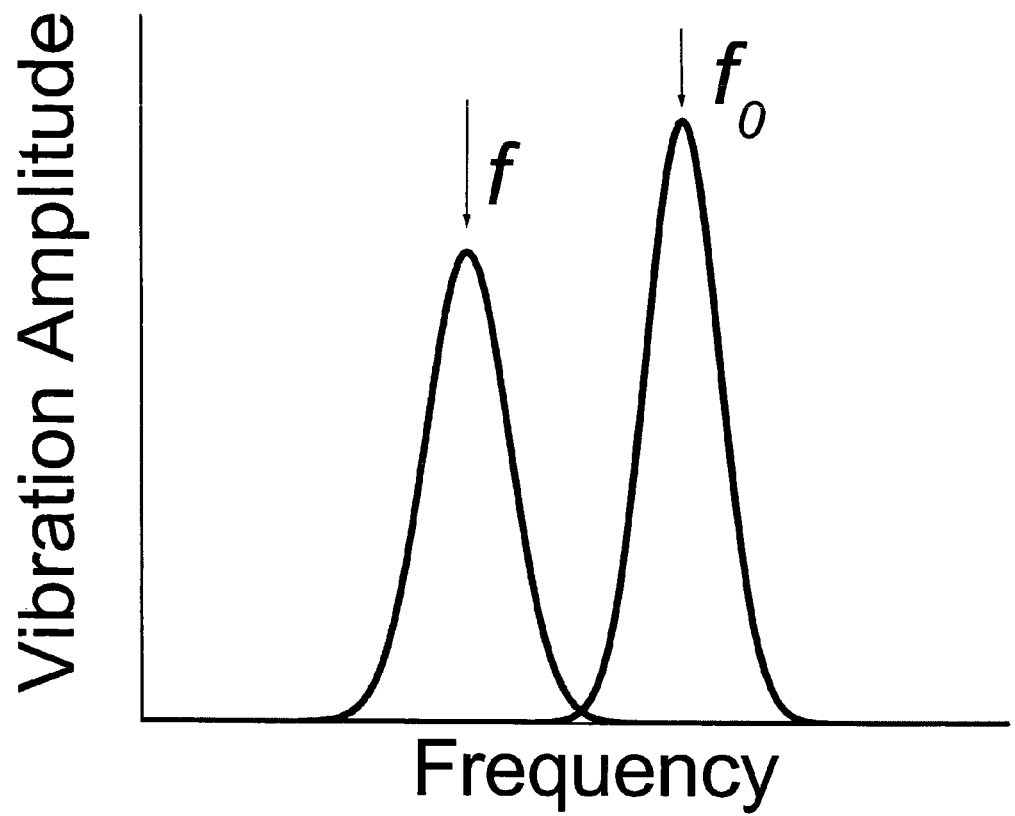

FIG. 20 shows a schematic of vibration amplitude versus frequency of acoustic-wave sensors where $f_o$ and f are the resonance frequency of sensor at zero mass load and at a mass load (m) respectively.

Figure 21:
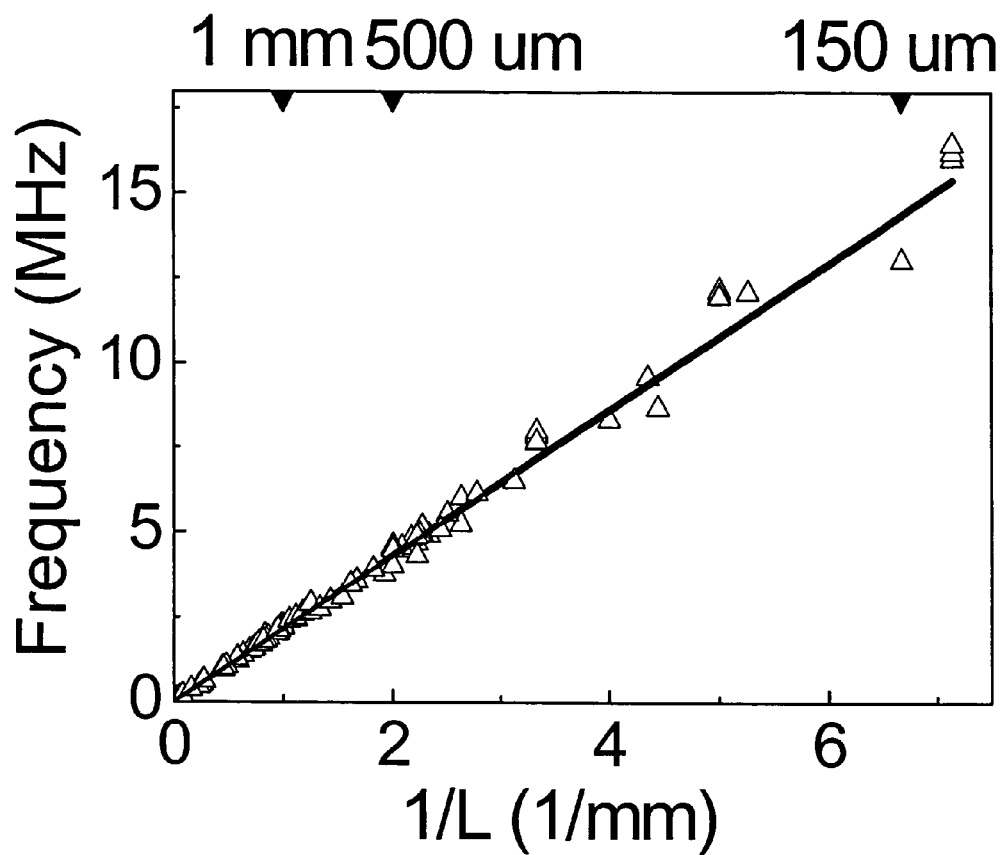

FIG. 21 shows frequency as a function of length of an MSP made of Metglas® solution 2826 MB. The solid line shows theoretical results obtained from equation (5), and triangles represent experimental results.

Figure 22:
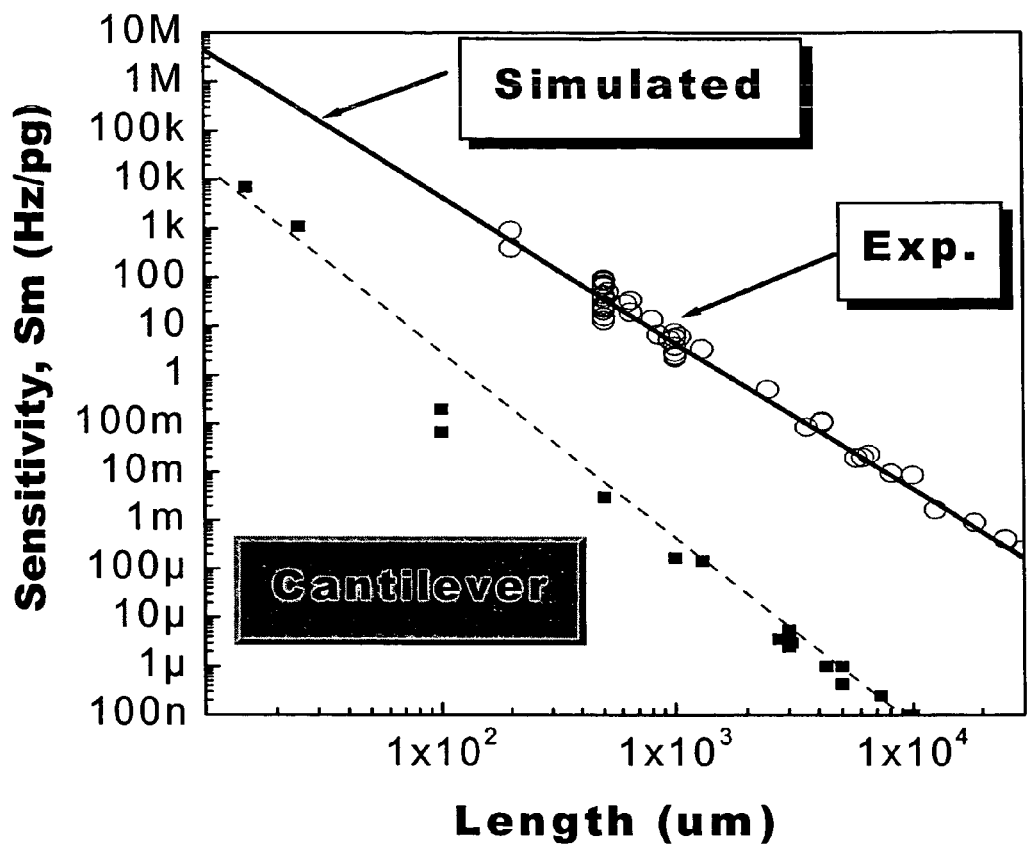

FIG. 22 shows a comparison of the mass-detection sensitivities ($S_m$) (See Equation (2)) of cantilevers and MSPs (in Hz/pg) as a function of the length (in micrometers).

Figure 23:
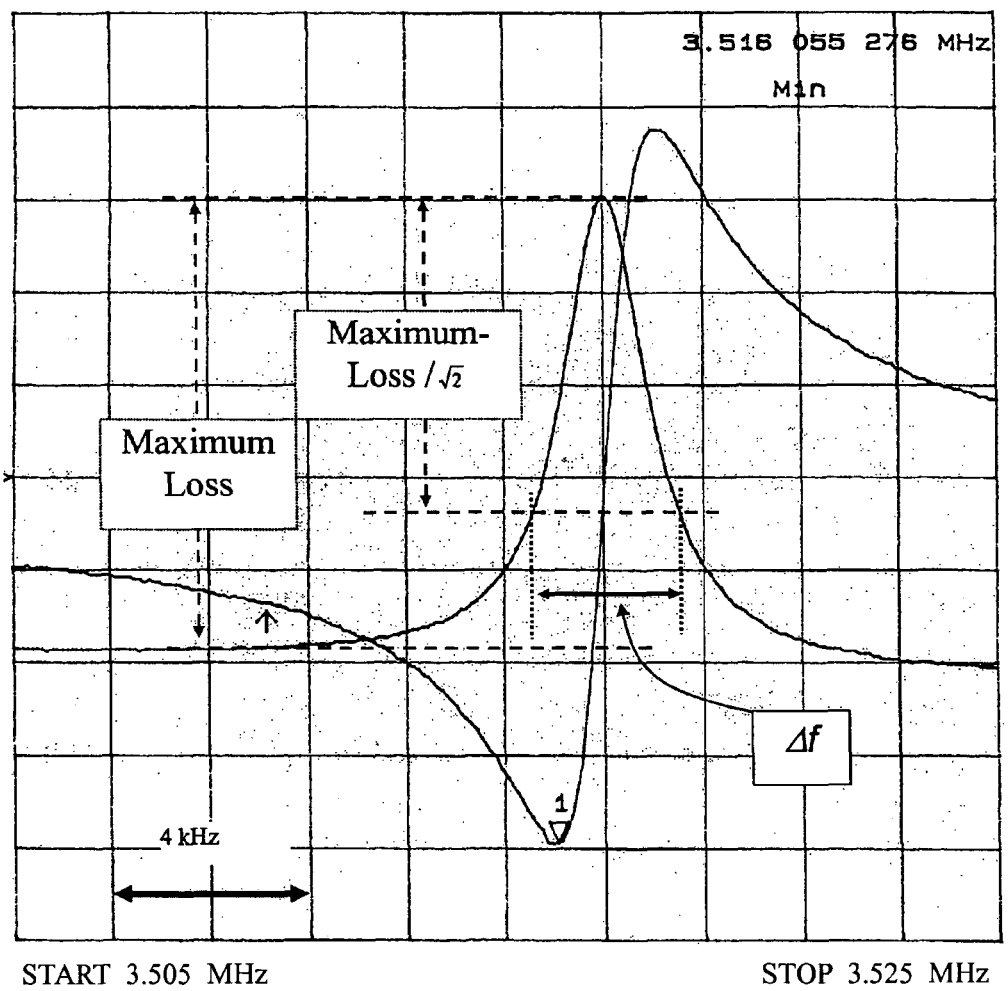

FIG. 23 shows the resonance behavior obtained from an MSP with dimensions 600 micrometers×200 micrometers× 20 micrometers. The resonance frequency was 3.517 MHz. Δf was approximately 3 kHz and the Q value was greater than 1000.

Figure 24:
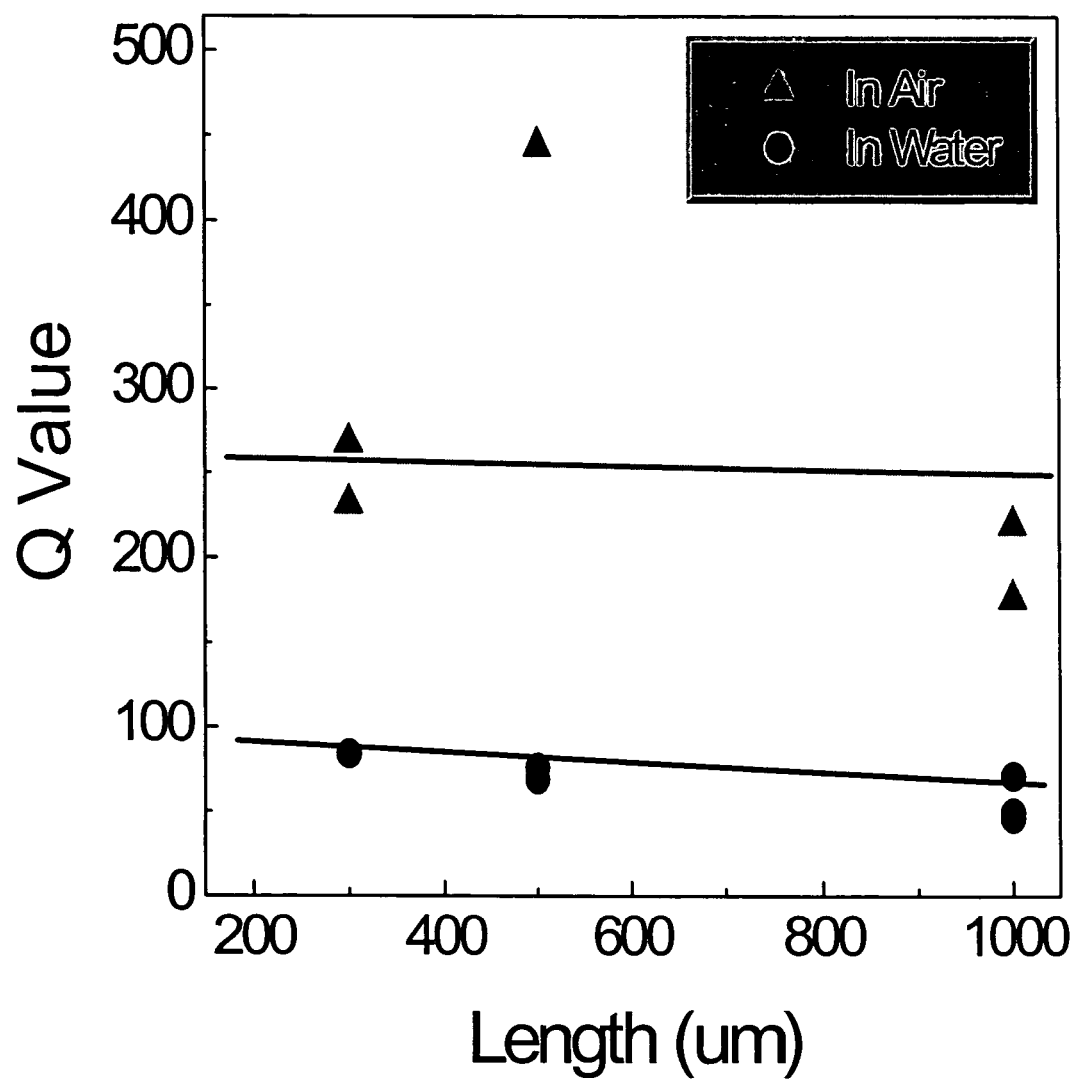

FIG. 24 shows the Q value as a function of length of strip-like magnetostrictive particles in air and water, respectively. As shown, MSP Q values are much greater than the reported microcantilever Q values of 40 to 100 in air and less than 10 in water.

Figure 25:
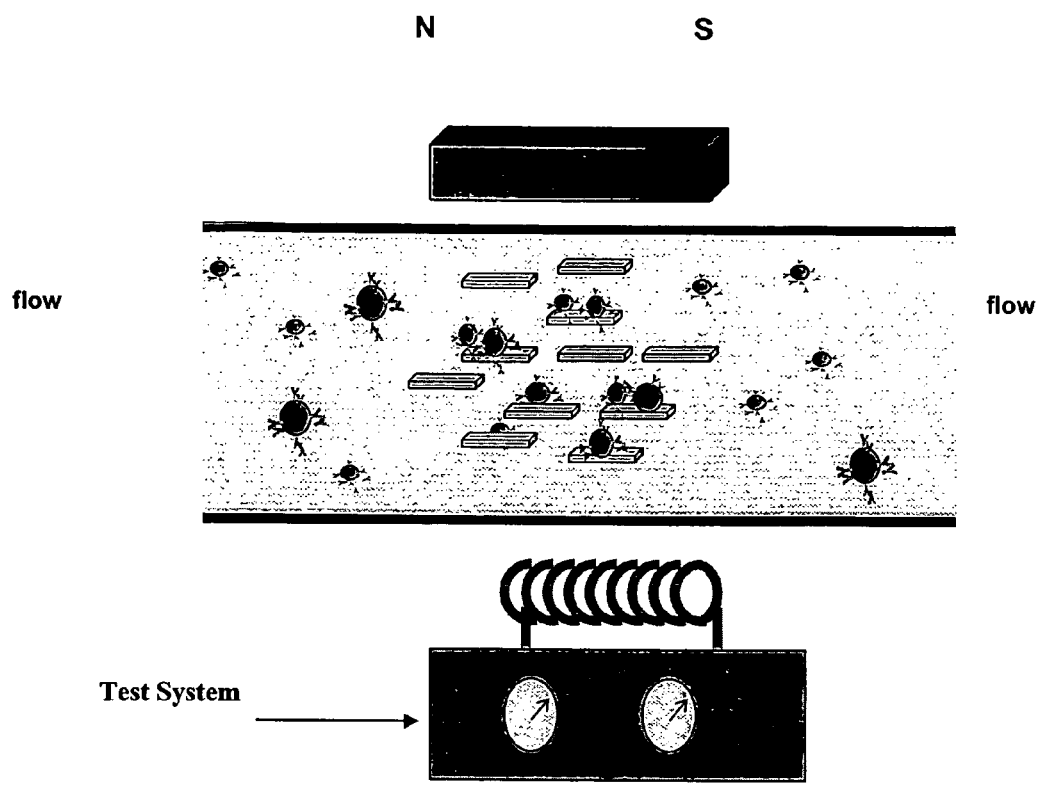

FIG. 25 shows a schematic of an isolation technique.

Figure 26:
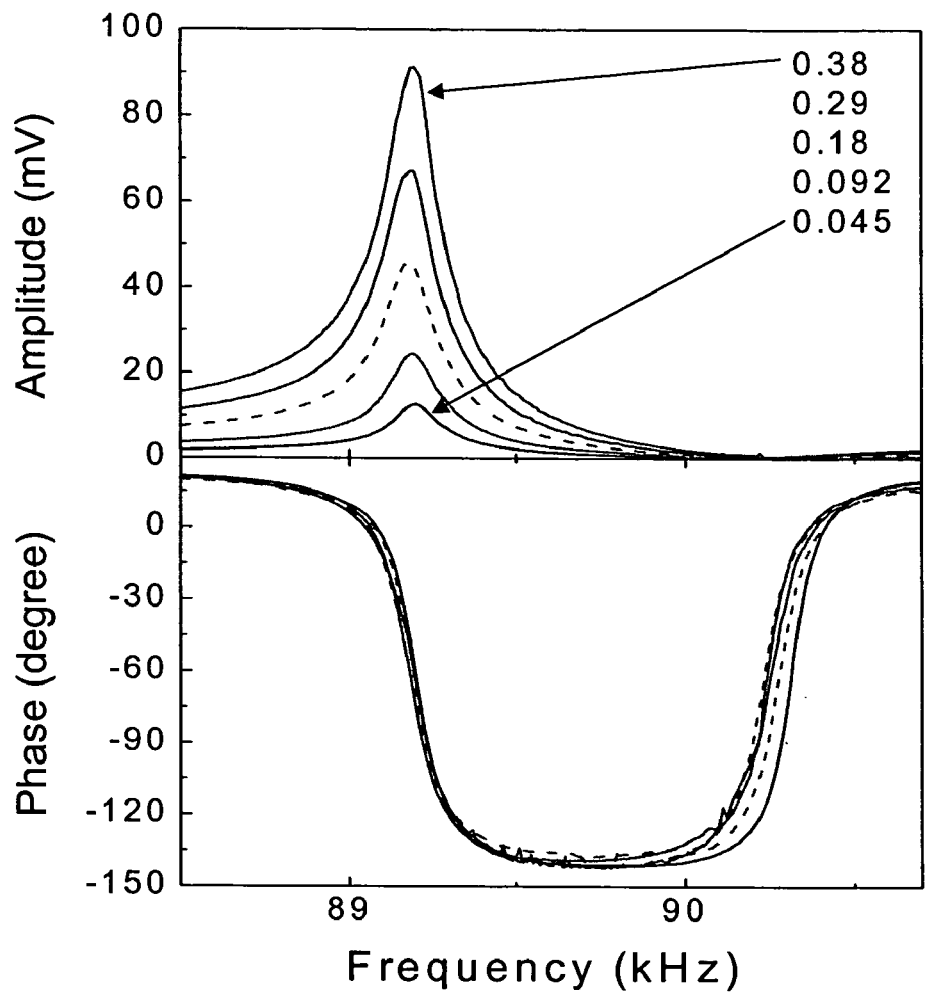

FIG. 26 shows the resonance behavior of an MSP under different driving fields from 0.045 (bottom line) to 0.38 gauss (top line), as indicated.

Figure 27:
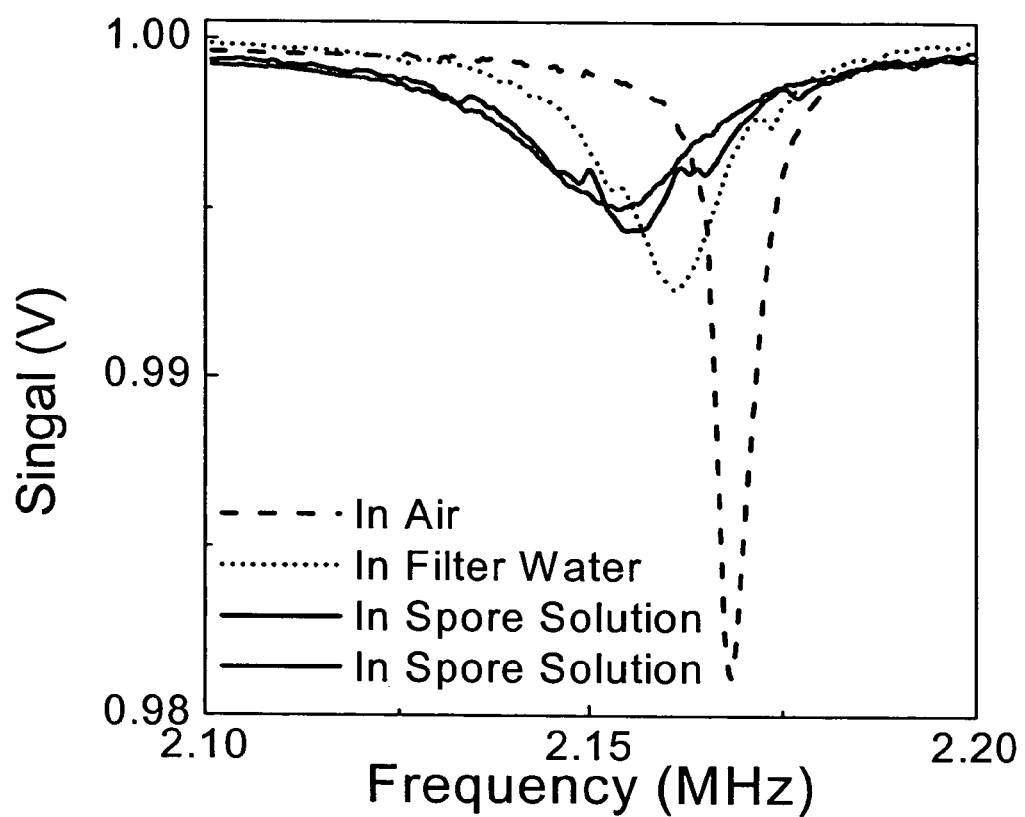

FIG. 27 shows the resonance behavior of an MSP-based biosensor in different media. Two curves obtained in sport solution represent results obtained at different times.

Figure 28:
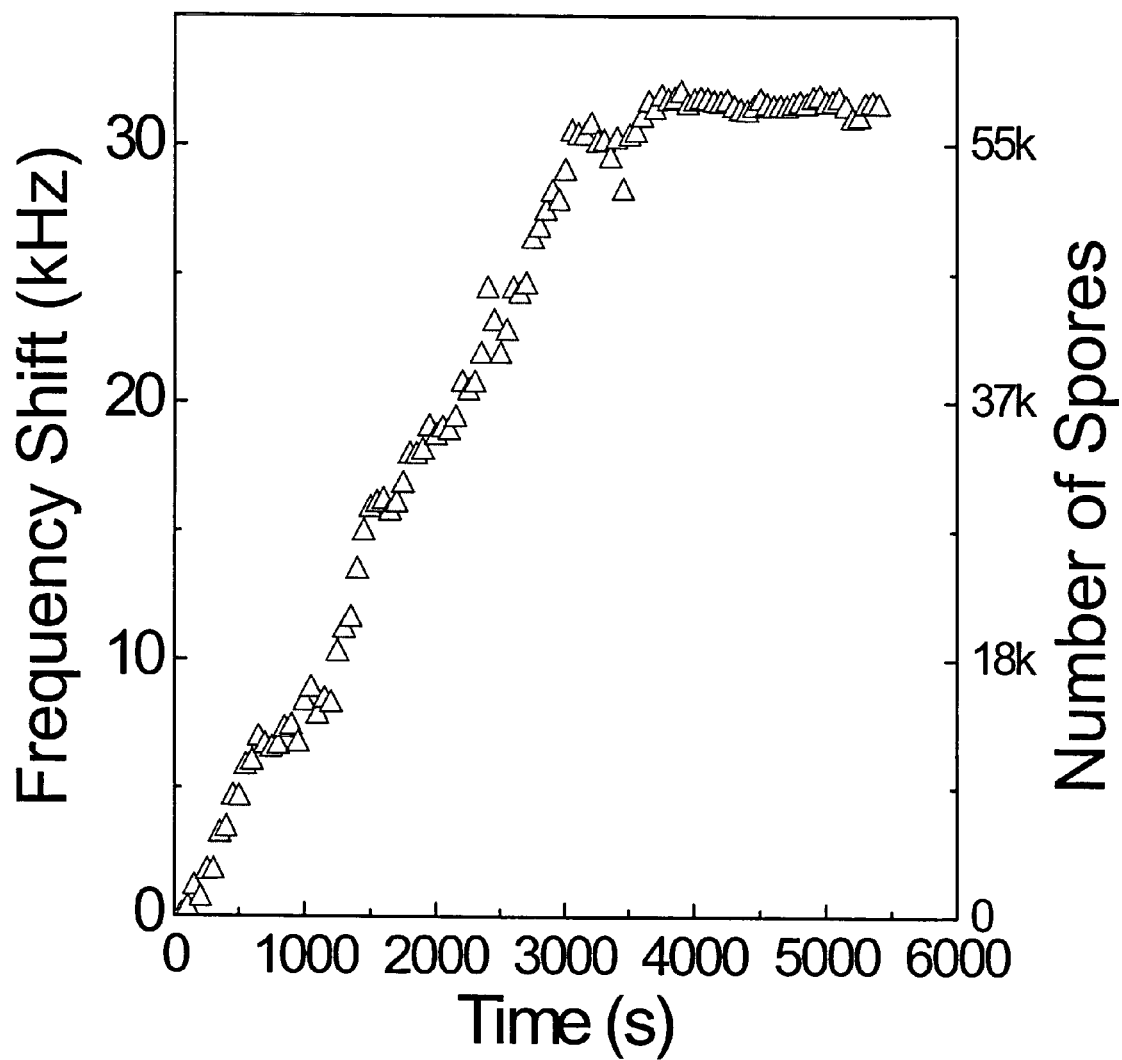

FIG. 28 shows the resonance frequency as a function of time for an MSP-based biosensor in spore solution. The number of spores (indicated on the right hand side of the figure) was calculated from the other experimentally-obtained values.

Figure 29:
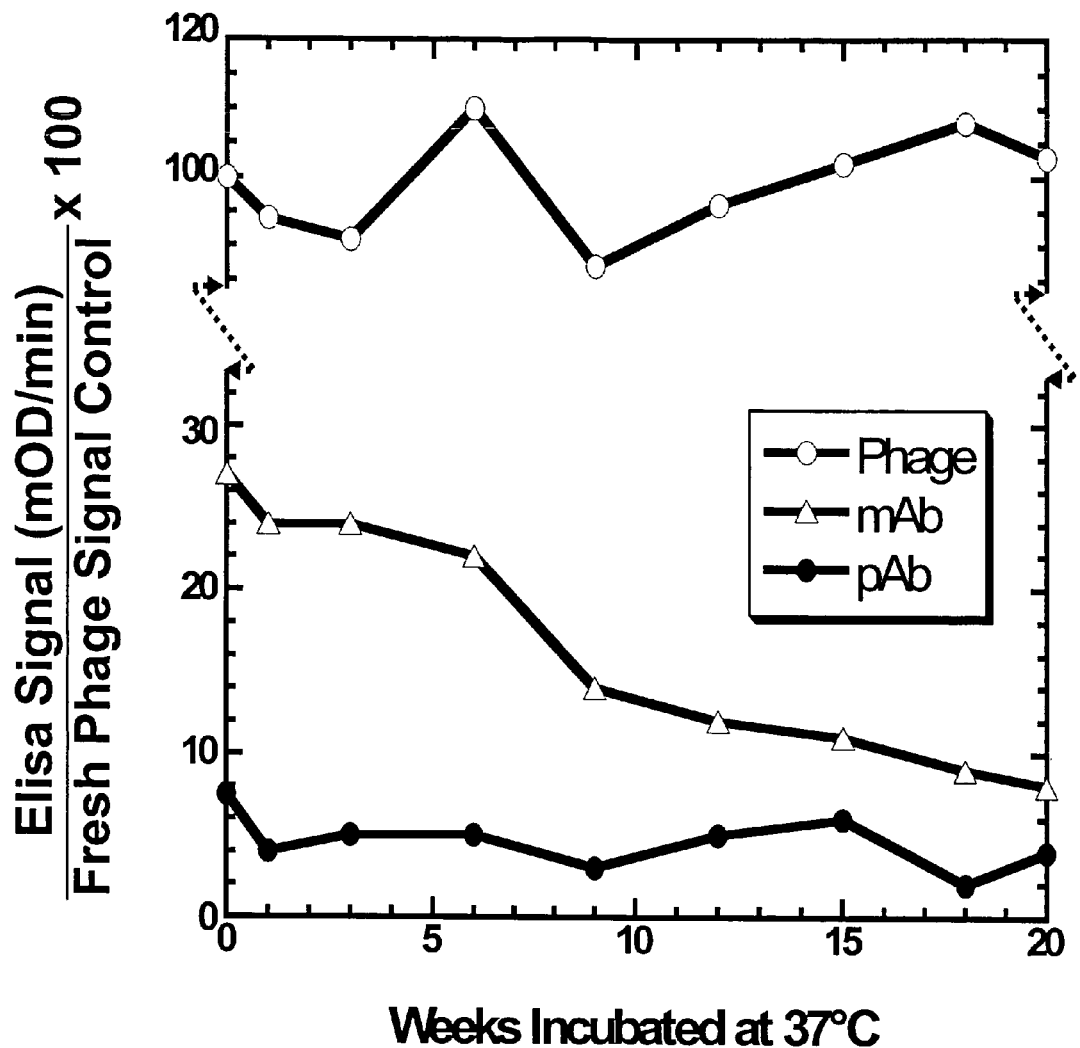

FIG. 29 shows a comparison of the stability of phage, monoclonal antibody (mAb) and polyclonal antibody (pAb) at 37° C. In contrast to the antibody binding, the phage binding shows no degradation.

Figure 30:
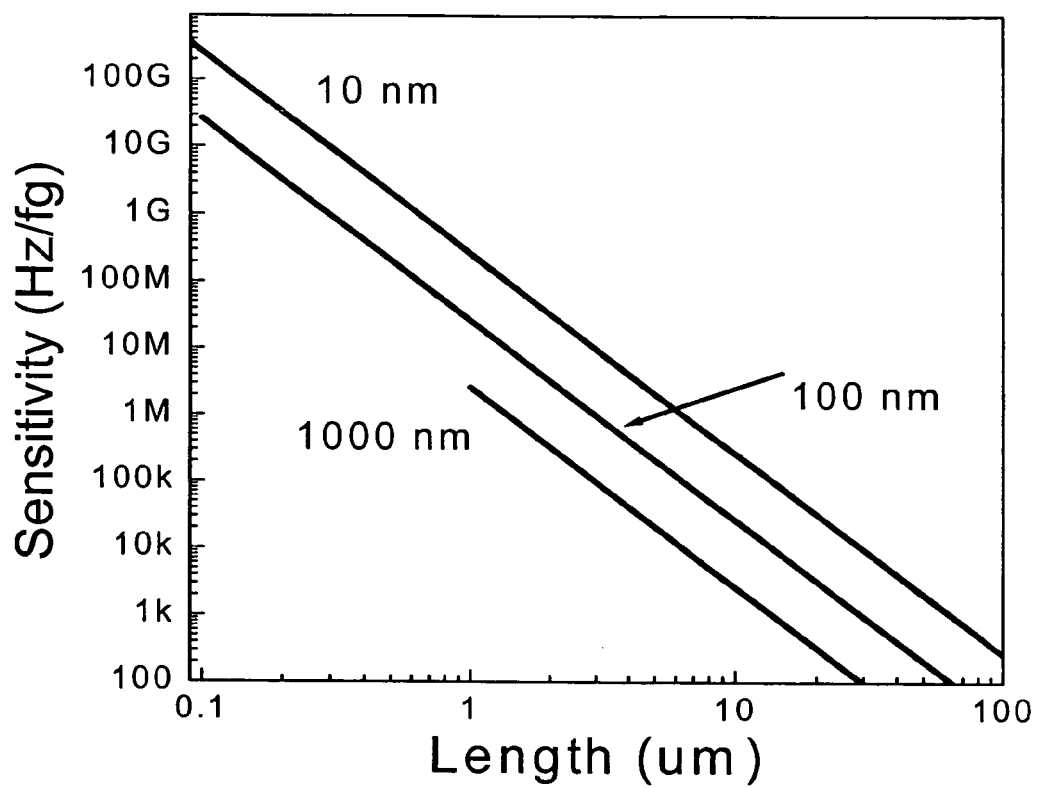

FIG. 30 shows the predicted sensitivities of MSPs as a function of length and thickness.

Figure 31:
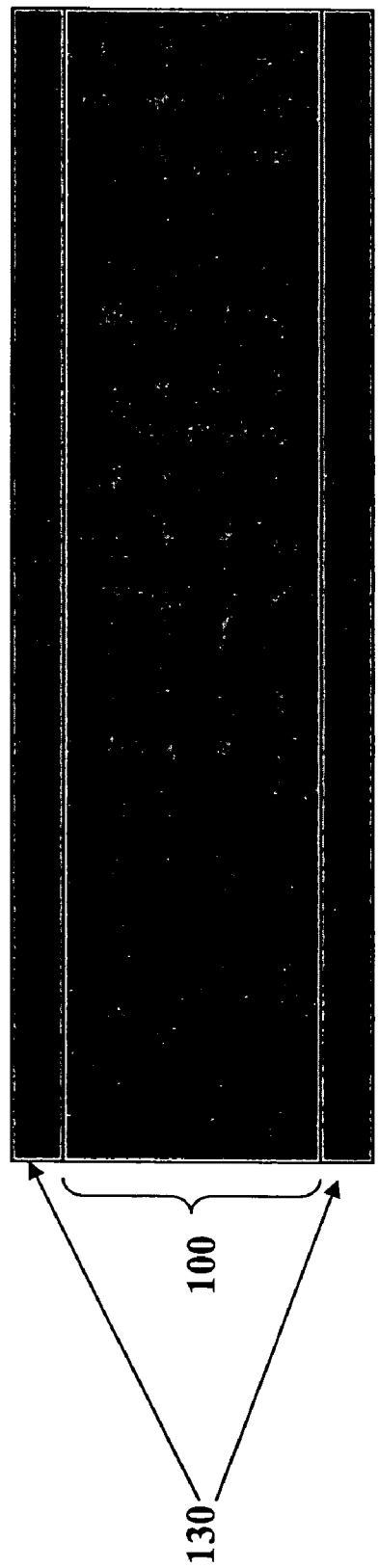

FIG. 31 shows a schematic of an embodiment of a magnetostrictive ligand sensor device (MLSD) of the present invention including a binding element applied to a magnetostrictive particle (MSP).

DETAILED DESCRIPTION OF THE INVENTION

Methods and compositions for identifying and/or evaluating one or more ligands are provided. In particular, magnetostrictive ligand sensor devices (MLSDs) are provided, as well as assays using MLSDs and sensor systems comprising MLSDs. The MLSD comprises magnetostrictive material coupled to at least one binding element. In some embodiments, the MLSD comprises a collection of at least two magnetostrictive particles ("MSPs") coupled to at least one binding element. "Magnetostrictive" as used herein refers to the ability of a material to transduce or convert magnetic energy to mechanical energy and vice versa; thus, magnetostrictive materials generate magnetic energy when mechanical strain is applied, or generate a mechanical strain when magnetic energy is applied. This reciprocal relationship provides a transduction capability that is used for both actuation and sensing devices. The magnetic energy may be generated by electrical current, for example, by sending a current through a wire conductor to generate a magnetic field.

The MLSD thus allows detection and characterization of interactions between a binding element and one or more ligands. In this manner, the MLSD provides an in vivo or in vitro assay that can be used to isolate and examine substances, including ligands, which bind to particular binding elements. In this manner, the MLSD provides an assay for the rapid discovery of small molecule ligands that specifically bind to binding agents such as, for example, peptides. Thus, MLSDs find use in many applications. For example, the MLSDs and assays of the invention are useful in the isolation and identification of peptide-specific molecules that can be used to target various compounds or molecules in gene and/or drug therapy protocols.

The present inventions now will be described more fully hereinafter with reference to the accompanying drawings, in which some but not all embodiments of the invention are shown. This invention may be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

FIG. 1 shows one embodiment of the sensor system of the present invention. A magnetostrictive particle (MSP) 100 is shown coupled to a binding element 130 to which are attached a number of target ligands 120 within a sample 400. The binding element 130 coupled to the MSP 100 is designed to bind selectively with the target ligands 120 such that the ligands become bound to the MSP as shown. FIG. 1 also shows a driver 200 which is configured to emit a varying magnetic field 140 that, in turn, induces a longitudinal oscillation and a resulting resonance response 150 from the MSP. Also shown is a measurement device 300 configured to detect the resonance response 150 of the MSP 100 and convert the detected resonance response 150 into a resonance frequency. Since the MSP 100 may be activated remotely by the magnetic fields 140, 150 emitted and received using frequency and/or time domain measurements by the driver 200 and measurement device 300, respectively, the MSP 100 may be released into a sample 400 in order to remotely identify and quantify target ligands 120 present therein.

In one advantageous embodiment of the present invention, the MSP 100 has a substantially strip-like or bar-like shape such that the driver 200 induces oscillation in the MSP 100 in its longitudinal vibration mode. In this embodiment, the MSP 100 is configured to exhibit a resonance response 150 in the form of a longitudinal oscillation, at a resonance frequency characteristic of the length and material composition of the MSP 100. The longitudinal oscillation of the MSP 100, in turn, produces a varying magnetic field 150 that oscillates at a characteristic resonance frequency that depends on the MSP size and associated material properties. For example, one skilled in the art will appreciate that for a generally rectangularly-shaped MSP 100, the characteristic resonance frequency of the longitudinal oscillation and corresponding varying magnetic field produced by an MSP having no additional mass load can be calculated using the following formula:

$$f_0 = \frac{1}{2L}\sqrt{\frac{E}{\rho(1-\sigma^2)}} \qquad (1)$$

where,

L=the length of the MSP;

E=Young's modulus of the MSP material;

ρ=density of the MSP material; and

σ=Poisson ratio of the MSP material.

MSPs may be constructed of commercially-available materials exhibiting magnetostrictive properties, such as, for example, Metglas® Solution 2826MB (Honeywell, Inc., Parsippany, N.J.). Other examples of commercially available magnetostrictive materials include Terfenol-D (Etrema Products, Inc., Ames, Iowa) and other materials from companies such as, for example, Dexter Magnetic Technologies (Elk Grove Village, Ill.).

As shown in FIG. 5, according to one advantageous embodiment, the MSP 100 may be coated with a coating 103 such as gold to facilitate fixation thereto of additional layers of the binding element such as, for example, the binding agent 110. Other coatings may also be used, such as, for example, Pt, Cr, Ti, Cu, and S. In other embodiments, the MSP coating 103 may further comprise a polymer or a monolayer of molecules 105, or a "coupling composition layer," suitable for binding and/or facilitating the attachment of binding agents 110. As shown in FIG. 31, a binding element 130 may also be used that does not comprise a binding agent.

The binding agent 110 used in the MLSD may include any binding agent suitable for binding to the target ligand 120 and may include, for instance: monoclonal antibodies, polyclonal antibodies, phages, DNA or RNA fragments, or combinations thereof. As shown in FIG. 5, some advantageous embodiments of a binding element may provide a coupling composition layer 105 to be interspersed between either the MSP 100 and the binding agent 110 or between a coating 103 (such as gold) and the binding element agent 110. The coupling composition layer 105 may comprise various substances configured to assist the attachment of binding agents to the MSP, such as, for instance, streptavidin, or biotinylated lipid layers. Alternatively, the binding agent 110 may be deposited directly on the surface of the MSP 100; appropriate techniques are known in the art. Thus, by "binding element" is intended any layers or coatings on the MSP; the binding element interacts with substances in the environment of the MSP and is changed or added to in some detectable way thereby. By "binding agent" is intended a component of a binding element which binds specifically to at least one ligand.

Thus, in other embodiments, as shown in FIG. 31, the binding element 130 coupled to the MSP 100 does not bind selectively to a target ligand but rather is a chemical entity such as a polymer that, for example, undergoes a detectable change due to its interaction with substances in its environment. For example, the binding element may be a polymer that undergoes an increase in weight under conditions of high humidity. A binding element may also undergo changes due to an interaction with chemicals such as an organic or inorganic chemical or chemical compound. Thus, for example, a binding element may be a polymer such as a pH-sensitive polymer, a humidity-sensitive polymer, or an enzyme-polymer composite (see, e.g., U.S. Pat. Nos. 6,393,921 and 6,397,661). By using various types of binding elements on individual MSPs or on different MSPs, the MLSD may be configured to detect and quantify a variety of different chemical and biological agents of various molecule and cell sizes present in small amounts in a relatively large sample. In some embodiments, a collection of MSPs is used; by "collection" is intended a group of at least two MSPs which may be the same type or different types of MSPs; i.e., the MSPs may differ in at least one characteristic such as, for example, their binding elements. In some embodiments of the sensor, a driver 200 is provided and configured to produce and apply a varying magnetic field 140 to the MSP 100 such that the MSP 100 exhibits longitudinal oscillations at a resonance frequency characteristic of the MSP 100. The driver 200 may be, for instance, a current-carrying Helmholtz coil suitable for producing a time-varying magnetic field configured to drive the resonator to oscillate at its resonance frequency in its longitudinal vibration mode. Therefore, in embodiments using strip-shaped MSPs, the longitudinal oscillations also produce a time-varying magnetic field 150 that oscillates at the resonance frequency of the MSP.

Thus, in some embodiments, the driver 200 is a coil having an electric current passing therethrough such as, for instance, a Helmholtz coil configured to produce a varying magnetic field suitable for driving a longitudinal oscillation and associated resonance response 150 in the resonator. The driver 200 of this embodiment may be arranged substantially near the sample 400 so as to exert the varying magnetic field 140 on the MSP 100 distributed therein. In addition, the driver may include a coil having turns configured to surround a specimen container such as the detection chambers 510, 520 or specimen archive chamber 525 shown in FIG. 4.

One skilled in the art will also appreciate that due to the magnetic nature of the MSPs 100, external magnetic fields produced by, for example, current-carrying coils and/or magnetic materials such as permanent magnets or electromagnets, may be used to remotely manipulate the MSPs 100 within the sample 400 such as, for example, a food sample or the body of a patient. As shown in FIG. 4, the sensor system and method of the present invention may further include coils for producing both constant and varying magnetic fields to allow for the remote control of the MSP 100 distributed within the sample 400. For instance, a guide coil with an electric current passing therethrough may produce a magnetic field suitable for remotely locating and guiding the MSP 100 within a sample 400. In other embodiments, other magnetic elements, such as for example, permanent magnets or electromagnets may be used to remotely orient the MSP 100 within a sample 400 located, for instance, in a pipeline as shown in FIG. 25. Further, a stirrer coil may be provided to produce a varying magnetic field to act upon the MSP 100 such that the MSP 100 may be distributed throughout a volume of the sample 400 so that small amounts of target ligand 120 unevenly distributed in the sample 400 are rendered detectable by the sensor system of the present invention. Other embodiments use magnetostrictive particles that are guided to a specific region of the human body; in such embodiments, the MSPs may be useful in evaluating local chemistry or conditions indicative of a disease.

The resonance response 150 of the MSP 100 exhibits a change as a result of ligands 120 binding to the binding element 130 of the MSP 100. The change may be characterized as, for example, a decrease in the resonance frequency of the resonance response as ligands 120 are bound to the binding element 130 of the MSP 100. A ligand 120 may be detected by comparing the resonance frequency of an MSP having no ligands attached with the resonance frequency of an MSP having ligands bound thereto.

FIG. 2 shows the resonance frequency of an MSP according to the present invention in terms of amplitude and frequency. A first resonance peak 101 of an MSP having no ligands (and thus no additional mass) attached occurs at a higher frequency and with greater amplitude than a second resonance peak 102 of the same MSP having the mass of the ligands attached. Thus, the presence of ligands in a specimen can be determined by identifying the presence of the downward frequency shift and reduced amplitude of the second resonance peak 102, which corresponds to the additional mass added to the MSP 100 as the ligand 120 binds to the binding agent 110 coupled to the surface of the MSP 100. In addition, the measurement device 300 may be configured to quantify the approximate number of ligands 120 bound to each MSP 100 by determining the magnitude of the frequency shift 103 from the first resonance peak 101 to the second resonance peak 102.

In order to detect very small amounts of the target particle in a given specimen sample 400, the shift in frequency resulting from only a small increase in mass is detectable by the measurement device 300 of the sensor system. As stated above, the resonance frequency of the first resonance peak 101 that characterizes an MSP 100 having no mass load is dependent only upon the inherent material characteristics of the MSP and the MSP's length. In addition, an MSP having a smaller length exhibits a greater mass-detection sensitivity as its unloaded mass is initially lower than an MSP having a greater length. For an MSP according to the present invention, the mass sensitivity ($S_m$) can be characterized in terms of change in frequency versus change in mass or:

$$S_m = -\frac{\Delta f}{\Delta m} = \frac{f_0}{2M} \qquad (2)$$

where,
 m=change in mass of the MSP (due to attachment of ligands);
 $\Delta f$=shift in resonance frequency of the MSP;
 $f_0$=characteristic resonance frequency of a MSP having no target particles bound thereto; and
 M=mass of a MSP having no target particles bound thereto.

Using the mass-sensitivity relationship above, and using the known initial mass and characteristic resonance frequency of the MSP 100, the change in mass (m) of the MSP 100 due to the binding of ligands 120 thereto, can be determined from the observed resonance frequency shift (102, 101) detected by the measurement device 300 of the present invention.

Using the sensitivity relationship of equation (2), the shift in the natural frequency ($\Delta f_0$) related to the mechanical load on the resonator may be expressed as:

$$\frac{\Delta f}{f_0} = -\frac{1}{2}\frac{m}{M} \qquad (3)$$

where m and M are the masses of the mechanical load and the resonator, respectively. (see, *IRE standard on Piezoelectric Crystals: Determination of the Elastic, Piezoelectric, and Dielectric constant—the electromechanical coupling factors*, Proc. IRE, 496, 764 (1958); Merhaut (1981), Chapter 2 *in Theory of Electroacoustics* (McGraw-Hill Inc., New York)). Thus, the mechanical load (m) on the resonator (i.e., the mass of the ligand bound to the binding element component of the MLSD) can be very easily determined by the change in the natural frequency using equation (3).

In detail, the process linking the frequency shift with the mechanical load is as follows. If the initial mass of the MSP 100 and the binding element(s) is $m_0$, one can find the initial natural frequency ($f_1$) of the MSP before any capture of ligands using $$\frac{f_1 - f_0}{f_0} = -\frac{1}{2}\frac{m_0}{M} \qquad (4)$$

If the ligands captured by the binding element layer have a mass of $\Delta m$, the natural frequency (f) of the MLSD becomes:

$$\frac{f_1 - f_0}{f_0} = -\frac{1}{2}\frac{m_0 + \Delta m}{M} \qquad (5)$$

Substituting equation (5) into equation (4), we obtain $$\Delta f = f - f_1 = -\frac{f_0}{2M}\Delta m \qquad (6)$$

Equation (6) indicates that $\Delta f$, the frequency shift for the MSP 100 due to the capture of target ligands 120 by the binding agent 110 (or change in a property of the binding element 130), is linearly dependent on the mass of the ligands captured and a constant $$\left(-\frac{f_0}{2M}\right)$$

that depends only on the MSP 100 and can be calibrated. Therefore, equation (6) links the natural frequency shift of the MSP 100 with the mass of ligands captured by the binding element.

Based on equations (2) and (6), the following factors influence the sensitivity of the MLSD: 1) the constant $$\frac{f_0}{2M}$$

that is dependent on the elastic properties of the alloy (see equation (1)) and the geometric parameters of the resonator; and 2) the resolution of the frequency in the characterization of the resonator behavior, which is strongly dependent on the sharpness of the resonator peak. Using equation (2) and/or equation (3), one skilled in the art will appreciate that the dimensions of the MSP are a very important factor affecting the sensitivity of biosensors having a common length (L), while the Young's modulus is a critical factor determining the dimensions of the resonator. The thinner the resonator is (and thus, the less initial mass (M)), the higher the value of $$\frac{f_0}{2M}.$$

Similarly, the higher the Young's modulus of the material, the smaller the resonator must be if the operating frequency is to remain fixed. Based on acoustic theory, it is known that the elastic loss, which determines the Q value of the resonator, is the major factor determining the peak shape of the oscillation. Based on this, a magnetostrictive alloy with a high Q-value (i.e., a smaller elastic loss) is favorable.

Also, using the relationships outlined by equation (2) above, one skilled in the art will appreciate that small changes in mass due to the binding of, for example, a single ligand 120 to the binding agent 110 on the MSP surface may be detectable by an MSP 100 having a small initial mass and a high Q-value. In some advantageous embodiments, the MSP length may be less than 100 μm which may allow for the detection of a target particle such as a single bacterium (weighing, for instance, less than 10 picograms). In other embodiments, the MSP length and mass may be tailored such that the MSP is better suited to detect and quantify target particles having a variety of sizes. One of skill in the art appreciates that in the performance of the methods of the invention, the order of steps may be varied where the end result is not affected or where the object of the invention is nevertheless accomplished.

According to one embodiment, as shown in FIG. 6, the measurement device 300 may include a pick-up coil 305 tuned to receive a time varying magnetic field, such as that produced by the MSP 100 of the present invention. The measurement device may also include a filter device 310 such as for instance, a notch filter, for eliminating extraneous frequencies known to be greater than or less than the frequency range of resonance and any anticipated frequency shift. One skilled in the art will appreciate that, in some embodiments, the measurement device may also include an amplifier 315 and analog-to-digital converter 318 for amplifying and conditioning the measured signal prior to further analysis as shown in FIG. 6. The measurement device 300 may also include a fast Fourier transform (FFT) device, in order to transform the incoming time-varying signal 150 from, for instance, the time domain, to the frequency domain, such that the resonance frequency peak is discernible in a plot of phase, amplitude, or impedance versus frequency, as shown in FIGS. 2 and 7. The measurement device may also include a memory unit 340 having a plurality of registers 345 configured to store the predicted resonance peak data for a plurality of MSPs 100. In this embodiment, the measurement device 300 may then also include a central processing unit 350 such as a personal computer or other data processing device, for comparing the predicted resonance peak data (such as, for example the first resonance peak 101 shown in FIG. 2) stored in the registers 345 of a memory module 340 to the incoming plot of the second resonance peak 102 (FIG. 2) produced by, for instance, the FFT 320. In some embodiments the measurement device may also include a display 350 for displaying either the comparative resonance peaks, or numerical data relating to the detection or quantification of the target ligands. Thus, the measurement device 300 and the included central processing unit are capable of utilizing a computer program product so as to automatically calculate the change in mass from the detected shift in resonance frequency. In yet another advantageous embodiment, the measurement device 300 may be further configured to determine from a pre-programmed list stored in the registers 345, the anticipated mass of the ligand 120 such that the approximate quantity of the ligands 120 bound to the MSP 100 may be calculated based on the detected shift in resonance frequency.

Regarding the measurement device 300 or receiver and the driver 200 of the present invention, one skilled in the art will appreciate that an AC magnetic field coupled with a DC magnetic field may employed to drive the resonator 100. The signal 150 emitted by the resonator 100 is also picked up by the measurement device 300, and the emitted signal at different frequencies may be determined and recorded. The relationship between the signal amplitude and the frequency may be used to determine the resonance frequency. One skilled in the art will also appreciate that at least two different driving techniques may be used: 1) a time-domain technique; and 2) a frequency domain technique. In the time-domain technique, a modulated magnetic field is used to drive the MSP 100 resonator. The time delay technique is used to characterize the emission 150 from the MSP 100. In the frequency-domain technique, a continuous field is employed to drive the MSP 100. The frequency of the driving field scans in a certain range while the amplitude of the field remains constant. A lock-in technique is used to characterize the amplitude and phase delay of the emission signal. Many lock-in amplifiers are commercially available and can be used for this purpose.

As shown in FIG. 3, multiple MSP types 100a, 100b, may be released into the sample 400, each MSP type having a different characteristic resonance response, for example, due to each MSP having different dimensions or having slightly different compositions. Further, each MSP type may have a binding element that includes a different binding agent 110a, 110b which binds a different corresponding target ligand 120a, 120b, or might include a different binding element 130 as depicted in FIG. 31. In these embodiments, each MSP type will exhibit a unique first resonance peak 101a, 101b, as shown in FIG. 3. In these embodiments, the MSPs may be coated with binding elements appropriate to their respective lengths and masses, such that the MSPs have adequate sensitivities to detect the mass of small amounts of the target ligands 120a, 120b to which their binding agents 110a, 110b correspond, or to detect small changes in their environment by detecting changes in a binding element 130.

In other embodiments, the measurement device 300 may be further configured to measure the magnitude of the change in resonance response in order to quantify the approximate number of target ligands 120 bound to the MSP 100. One skilled in the art will appreciate that the measurement device 300 may include a wireless receiver coil configured to remotely detect the varying magnetic field emitted by the MSP 100 and that the receiver coil may be operably engaged with a circuit, such as, for example, a peak detector circuit, such that the resonance response of the MSP 100 may be determined in terms of frequency and amplitude of the resonance response.

FIG. 4 shows another advantageous embodiment of the present invention wherein the sensor system is adapted to sample air from, for instance, an HVAC system, in order to determine if target particles 120, such as, for example, harmful biological agents are present therein. In this embodiment, filtered air samples are drawn into the sensor system and mixed with a liquid media to create a sample 400 for analysis. According to this embodiment, air is first directed through a filter 500 to remove particulate matter. The filtered air is then directed to an Air-to-Liquid concentrator 505. The concentrator may be a commercially available unit such as, for example, a COTS-SASS 2000 Air-To-Liquid Concentrator.

The resulting liquid sample 400 may then be directed to a first detection chamber 510, wherein magnetostrictive particle (MSP) MSPs 100 according to the present invention are located. A plurality of different MSP sizes and corresponding binding agents 110 attached thereto may be included in the first detection chamber 510 such that the first detection chamber may detect one or more types of target ligand(s) 120. Also, the MSPs 100 of the first detection chamber 510 may be held in place and/or stirred within the first detection chamber by a coil configured to produce a magnetic field for adjusting the positions of the MSPs within the first detection chamber. The coil may, for instance, include multiple wire turns that enclose the first detection chamber 510.

A control unit containing a driver coil 200 according to one embodiment of the present invention may then emit a varying magnetic field 140 in order to induce the relative resonance responses 150 of the MSPs 100 in the first detection chamber 510. The control unit may also include a measurement device 300 according to the present invention, such as, for instance, a coil for detecting changes in the resonance responses 150 of the MSPs 100 in the first detection chamber 510 such that the presence of one or more target ligands 120 may be detected.

A switch valve 515 may be located downstream from the first detection chamber 510, such that if no target ligands 120 are detected, the switch valve 515 may shunt the sample specimen 400 directly back through a modular filter 530 to remove all particulates from the sample specimen 400 and recycle the liquid media for use in a later target ligand detection sequence. Alternatively, if some of the MSPs 100 of the first detection chamber 510 exhibit a change in resonance response 150, the sample specimen 400 is passed through the switch valve 515 into a second detection chamber 520, where additional MSPs 100 corresponding to the MSP type for which a resonance change was observed in the first detection chamber 510 are released. The additional MSPs 100 released in the second detection chamber 520 may be provided with binding agents 110 corresponding only to the target ligand 120 detected in the first detection chamber 510. Also, the MSPs 100 released in the second detection chamber 520 may be of a smaller initial mass and length so as to provide greater mass-sensitivity such that the approximate mass of individual target ligands 120 may be quantified. In this manner, the second detection chamber 520 serves to confirm the identity of the target ligands 120 preliminarily identified in the first detection chamber 510 by sizing the ligands 120.

Ligands 120 bound to the MSPs 100 in both the first and second detection chambers 510, 520 may further be collected in a specimen archive chamber 525 located downstream from the second detection chamber 520. The MSPs 100 and the ligands bound thereto 120 may be held in the specimen archive chamber 525 by an additional coil providing a magnetic field for remotely manipulating the MSPs 100. The coil may, for instance, include multiple wire turns that enclose the specimen archive chamber 525. Finally, after the bound MSPs 100 are archived in the specimen archive chamber, the remaining fluid media can be passed through the modular filter 530 and recycled for use in a later target ligand 120 detection sequence.

There are several advantages of magnetostrictive sensors over other sensors in the art. First, magnetostrictive materials can be actuated and read by remote magnetic fields, eliminating the need for attachment of the device to metallized electrodes and allowing the use of remotely interrogable, wireless devices. This eliminates the need for passivating layers to protect the electronics from liquid environments and also simplifies device fabrication through the minimization of steps. See, for example, Hristoforou (2003) *Measurement Science & Technology* 14:R15-R47. Further, remotely interrogable, wireless sensors can be used in applications unsuitable for wired devices. For example, an MLSD can be placed within food packages for continuous monitoring of foodborne pathogens. Secondly, the coupling of magneto- and mechanical properties provides high quality of detection and improves sensitivity of sensing devices. Finally, the absence of actuation and conditioning electronics on the device not only decreases the complexity of microfabrication but also increases the reliability and integrity of the device. By "magnetic field," as used herein, is intended that the field is magnetic and/or electromagnetic. By "magnetostrictive," as used herein, is intended that a device or composition has magnetostrictive and/or piezomagnetic properties.

The magnetostrictive particle (MSP) component of MLSDs comprises at least one magnetostrictive material or alloy which is provided in various forms. Thus, the MSP may comprise a single piece of magnetostrictive alloy or a multi-layered construction of magnetostrictive alloys or it may comprise a collection of particles of at least one magnetostrictive alloy. The magnetostrictive alloy may be in various shapes, such as a wire or a ribbon, and may comprise several different layers of different materials, such as for example, a layer of magnetostrictive material and a layer of piezoelectric material, or two different layers of magnetostrictive materials. See, for example, Michelena et al. (2002) *J. Magnetism and Magnetic Materials* 242-245:1160-1162. Where the sensor device comprises a collection of particles, the magnetostrictive particles may range in size from a few nanometers to larger particles of a few centimeters or more in length.

Characteristics of the magnetostrictive particles (MSPs), including the resonance frequency of the MSP, can be modified by altering parameters such as the composition of the magnetostrictive alloy(s), heat treatment, microstructure, and particle dimensions. See, e.g., Desnenko and Fertman (2001) *Sensors and Actuators A: Physical* 91:120-122; Chiriac et al. (2001) *Sensors and Actuators A: Physical* 91:223-225; Duenas et al. (1997), "Magnetostrictive composite material systems analytical/experimental," presented at *Proceedings of the 1996 MRS Fall Symposium* (Dec. 2-5, 1996, Boston, Mass.). It is known in the art that particles having different sizes, compositions, and processing can affect the behavior of materials containing them. Thus, each type of magnetostrictive particle will have its own characteristic resonance frequency.

Parameters can be chosen to create a magnetostrictive particle so that the binding of a ligand will cause a detectable and substantial shift in the resonance characteristics of the particles, and those of skill in the art can readily adjust parameters to produce suitable particles for a particular embodiment of the invention. In some embodiments, particle morphologies that have high surface to volume ratios are used. Selection of parameters is based in part on the following principles: 1) magnetostrictive alloys with lower densities display increased sensitivity to mass; 2) alloys with higher Q values (as defined below) at the operating frequency range display increased resolution for determining resonance frequency; 3) sensors made from alloys with high magnetostrictive coefficients and high magnetic permittivity display increased signal amplitude. The selection process involves choosing a suitable alloy or alloys based on these principles; one of skill in the art is able to select a suitable alloy or alloys for an embodiment by simultaneously applying these and other principles in view of the requirements of a particular embodiment. Thus, for a particular operating frequency range, one of skill will be able to determine an alloy having a desirable Q value of at least about 5, 10, 25, 50, 60, 70, 80, 90, 100, 110, 120, 150, 200, 300, 400, 500, 600, 800, 1000, 2000, 3000, 4000, or over 6000, or having a Q value within a range the endpoints of which are specified in the preceding list (e.g., having a Q value between 60 and 500).

Magnetostrictive materials and devices are known in the art. See, for example, Wang et al. (2003) *Finite Elements in Analysis and Design* 39:765-782; Pulliam et al. (2002) "Recent advances in magnetostrictive particulate composite technology," presented at *Smart Structures and Materials 2002: Industrial and Commercial Applications of Smart Structures Technologies*, Mar. 18-21, 2002, San Diego, Calif.; Hudson et al. (2000) "Dynamic magneto-mechanical properties of epoxy-bonded Terfenol-D composites," *Sensors and Actuators, A: Physical, the $2^{nd}$ European Magnetic Sensors and Actuators Conference* (EMSA '98), Jul. 13-Jul. 15, 1998, vol. 81, pp. 294-296; Anjanappa and Wu (1997) *Smart Materials and Structures* 6:393-402; Anjanappa and Wu (1997), "Experimental study of the macroscopic behavior of magnetostrictive particulate actuators," presented at *Smart Structures and Materials 1997: Smart Structures and Integrated Systems* (Mar. 3-6, 1997, San Diego, Calif.); Anjanappa and Wu (1996), "Modeling of embedded magnetostrictive particulate actuators," presented at *Smart Structures and Materials 1996: Smart Structures and Materials* (Feb. 26-29, 1996, San Diego, Calif.); Mohie-Eldin and Gunther (1993) *J. of Magnetism and Magnetic Materials* 127:346-358; U.S. Pat. No. 6,359,444; Nakai et al. (2002) *J. of Magnetism and Magnetic Materials* 242-245:1142-1145.

Different types of magnetostrictive particles can be coupled to (i.e., coated with) the same binding element or with different binding elements, and many different types of magnetostrictive particles can be exposed to a sample simultaneously. Thus, magnetostrictive particles are coated or impregnated with the binding element, or the binding element is chemically or physically attached to the surface of the particles. Magnetostrictive particles may be coated with a binding element on one surface or all surfaces. The particles may be coated with different binding elements on different surfaces, and may be coated in selected areas to enhance performance characteristics. Thus, particles may be coated with 1, 2, 3, 4, 5, or 6 or more different binding elements, and each binding element can comprise 1, 2, 3, 4, 5, 6, 7, 8, 9, or 10 or more different binding agents. Blocking agents, such as bovine serum albumin (BSA), may also be applied to the particles or the MLSD of the invention to block uncoated surfaces and reduce nonspecific binding.

The magnetostrictive particles may be mixed or distributed through a sample to be tested. For example, the magnetostrictive particles may be added to a liquid or gaseous sample, or to a solid sample. The small size and large number of particles used in such embodiments greatly increases the probability of binding to a ligand, thereby increasing sensitivity and reducing the time needed for ligand detection. In addition, the use of particles allows the sensor to be brought to the analyte or sample, whereas in other sensor conformations such as a disk or plate, the analyte must be brought to the sensor. Due to the magnetic characteristics of the magnetostrictive material, magnetic stirring can be used to enhance mixing of particles and sample. Some magnetostrictive particles can be reserved for use as a standard.

The sizes of the particles can be adjusted for particular embodiments, so that the sizes of particles used can have a thickness between about 10 nanometers and about 200 micrometers, a width between about 100 nanometers and about 5000 micrometers, and a length between about 200 nanometers and about 30,000 micrometers such that the particle is bar-like or tube-like in shape (i.e., a "strip"). The terms "thickness," "width," and "length" here are used for convenience rather than as limitations. Thus, it is understood that the particles may have one dimension that is between about 1 nanometer and about 2000 micrometers, a second dimension that is between about 50 nanometers and about 5,000 micrometers, and a third dimension that is between about 50 nanometers and about 30,000 micrometers. Particles may also have a first, second, and third dimension that are identical and are between about 50 nanometers and about 30,000 micrometers. Thus, particles may have a first, second, and/or third dimension that is about 1, 5, 10, 15, 20, 25, 30, 35, 40, 45, or 50 nanometers, or about 60, 70, 80, 90, 100, 110, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, or 980 nanometers, or about 1, 2, 5, 10, 20, 30, 40, 50, 60, 70, 80, 90, 100, 200, 300, 400, 600, or 800 micrometers, or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 millimeters. Particles may also have dimensions that fall within a range with an upper and lower bound selected from the preceding list. Particles may have any shape, such as, for example, strip-like, bar-like, tube-like, or spherical. It will be appreciated by those of skill in the art that the particle surfaces may have various morphologies; thus, for example, a particle surface may be rounded, planar, or irregular. Particle edges may vary; that is, a particle edge may be straight, curved, or irregular. Particles may be used in solution or on a surface, or may be provided in a cantilever, bridge, or membrane form.

Where the magnetostrictive sensor device comprises a collection of particles, the particles can be concentrated, separated, and/or collected from the sample after exposure to the sample using a magnetic field. Optionally, a reagent may be added to react with the bound ligand to affect its properties, e.g., to increase the mass of the ligand. Ligands can then be isolated from the sensor device and further analyzed for identification.

As shown in FIG. 1, MLSDs comprising MSPs 100 may be analyzed by using a driving magnetic field emitted by, for instance, a driving coil 200 to place the magnetostrictive particles 100 into resonance. As shown in FIG. 2, MSPs that are not bound to a target ligand 120 will have a characteristic resonance frequency 101. Binding of target ligand to an MSP will cause the resonance frequency of that particle to shift and a second peak 102 will appear at a different frequency as diagrammed in FIGS. 2 and 9. This frequency shift can be a result of various phenomena, including, for example, a change in mass, density, or viscoelastic or anelastic properties as well as the result of a chemical or biological reaction. Any phenomenon that results in a detectable alteration in the resonance characteristics of the magnetostrictive particles may be monitored. In some embodiments, the amount of the frequency shift will be related to the mass of the attached target ligand 120. When many particles are evaluated by a frequency scan, an MSP 100 with bound target ligand 120 will shift its resonance frequency as shown in FIG. 9. In some embodiments, a collection of particles with very similar or nearly identical resonance frequencies is used; the binding of ligand to at least one such particle can be detected by the frequency shift. In such embodiments, the resonance frequencies of the particles can vary by less than 0.001%, 0.005%, 0.01%, 0.05%, 0.1%, 0.5%, 1%, 2%, 3%, 4%, 5%, 6%, 7%, 8%, 9%, 10%, 12%, 14%, 16%, 18%, 20%, or 22% or more.

If the sensor device comprises more than one type of MSP 100, such as in the first detection chamber 510 of the embodiment shown in FIG. 4, the known characteristic resonance frequencies of the different MSP types can be analyzed for the appearance of new peaks resulting from the binding of ligand, as shown in FIGS. 3 and 10. Such analysis may be simultaneous or sequential. In this manner, a sample can be analyzed simultaneously for the presence of multiple ligands. For example, a food or water sample can be analyzed for the presence of both *Salmonella* bacteria and botulinum toxin.

The MLSDs of the invention are superior to devices previously known in the art. Acoustic wave (AW) devices are being widely investigated by researchers at both universities and national laboratories as potential sensing platforms to detect a wide variety of chemical and physical processes. See Ballantine, et al. (1997) *Acoustic wave sensors: Theory, design, and physical-chemical applications* (Academic Press, New York). These devices offer high-resolution monitoring of the accumulation of mass upon one of the MSP surfaces. Among the AW devices tested, the thickness shear mode (TSM) resonator has met with the greatest commercial success in applications such as plating thickness monitors. Other AW devices being investigated as mass sensors include surface acoustic wave (SAW), flexural plate wave (FPW) and microcantilever sensor (MCS) as shown in Table 2.

The operating principle of all these platforms is the same: a change in the mass load on the sensor shifts the resonance frequency, as shown generally in FIG. 8. Thus, the mass load can be determined by measuring the shift in resonance frequency. Comparisons between the various AW sensors are given in several review articles (See Thundat (1997) "Microcantilever sensors," *Microscale Thermophysical Engineering* 1:185-199, Ward and Buttry (1990) "In situ interfacial mass detection with piezoelectric transducers," *Science* 249:1000-1007, Grate et al. (1993) "Acoustic wave microsensors—Part I," *Analytical Chemistry* 65(21):940A-948A, Raiteri et al. (2001) "Micromechanical cantilever-based biosensors," *Sensors and Actuators B* 79:115-126, and Thundat et al. (1995) "Detection of mercury vapor using resonating microcantilevers," *Appl. Phys. Lett.*, 66:1695.)

Both normalized mass sensitivity ($S'_m$, used for Thickness Shear Mode (TSM), Flexural Plate Wave (FPW) and Surface Acoustic Wave (SAW) sensors) and mass-detection sensitivity ($S_m$, used for Magnetostrictive Particles (MSPs) and Microcantilever Sensors (MCS)) have been introduced as shown in equations (7) and (8) respectively:

$$S'_m = -\frac{1}{f_0}\frac{df}{dm'} \quad (7)$$

$$S_m = -\frac{df}{dm} \quad (8)$$

where m=the mass of the load and m' is the surface density. Using these equations, the sensitivities of these devices can be compared. Table 1 shows the normalized mass sensitivity of various sensors; the relative advantages of the MSPs of the present invention are evident.

TABLE 1

Normalized mass sensitivity ($S'_m$) of various acoustic devices

| Device | $f_0$ (MHz) | $S'_m$ (cm²/g) | Thickness |
|---|---|---|---|
| Magnetostrictive Particles (MSP) | 1.0–100 | 6329 | 0.1 µm |
|  | 0.10~10 | 633 | 1 µm |
|  | 0.02~~1 | 63 | 10 µm |
| Microcantilever Sensor (MCS) | 0.02~~5 | 10~1000 |  |
| Flexural Plate Wave (FPW) | 2.6 | 951 | ~1 µm |
| Surface Acoustic Wave (SAW) | 112 | 151 |  |
| Bulk Wave (TSM Microbalance) | 6 | 14 | ~278 µm |

The data for MCS are only an approximation since the mass load is not uniformly distributed. In general, a mass load attached at the tip of the cantilever results in the highest sensitivity. See Thundat (1997) "Microcantilever sensors," *Microscale Thermophysical Engineering*, 1:185-199. The data in Table 1 clearly indicate that the $S'_m$ of MSPs proposed in this project is higher than that of MCS and FPW, which exhibit the highest sensitivity among existing AW devices. It should be noted that the $S'_m$ defined in equation (7) is interpreted as the fractional change in resonance frequency due to the addition of a mass per unit area on the surface of the sensor. That is, the minimum detectable mass is dependent on the $S'_m$ and the size of the active area of the sensor. For the same $S'_m$, a smaller active area means a smaller absolute mass sensitivity. That is why it is MCS rather than the FPW that is very attractive for sensing small amounts of mass, such as a single bacterium or spore. Recently Ilic has demonstrated the detection of a single bacterium (~1 pg) using a silicon based MCS. See Ilic et al. (2001) *J. Vac. Sci. Technol.* 19(6):2858-2828, entitled "Single cell detection with micromechanical oscillators."

Design of Magnetostrictive Particles. Magnetostrictive particles (MSPs) for use as an MSP in the MLSDs of the invention may be different shapes, such as strip-like, bar-like, and tube-like. In the design, the resonance mode will be the one with the lowest mode frequency. For example, for strip-like particles, the resonance mode is length-vibration. The fundamental resonance frequency of a bar, or strip-like MSP can be expressed as shown in equation (1) above.

Based on equation (1), the resonance frequency of MSPs made of Metglas 2826 is predicted as shown in FIG. 21 using the material properties given in Table 2.

TABLE 2

Properties of Metglas ® solution 2826 MB

| Physical Properties (Unit) | Value |
|---|---|
| Density (g/cc) | 7.9 |
| Elastic modulus (GPa) | 100~110 |
| Continuous service temperature (° C.) | 125 |
| Curie temperature (° C.) | 353 |
| Electrical resistivity (µΩ-cm) | 138 |
| Saturation magnetostriction (ppm) | 12 |
| Maximum DC permeability (µ) |  |
| Annealed | 800,000 |
| As cast | >50,000 |

The resonance frequency of different MSPs was measured; the results are shown in FIG. 21. Clearly, the experimental data match the theoretical predictions and MSP sensors smaller than 100 µm in length have been fabricated and tested.

Sensitivity of the MSP: If the mass load is uniformly distributed on the surface of an MSP, the mass-detection sensitivity of an MSP can be expressed as equation (2) above.

FIG. 22 compares the sensitivity of MSPs with that of microcantilever devices. In FIG. 22, the solid line represents theoretical predictions of $S_m$ and the open circles represent experimental results obtained on MSPs. The experiments were conducted using MSPs with different thicknesses and widths. The experimental data were converted to MSPs with a thickness of 1 µm and width of one tenth of its length. To obtain the theoretical predictions, the width of the MSP was assumed to be one tenth of its length, and a thickness of 1 µm and a density of $7.9 \times 10^3$ kg/m³ were used. In the experiments, the mass was changed by sputtering a gold layer onto the surface of the MSP. The results shown in FIG. 22 demonstrate that the experimentally measured sensitivity of MSPs is consistent with theoretical calculations.

For comparison, data from microcantilevers with different sizes and made of different materials are also presented in FIG. 22 as solid squares. See, the following references for data shown in FIG. 22: Ilic et al. (2000) "Mechanical resonant immunospecific biological detector," *Appl. Phys. Lett.* 77:450, Ilic et al. (2001) "Single cell detection with micromechanical oscillators," *J. Vac. Sci. Technol.* 19(6):2858-2828, Yi et al. (2002) "Effect of length, width, and mode on the mass detection sensitivity of piezoelectric unimorph cantilevers," *J. App. Phys.* 91:1680-1686, Yi et al. (2003) "In situ cell detection using piezoelectric lead zirconate titanate-stainless steel cantilevers," *J. App. Phys.* 93:619-625, Shih et al. (2001) "Simultaneous liquid viscosity and density determination with piezoelectric unimorph cantilevers," *J. App. Phys.* 89(2):1497, Thundat (1997) "Microcantilever sensors," *Microscale Thermophysical Engineering* 1:185-199, and Thundat et al. (1995) "Detection of mercury vapor using resonating microcantilevers," *Appl. Phys. Lett.* 66:1695.

Data from both silicon-based microcantilevers and piezoelectric-based cantilevers are included. The theoretical relationship between length and sensitivity for microcantilevers (dashed line) was drawn by eye based on the data from different microcantilevers. The $S_m$ of 7.1 kHz/pg and 1.1 kHz/pg were obtained from cantilevers with a length of 15 and 25 μm, respectively, where the thickness of both microcantilevers was the same, 0.32 pm. See Ilic et al. (2001) "Single cell detection with micromechanical oscillators," *J. Vac. Sci. Tech.* 19(6):2858-2828. It was reported that these two microcantilevers have the ability to detect a single bacterium (*E. coli* O157:H7) cell which weighs about 0.7 pg. Based on the data in FIG. 22, one can find that an MSP with a length close to 100 μm and a thickness of 1 μm has the same sensitivity. Clearly, the sensitivity ($S_m$) of MSPs is more than two orders of amplitude better than that of microcantilevers for devices of the same length.

Factors affecting sensitivity and resonance frequency: It should be noted that neither $S'_m$ (normalized mass sensitivity) nor $S_m$ (mass-detection sensitivity) completely describes the performance of an AW biosensor. The sensitivities defined above only show the change in resonance frequency due to a mass load. The ability to determine the resonance frequency accurately also affects overall device mass sensitivity.

Q-Values: The quality merit factor (Q value) is defined as the ratio of the energy stored in the resonant structure to the total energy losses per oscillation cycle. The Q value is defined as the ratio of resonance frequency to the width of the loss peak (Δf as defined below). The resonance frequency is the frequency of maximum loss, while the width of the loss peak (Δf) was determined as the width at maximum loss divided by $\sqrt{2}$ as shown in FIG. 23; results are shown in FIG. 24. A reference AW device can be used to monitor and correct for changes in the analyte environment, such as viscosity change and temperature, which might affect resonance frequency and resultant Q value determinations. A higher Q value means a sharper resonance peak and hence a more accurate determination of the resonance frequency. Therefore, it is desirable to have a sensor platform with a high Q value.

Viscous damping: In a viscous environment such as air or liquid, all AW devices suffer from the damping effects of media on the oscillatory behavior of the device. The effect of viscous damping is observed by the decrease in the Q value and the resonance frequency. Although MCSs provide high mass sensitivity compared to other AW devices, MCSs suffer from a low Q value that limits applications of MCS. For example, most microcantilevers exhibit a Q value of about 30-50 when operated in air. See also, Ilic et al. (2000)"Mechanical resonant immunospecific biological detector," *Appl. Phys. Lett.* 77:450 and Thundat (1997) "*Microcantilever sensors,*" *Microscale Thermophysical Engineering* 1: 185-199. That is why a mass-detection sensitivity of about 1 kHz/pg is required to identify a single *E. coli* O157:H7 cell (~0.7 pg). See also, Ilic et al. (2001) "Single cell detection with micromechanical oscillators," *J. Vac. Sci. Tech.* 19(6):2858-2828. When the cantilever is operated in water, the Q value is usually less than 10, which makes it difficult to conduct MCS measurements in liquids.

While a vacuum is the preferred environment in order to maximize sensitivity, conducting measurements in a vacuum is neither convenient nor practical for a portable biosensing detection system. In the development of MCS, much effort has been directed to increasing the Q value of the cantilever. One approach has been to expose the sensing surface to the target analyte followed by drying the microcantilever before making the measurements in either air or vacuum. See also, Ilic et al. (2000) "Mechanical resonant immunospecific biological detector," *Appl. Phys. Lett.*, 77:450 and Ilic et al. (2001) "Single cell detection with micromechanical oscillators," *J. Vac. Sci. Tech.* 19(6):2858-2828. Another approach has been to submerge only the tip of the cantilever to reduce viscous damping effects. See also, Yi et al. (2002) "Effect of length, width, and mode on the mass detection sensitivity of piezoelectric unimorph cantilevers," *J. App. Phys.* 91:1680-1686 and Yi et al. (2003) "In situ cell detection using piezoelectric lead zirconate titanate-stainless steel cantilevers," *J. App. Phys.* 93:619-625. Neither of these techniques solves the problem of reduced Q value, although they can provide a "work-around" for the problem. Several methods that rely on an automatic feedback system have been proposed to control the Q value. See also, Mertz et al. (1993) "Regulation of a microcantilever response by force feedback," *Appl. Phys. Lett.* 62:2344; Mehta et al. (2001) "Manipulation and controlled amplification of Brownian motion of microcantilever sensors," *Appl. Phys. Lett.* 78:1637; Muralidharan et al. (2001) "Analysis of amplification of thermal vibrations of a microcantilever," *J. App. Phys.* 89:4587; and Passian et al. (2002) "Dynamics of self-driven microcantilevers," *J. App. Phys.* 91:4693. The damping effect (reduction in Q value) on a device depends not only on the viscosity of the media, but also the structure and vibration mode of the AW device.

In order to evaluate the performance of MSPs, the Q value of MSPs in air and liquid was experimentally determined for strip-like MSPs with a thickness of 15 μm. For determining the Q value of MSPs, the method of Shih et al. ((2001) *J. App. Phys.* 89(2):1497) was used. In addition, a reference AW device can be used to monitor and correct for changes in the analyte environment, such as viscosity change and temperature, which might affect resonance frequency and resultant Q value determinations. The comparative Q-value results for MSPs in air and water are shown in FIG. 24.

The data presented in FIG. 24 clearly show that MSPs exhibit a much higher Q value than microcantilevers in both air and water. The MSPs can exhibit a Q value of several hundreds in air and a Q value close to or above one hundred in water. MSPs with uniform dimensions would be expected to have even higher Q values. For example, the frequency response of the MSP shown in FIG. 23 shows that the MSP characterized has a Q value of more than 1000. However, there are certain applications for which MCSs are better suited, as will be appreciated by those of skill in the art.

Resonance frequency may be affected by various other factors, including: 1) permanent deformation of a MSP that alters its resonance frequency; 2) adhesion of an MSP to the wall of the detection container; and 3) nonspecific binding. If more than one MSP is used (i.e., a collection of MSPs), additional factors include: 4) collision of MSPs; and 5) MSPs adhering to one another. Item 1 will not cause any false signal because the permanent deformation results in the resonance peak separating into two peaks whose resonance frequencies are slightly higher than the initial resonance frequency; this has been confirmed experimentally. Item 2 may cause a false signal. The probability of item 2 occurring in a measurement can be significantly reduced or eliminated by using the magnetic stirring technique described herein. Item 3 is a problem related to the use of biosensors generally. Item 4 will result in only a momentary appearance of a resonance peak shift; after the collision, the resonance frequency will return to its pre-collision value. However, such collisions would contribute to "background noise." The probability of item 4 occurring can be reduced by employing fewer MSPs. Item 5 may lead to a false signal, but is expected to occur only rarely.

Unique features of MLSDs employing MSPs. Being a magnetic material, the MSP has all the advantages of magnetic beads. More importantly, the MSP itself serves as the sensor platform. Therefore, the methodology proposed in this project has the advantages of both magnetic beads and AW devices. Additionally, MSPs have a demonstrated higher sensitivity and larger Q value than the best known AW devices. The combination of the advantages of magnetic beads and AW devices yields the following unique features:

Multiple sensor approach: As illustrated by the experiment described in Example 2 (and shown in FIGS. 3 and 15), a collection of many MSPs can be employed to simultaneously bind with a small number of target species in the analyte. An MSP with added mass is clearly identified by the appearance of a peak at a lower frequency. The multiple sensor approach significantly increases the ability of this technique to detect target species of very low concentration due to the small size and large number of the MSPs.

Magnetic stirring technique: Due to their magnetic nature, the MSPs can be stirred using a magnetic field to enhance binding of the target species to the sensor surface. Stirring will significantly reduce analysis times. After reaction with the analyte, measurements can be conducted by: 1) in situ testing; 2) concentrating MSPs into a "measurement zone" using a magnetic field prior to testing; and 3) separating MSPs from analyte using a magnetic field and then testing elsewhere, for example, in air.

Isolation technique: Additionally, due to its remote operation and magnetic nature, an isolation technique can be used to make measurements in flowing liquids such as a pipeline, as shown in FIG. 25. A magnetic field may also be used to locate and guide the MSPs to regions where tests will be conducted, or to remove the MSPs from solution, etc.

Production of MSPs: The selection of magnetostrictive materials for use in MLSDs of the invention may be based on the following considerations: 1) magnetostriction and permeability of the material; 2) the Q value of the material; and 3) Service and Curie temperature. Strip-like MSPs with different sizes have been successfully fabricated using shear cutting, laser cutting, and microelectronics fabrication.

MSPs have been fabricated with thicknesses (i.e., a first dimension) ranging from 5 to 30 μm, lengths (i.e., a second dimension) ranging from 30 mm down to 80 μm, and widths (i.e., a third dimension) from 5 mm down to 20 μm. One of skill in the art will know how to prepare MSPs of different sizes and compositions to meet the performance specifications necessary for a particular application. For example, for MSPs with a thickness above 5 μm, the commercially available material Metglas® solution 2826 MB can be used. For MSPs with a thickness less than 5 μm, thin films of magnetostrictive alloy can be prepared first. Various deposition techniques may be employed, for example, sputtering and electrochemical deposition techniques. Useful materials also include $Fe_{80}B_{20}$, which has a saturation magnetostriction of about 30 ppm and a low loss, as well as silicon-doped $Fe_{80}B_{20}$. See also, Vazquez et al. (2000) "Magnetic anisotropies in single and multilayered thin films grown by bowed-substrates sputtering," IEEE Trans. Magn. 36:3968 (2000) and Luborsky (1980) *Ferromagnetic Materials* 1:503 (Wohlfarth, E P, Ed, Amsterdam, North-Holland).

The compositions of the thin film can be optimized based on the performance of the thin film. Micro-fabrication techniques are used to fabricate MSPs from the thin film. In one processing scheme, the MSPs are fabricated using lift-off on a Si wafer or equivalent substrate. In this technique, a photoresist is laid down and patterned, leaving photoresist in the desired shape of the MSP. The magnetostrictive material is then deposited using RF magnetron sputtering or other suitable deposition method. Finally, the photoresist is dissolved and the MSP is lifted off of the Si wafer. Other coatings (103 and 105), including gold, can be deposited at the same time as the magnetostrictive material. For example, see Madou (1997) *Fundamentals of Microfabrication* (CRC Press); Jaeger (1993) *Introduction to Microelectronic Fabrication, Modular Series on Solid State Devices—Vol. V* (Addison-Wesley Publishing); and Maluf (2000) *An Introduction to Microelectromechanical Systems Engineering* (Artech House Publishers).

The MSP resonator may be coated, impregnated, or chemically bound with the binding element. The binding element component of MLSDs comprises any substance that can be coupled to the sensor device to provide a functional MLSD, that is, an MLSD that permits detection of a particular substance, such as, for example, ligand that is bound to a binding agent. Thus, the binding element can be, for example, a chemical that changes when exposed to conditions such as humidity or heat, or the binding element can comprise a binding agent such as engineered bacteriophage, antibodies, peptides, chemical compounds, nucleic acid molecules, cells, etc.

Where the binding element is a chemical compound or chemically selective compound, the binding element is formulated in accordance with techniques and principles known in the art. See, for example, Monreal and Mari (1987) *Sensors & Actuators* 12:129; Chuang et al. (1982) *IEE Electron. Dev. Lett.* EDL-3:145; Ballentine, Jr. and Wohletjen (1989) *Anal. Chem.* 61:704A; Ward and Buttry (1990) *Science* 249: 1000; Ho et al. (2003) *Sensors* 3:236.

Binding Agents for use in Binding Elements of MLSDs: For use as the binding agent 110 of MLSDs, phage may be engineered to produce foreign peptides rather than wildtype or native phage coat proteins, particularly pVIII and pIII. Filamentous phage such as M13, f1 and fd are thread-shaped bacterial viruses. The outer coat of these phage is composed of thousands of 50-residue α-helical subunits of the major coat protein pVIII which overlap one another to form a tube encasing the viral DNA. Several copies of each of four minor coat proteins, including pIII and pVI, form the tips of this tubular sheath. To create engineered phage, at least one short foreign coding sequence is spliced or substituted into a phage gene, for example, the pVIII gene so that an altered or foreign amino acid sequence is displayed on every pVIII subunit (see, e.g., copending U.S. application Ser. No. 10/289,725, filed Nov. 7, 2002).

If the pVIII gene is altered, the amount of alteration which can be made to the gene is limited only by the physical limitations of the phage and the requirements of the MLSD; any alteration may be made so long as the resulting phage can be used to assemble a functional MLSD. Thus, the term "foreign peptide" encompasses pVIII proteins in which as few as one amino acid residue is altered. Thus, a foreign peptide may have the native sequence of a pVIII protein except for 1, 2, 3, 4, 5, 6, 7, 8, 9, 10, 11, or 12 or more amino acid alterations, including, for example, substitutions, additions, and deletions. The term "foreign peptide" encompasses embodiments in which the altered pVIII gene comprises multiple altered amino acid residues interspersed with unaltered, or wildtype, pVIII amino acid residues. Where the altered amino acid sequence is derived from a native protein, the altered sequence may represent only a small portion, or fragment, of the native amino acid sequence from which it is derived. In this manner, a foreign peptide that comprises a portion or fragment of a native protein may be said to be derived from that native protein.

Methods and compositions for creating engineered phage are known in the art (see, e.g., Petrenko et al. (1996) *Protein Engineering* 19(9):797-801). In such an engineered phage, the foreign peptide is identical in all the coat proteins or subunits of a single virion. Thus, in some embodiments, the assembled phage viral sheath will have a structure in which altered amino acids are interspersed with the wild-type amino acids in a "landscape" to which ligands may bind. The foreign peptide can adapt various conformations depending on composition and sequence of amino acids that form the peptide, so in some embodiments the foreign peptide will protrude from the surface of the viral sheath.

Phage can also be engineered to create phage-display libraries, as is well-known in the art. A phage-display library is a collection of engineered phage, each of which contain a short foreign coding sequence spliced into the major coat protein gene so that the altered amino acids are displayed on every coat protein subunit. A phage-display library as a whole can represent billions of different peptides altogether. The peptide specified by the foreign coding sequence is displayed on the surface of the phage or virion. Because the viral carrier is infective, phage can be cloned individually, and either whole libraries or individual clones can be propagated indefinitely. Phage-display technology is well-known in the art. See, for example, Scott and Smith (1990) *Science* 249:386-390; Sidhu (2001) *Biomol. Eng.* 18(2):57-63; Kischenko et al. (1994) *J. Mol. Biol.* 241:208-213. Random peptide libraries are also known in the art (see, for example, Barbas 3d (1993) *Curr. Opin. Biotechnol.* 4(5):526-530), and a billion-clone library of filamentous phage with different surface structures was demonstrated by Petrenko et al. (1996) *Protein Engineering* 19(9):797-801. Several U.S. patents describe random peptide libraries, including: U.S. Pat. No. 5,723,286 (with inventor Dower); U.S. Pat. No. 5,223,409 (with inventor Ladner); U.S. Pat. No. 5,403,484 (with inventor Ladner); and U.S. Pat. No. 5,571,698 (with inventor Ladner). Phage structure is extraordinarily robust, being resistant to heat (up to 70° C.), many organic solvents (e.g., acetonitrile), urea (up to 6 M), acid, alkali and other stresses. Purified phage can be stored indefinitely at moderate temperatures without losing infectivity.

By selecting a particular method of biotinylation (further discussed herein below) and controlling the density of phage on the sensor 100 as well as other properties of the phage, the sensor, and how the phage is attached to the sensor to form the binding element, phage arrays may be assembled that have optimal properties for the assay of interest. Binding agents 110 comprising very dense, linear phage arrays ("velvet-type" arrays) tend to exhibit monovalent binding behavior, while less-dense, largely non-linear phage arrays ("felt-type" array) tend to exhibit multivalent binding behavior. The multivalent interaction, widely used in biological and chemical systems for increasing affinity of binding due to avidity, has been effectively used in other contexts to enhance affinity. Affinity has been shown to increase as much as a thousand fold where the binding valence increased from monovalent to divalent binding (see Kramer and Karpen (1998) *Nature* 395: 710-713).

As binding agents of a biosensor device, phages with high avidity can provide practically irreversible binding of polyvalent antigens such as bacteria and viruses. This property of an MLSD may be useful in detection of very low concentrations of microorganisms in a large liquid sample or a flow of liquid sample over the biosensor. This property may also be useful in detecting ligands which are present in a gas, such as for example ambient air, and in this manner the MLSDs of the invention can provide detection of airborne contaminants such as, for example, toxic gases or bacterial spores.

The MLSD is exposed to one or more samples, for example, by layering a sample solution that may contain a target ligand 120 onto the MLSD or by immersing or mixing the MLSD in the specimen 400 sample. MLSDs may also be exposed to gases. For example, MLSDs may be exposed to ambient air or other gases for the detection of harmful agents and toxins which are airborne contaminants such as spores of *Bacillus anthracis* (BAS). In other embodiments, solutions of purified or partially purified ligands may be exposed to the MLSD for quantitation or evaluation. Thus, any sample may be assayed by exposure to a MLSD, so long as the form of the sample is compatible with exposure to the MLSD. The terms purified or partially purified ligand solution are intended to mean that the ligand used to make the solution is substantially free of cellular material and includes preparations of ligand having less than about 30%, 20%, 10%, 5%, 4%, 3%, 2%, 1%, 0.1%, 0.01%, or 0.001% (by weight) of contaminating material.

For detection of ligands, the MLSDs of the invention may be used in conjunction with device(s) that isolate and/or concentrate ligands from a sample. Thus, in a sensor system of the invention, the MLSD may be configured with other devices to permit the continuous monitoring, detection and/or alarm of the presence of a particular ligand such as, for example, airborne anthrax spores.

In addition to providing assays for identifying ligands of foreign peptides, one of skill in the art will recognize that the present invention has many applications. For example, the present invention provides assays and compositions for identifying solutions and compositions that do not interact with a particular binding element. Thus, the present invention provides both positive and negative assays as well as quantitative binding assays which may be used in a variety of applications, for example, to design peptides or peptide moieties which may have particular properties. In this manner, ligands may also be compounds or compositions that may be useful because of their interaction or lack of interaction with the binding element. For example, a ligand may be a pharmaceutical compound which binds to one binding agent but not to another, indicating that the pharmaceutical will bind to a cell surface marker of a particular cell type but not another.

Thus, the invention provides compositions and assays for the rapid discovery of ligands which bind to binding element or agent. A ligand is any compound, particle, or organism that binds at some measurable level to a binding element or agent, thereby producing a signal that is detectable by an MLSD of the invention. Thus, a ligand may be, for example, a biological or organic agent such as a protein or peptide, a DNA or RNA molecule or other nucleic acid molecule, a virus, bacterium, fungus, prion, rickettsia, amoeba, or other pathogen or a natural or synthetic toxin.

The term "virus" as used herein encompasses any virus, for example, smallpox virus, yellow fever virus, cholera virus, or a hemorrhagic fever virus such as Ebola virus, Marburg virus, or Lassa fever virus. The term "bacteria" as used herein encompasses bacterial spores and includes any species of bacteria, such as, for example, those bacteria known to cause bubonic plague (e.g., *Yersinia pestis*), pneumonic plague, and anthrax (e.g., *Bacillus anthracis*). Toxins include but are not limited to organic toxins such as ricin, botulism toxin (e.g., *Clostridium botulinum* toxin), aflatoxin, *Clostridium perfringens* toxin, and Staphylococcal enterotoxin B. In some embodiments, a sample of a beverage, food or food source is tested for the presence of a particular ligand. Representative bacteria, viruses, and toxins are shown in Tables 3 and 4.

TABLE 3

Six Most Common Bacteria Responsible for Foodborne Illness

| Bacteria | Cases | Deaths | Infectious Dose | Approx. wt |
|---|---|---|---|---|
| Salmonella typhimurium | 3,840,000 | 3,840 | $10^4$ to $10^7$ | 0.8~2.0 pg |
| Campylobacter jejuni | 4,000,000 | 511 | 400 to $10^6$ | 0.02~1.5 pg |
| Staphylococcus aureus | 1,513,000 | 1,210 | >$10^6$ | |
| E. coli O157:H7 | 725,000 | 400 | 10 to 100 | 1.0~4.5 pg |
| Clostridium perfringens | 10,000 | 100 | >$10^8$ | |
| Listeria monocytogenes | 1,767 | 485 | 400 to $10^3$ | 0.06~0.25 pg |

TABLE 4

Viruses and Toxins

| Name | Size | Approx. wt. |
|---|---|---|
| Viruses | | |
| Variola (Small Pox) | 250 × 270 nm | 13 fg |
| Hanta virus | 90–120 nm | 1 fg |
| Ebola | 790–970 × 80 nm | 4–6 fg |
| Lassa Fever virus | 110–130 nm | 1.5 fg |
| Hepatitis A virus | 28–30 nm | 0.02 fg |
| West Nile virus | 45–60 nm | 0.1 fg |
| Toxins | | |
| Ricin | 66 kDaltons | $1 \times 10^{-19}$ g |
| Botulinum toxin | 150 kDaltons | $2.5 \times 10^{-19}$ g |
| Staphylococcal enterotoxin B | 28 kDaltons | $4.5 \times 10^{-20}$ g |
| Clostridium perfringens Epsilon toxin | 35,000 mw | $6 \times 10^{-20}$ g |

Ligand binding is detected and can be quantitated using an MLSD of the invention. Ligands as well as peptides of interest may be isolated or derived from any organism or species, including but not limited to mammals, reptiles, amphibians, plants, bacteria, viruses, amoeba, rickettsia, etc. Thus, the MLSDs of the invention find use in detecting any ligand 120 that is capable of binding to a binding element 130. More than one ligand may bind to a particular binding agent or to a particular binding element.

Where a binding agent is a peptide of interest that is specific to a particular cell type or tissue, or to a tissue affected by a particular disease or disorder, binding elements comprising that peptide of interest may be used to identify and isolate ligands which bind the particular peptide of interest. Such compounds may be useful for delivery of other compounds to the particular cell type or tissue, or they may themselves be useful in treating the particular cell type or tissue from which the peptide of interest was isolated. In this manner, peptides of interest may be associated primarily with a disease or disorder, such as a tumor or particular type of tumor. Based on the selective binding protocols, compounds which are tissue-type specific or alternatively which are capable of binding to different cells can be determined. In the same manner, peptides of interest may be species independent, that is, the peptides are associated with the same tissue type or cell type from any species. Alternatively, the peptides may be species-specific. The term "species-specific" is intended to mean that the peptides are specific to a particular ligand, such as tissue cells (e.g., liver or bacterial spores) from a particular species and will not bind to the same tissue cells from another species. Peptides of interest may be isolated from or identified in any species. Mammalian species of interest include, but are not limited to human, rat, dog, chimpanzee, etc.

Peptides of interest may be specific to a particular cell culture, cell type, tissue, stage of development, or disease or disorder or they may be preferentially associated with a particular cell type, stage of development, or disease or disorder. Peptides of interest may also be generally expressed by more than one tissue, or by many tissues, or may be associated with many tissue states.

Methods are available in the art for the identification and isolation of peptides of interest. Such methods can include selection from a bacteriophage (phage) library which expresses random peptides or specifically designed peptides, mirror image phage display to isolate naturally-occurring L-enantiomers in a peptide library, and the like. See, for example, Barry et al. (1996) *Nature Medicine* 2:299-305; Schumacher et al. (1996) *Science* 271:1854-1857; Pasqualini et al. (1996) *Nature* 380:364-366; U.S. Pat. No. 6,329,501, issued Dec. 11, 2001, and the references cited therein, herein incorporated by reference. Peptides of interest can also be selected based on, for example, the sequence of cell surface proteins or by in vivo phage display screening as discussed in copending applications application Ser. No. 09/947,137, filed Sep. 5, 2001, and application Ser. No. 09/438,150, filed Nov. 10, 1999, herein incorporated by reference. See also co-pending U.S. application Ser. No. 10/068,570, filed Feb. 6, 2002, hereby incorporated by reference. Peptides of interest may also be random peptides, i.e., peptides with random amino acid sequences, or the amino acid sequence may be designed.

Once peptides of interest or foreign peptides have been selected, they may be modified by any suitable method for use as a binding agent. Such methods include random mutagenesis as well as synthesis of peptides containing selected amino acid substitutions. Peptides of various lengths can be constructed and tested for the effect on binding affinity and specificity of a test ligand. The compositions and assays of the invention may also be used to evaluate variants of the peptide sequence(s) for enhanced affinity to a particular ligand, such as, for example, a phage that binds strongly to the original peptide or a similar peptide.

A nucleic acid molecule comprising a nucleotide sequence that encodes the peptide of interest can be used in the construction of foreign proteins, coding regions, or vectors for use in the invention. Such methods are known in the art (see, e.g., Smith and Petrenko (1997) *Chemical Reviews* 97:391-410, and references cited therein). Additionally, the construction of expression cassettes is known as well as promoters, terminators, enhancers, etc., necessary for expression. By nucleic acid molecule is intended gene sequences, DNA, RNA, as well as antisense nucleic acids. Standard techniques for the construction of the nucleic acid molecules of the present invention are well-known to those of ordinary skill in the art and can be found in such references as Sambrook et al. (2001) *Molecular Cloning: A Laboratory Manual* (3d ed., Cold Spring Harbor Laboratory). A variety of strategies are available for ligating fragments of DNA, the choice of which depends on the nature of the termini of the DNA fragments and which can be readily determined and accomplished by those of skill in the art. Methods for engineering nucleotides, peptides, and phage are known in the art. See, e.g., methods reviewed in Smith and Petrenko (1997) *Chemical Reviews* 97:391-410.

The binding element can comprise a uniform population of binding agents, i.e., a population of the same entity, or it may comprise a mixed population of binding agents, i.e., a population comprising more than one entity. Thus, for example, an MSP may have a binding element comprising a population of the one peptide binding agent or it may comprise a population of two or more peptides, a population of a peptide and an antibody, etc. One of skill is able to select suitable binding elements (including binding agents) and to adjust the composition of the binding element to optimize performance of the MLSD of the invention. Factors to be considered in selecting the binding element include the substance to be evaluated (i.e., small chemical or larger molecule such as a peptide), relative sizes of a binding agent in comparison to the size of the expected ligand, the performance of the MLSD with similar binding elements or binding agents, the sensitivity of the MLSD when coupled to similar binding elements or binding agents, and other factors which will be evident to one of skill in the art.

The binding element may be coupled to the sensor (MSP, for instance) in any manner which provides a functional MLSD, i.e., which provides an MLSD which detects the alteration of the binding element as a result of exposure to the substance of interest, for example, the binding of a ligand to the binding agent. Thus, for example, when coupled to the MSP, phage are capable of interacting with ligands and this interaction is detected by the MSP. In some embodiments, attachment of phage to the MSP is accomplished using the N-terminal amino-groups or amino-butyl groups of the $Lys_{10}$ residue of the major coat protein. Cross-linkers for this purpose are commercially available, and one of skill in the art can readily select an appropriate cross-linker or combination of coupling compositions to produce the MLSDs of the invention. In some embodiments, the MSP is prepared by the addition of one or more coatings or layers to which the binding element will bind, and the preparation of the binding element or binding agent to be coupled to the MSP simply comprises ensuring that the binding element (and, if present, binding agent) is at a proper concentration for addition to the prepared MSP. That is, for example, the MSP may be coated with streptavidin and the binding element may consist of a binding agent which is biotinylated peptide. In other embodiments, the MSP is prepared by thorough cleaning and the phage binding agent is directly bound to a gold sensor surface by interaction with the phage tip (i.e., the pIII protein). For a "brush-type" conjugation of phages to the MSP, a tag peptide such as streptavidin-binding peptide HPQ or a biotinylation site can be engineered into the minor coat protein pIII located on the tip of the phage. The phage can then be conjugated non-covalently to a streptavidin-coated MSP. In other embodiments, where a peptide is engineered with a streptavidin-binding "tag" and either used directly or expressed on an engineered phage, the MSP can be prepared with a Langmuir-Blodgett film or coating of biotinylated phospholipid. In such embodiments, the assembly of the MLSD may be accomplished by the addition of streptavidin to couple the peptide or landscape phage binding agent to the MSP.

Thus, the MSP may be coupled or linked to the binding element by any suitable composition and method so long as the resulting MLSD is capable of detecting a change in the binding element. In some embodiments, the step of preparing the resonator may simply comprise ensuring that the MSP or resonator 100 is clean and ready to be coupled to the binding element 130, which may or may not comprise a binding agent 110 (see generally, Cunningham (1998) *Introduction to Bioanalytical Sensors* (Wiley-Interscience)). In addition to phage, "skinned phage" or monolayers derived from phage may be used. See, for example, copending application Ser. No. 10/792,187, filed Mar. 3, 2004.

In some embodiments, a resonator is coated with gold or a gold-coated resonator is obtained; the resonator is then coated with a coupling composition layer 105 (FIG. 5), such as streptavidin and coupled via biotin to the binding agent 110, such as, for example, peptides, antibodies, or landscape phage. Alternatively, the coupling composition layer 105 which attaches the binding agent 110 to the resonator 100 may comprise a suitable polymer coating 103. In some embodiments, the coupling composition layer 105 may comprise biotinylated thiol or disulfide layer which is linked directly to a coating 103 of gold; the biotinylated layer is then linked to streptavidin and coupled via biotin to the binding agent 110. See, for example, Luppa et al. (2001) *Clinica Chimica Acta* 314:1-26; Gau et al. (2001) *Biosensors & Bioelectronics* 16:745-755. Of course, in some embodiments, only one layer or coating is used to create the binding element of the MLSD. For example, a gold coating or a monolayer of molecules can provide a means of attachment of binding agents to an MSP. See, for example, Dong and Shannon (2000) *Anal. Chem.* 72:2371 (2000); Volmer-Uebing and Stratmann (1992) *Applied Surface Science* 55:19.

In other advantageous embodiments, a Langmuir-Blodgett film or coating of biotinylated lipid can be added to the MSP. Langmuir-Blodgett films are formed from at least one monolayer. A monolayer is a one-molecule-thick film of at least one amphiphilic compound or composition that forms at the air/water interface of an aqueous solution. Each molecule in the monolayer is aligned in the same orientation, with the hydrophobic domain facing the air and the hydrophilic domain facing the aqueous solution. Compression of the monolayer results in the formation of an ordered two-dimensional solid that may be transferred to a substrate by passing the substrate through the monolayer at the air/liquid interface. A monolayer that has been transferred to a substrate is termed a Langrnuir-Blodgett film, or LB film. For reviews of Langmuir-Blodgett technology, see Gaines (1966) "Insoluble Monolayers at Liquid-Gas Interfaces," *Interscience* (New York); Zasadzinski et al. (1994) *Science* 263:1726-1733; Ullman (1991) *An Introduction to Ultrathin Organic Films* (Academic Press, Boston, Mass.); and Roberts (1990) *Langmuir-Blodgett Films* (Plenum, New York); the contents of which are incorporated herein by reference.

Monolayers are typically composed of organic molecules such as lipids, fatty acids and fatty acid derivatives, fat soluble vitamins, cholesterol, chlorophyll, valinomycin and synthetic polymers such as polyvinyl acetate and polymethyl methacrylate. Monolayers may also be formed by many other amphiphilic compounds; thus, many amphiphilic compounds may be used to form the monolayers of the invention. Such compounds include lipids having at least 14 carbon atoms. Examples include stearic acid and hexadecanoic acid. Other compounds that will form monolayers include but are not limited to those described in Gaines, (1966) "Insoluble Monolayers Liquid-Gas Interface," *Interscience* (New York), the contents of which are incorporated by reference.

Lipid monolayer depositions may be carried out by methods known in the art and as described in copending application Ser. No. 09/452,968, filed Dec. 2, 1999, herein incorporated by reference in its entirety. Langmuir-Blodgett (LB) film balances are commercially available, for example from KSV-Chemicals, Finland, and are operated in accordance with the supplier's instructions.

The Langmuir-Blodgett film is formed by the successive transfer of monolayers onto the surface of the sensor device using the Langmuir-Blodgett technique. In some embodiments, biotinylated lipid solutions are spread on the aqueous subphase as hexane solutions. The monolayer is then compressed and a vertical film deposition is performed. In LB film deposition, multiple monolayers may be added to the sensor by successive dipping of the sensors through the monomolecular film deposited at the air/liquid interface. LB films may be formed by the addition of one, two three, four, five, six, seven, eight, nine, ten, eleven, twelve, thirteen, fourteen, or fifteen or more monolayers in this manner to create the final Langmuir-Blodgett film.

The monolayers used to create the Langmuir-Blodgett film may be formed without the aid of a volatile organic solvent. See, for example, copending application Ser. No. 09/452,968, filed Dec. 2, 1999. Many methods for forming LB films require dissolution of the compounds to be formed into a monolayer in a volatile organic solvent such as hexane. The organic solvent forms a separate phase from the aqueous solution and functions to prevent dissolution of the monolayer components in the aqueous phase. After spreading the mixture at the air/liquid interface of the aqueous solution, the solvent is allowed to evaporate, leaving a monolayer at the interface. However, in such embodiments, the organic solvent may damage the monolayer components and leave an undesirable residue which contributes to background levels of nonspecific binding. Thus, in some embodiments, monolayers formed without the aid of an organic solvent as set forth in copending application Ser. No. 09/452,968, filed Dec. 2, 1999, provide improved properties to the MLSDs of the present invention. In some embodiments, a landscape phage is covalently bound or linked to phospholipids; vesicles comprising these phospholipids are then used to create monolayers and LB films to make an MLSD of the invention. In such embodiments, the coupling of the phage to the resonator may be accomplished by the formation of such an LB film on the resonator and does not necessarily require a coupling via streptavidin and biotin interactions. Such resonators may be gold-plated or coated with other material to facilitate the adherence of the LB film to the resonator. A monolayer can comprise a mixture of compounds and can even be formed with, for example, serum, so that the monolayer itself comprises antibodies which are normally found in serum. Additional methods of forming LB films are known to those skilled in the art and are described in Ullman (1991) *An Introduction to Ultrathin Organic Films* (Academic Press, Boston, Mass.); and Roberts (1990) *Langmuir-Blodgett Films* (Plenum, New York); the contents of which are incorporated herein by reference.

One of skill in the art will appreciate that for different applications of the assays of the invention, resonators with different sensitivities and outputs may be used. Thus, for example, in some applications a preferred MLSD will be capable of high-resolution quantitation of changes in binding, while for other applications a MLSD need only detect the presence or absence of high-affinity binding. In some applications, a MLSD exhibiting little or no hysteresis will be preferable, while in other applications, the ideal MLSD will be one which exhibits a high degree of hysteresis.

Other Structural Embodiments of the MLSD (Cantilevers, Bridges, and Membranes): In other advantageous embodiments, the sensor device of the present invention is a structure in which the magnetostrictive material is incorporated as a freestanding cantilever, bridge, or membrane (see FIG. 11), as commonly employed in frequency-shift by mass-attachment sensor schemes. See, for example, U.S. Pat. No. 5,998,995; Tiercelin et al. (2000) *Sensors and Actuators A: Physical* 81:162-165; Grabham et al. (2000) *Electronics Letters* 36:332-334; Hristoforou et al. (1999) *Sensors and Actuators A: Physical* 76:156-161; Mohri et al. (1997) *Sensors and Actuators A: Physical* 59:1-8; Chiriac et al. (1997) *Sensors and Actuators A: Physical* 59:280-284; Kaneo et al. (1997) *Sensors and Actuators A: Physical* 59:1-8. However, the MLSDs of the present invention can generate larger strains than piezoelectric devices, enabling higher Q-value responses and therefore providing sensors with enhanced sensitivity. Also these alternate structural embodiments may further incorporate other advantageous features of the present invention, including, for instance, coatings 103, coupling composition layers 105, and binding agents 110 as described more fully herein. In some embodiments, the magnetostrictive materials will be supported by and passivated from the solution by a suitable substrate such as an oxide or nitride.

The microfabrication process for these microsensors is generally as follows and is described in more detail in Madou (1997) *Fundamentals of Microfabrication* (CRC Press), Jaeger (1993) *Introduction to Microelectronic Fabrication, Modular Series on Solid State Devices—Vol. V* (Addison-Wesley Publishing), and Maluf (2000) *An Introduction to Microelectromechanical Systems Engineering* (Artech House Publishers).

The first step is the deposition of the platform material, such as, for example, silicon oxide or silicon nitride, onto a suitable substrate, for example, a (100) oriented single crystal silicon wafer. The deposition procedure produces a thin-layer coating on the particular substrate ranging from submicron thickness to thicknesses of a few microns or more. Techniques to achieve this include low-pressure-chemical-vapor deposition (LPCVD), plasma enhanced chemical-vapor deposition (PECVD), and equivalent techniques.

The next step involves the deposition of the magnetostrictive material onto the platform material by a technique providing thin-layer coating of the material. Techniques to achieve this include sputtering, electron-beam evaporation, chemical vapor deposition, or equivalent techniques. The next step involves the deposition of, for example, gold or platinum to serve as the substrate-specific area to which the binding element will be attached. Techniques to achieve this include sputtering, electron-beam evaporation, chemical vapor deposition, and equivalent techniques. This process can be performed using the lift-off technique, whereby a photoresist defines the specific areas where this layer will be deposited.

The next step is the deposition of a suitable passivation film to enclose all areas of the device. This material may be an oxide, nitride, or other suitable material. Techniques to achieve this deposition include sputtering, plasma-enhanced-chemical-vapor-deposition (PECVD), and equivalent processes. In the cases of the cantilever or bridge structures, the passivation and platform layers are removed to define the structure. This step will also remove the passivation layer from the gold or platinum areas discussed above. Techniques to achieve this include plasma etching, buffered oxide etch (BOE), or other suitable processes depending on the materials selected for either layer. As discussed above, a photoresist may be used to define the specific areas to be etched away.

In the next step, the structures are released into freestanding elements, that is, they are no longer supported by the silicon substrate. All three structures can be released by backside etching of the silicon wafer substrate using either KOH or deep-reactive-ion etching (DRIE). In the case of the cantilever structure, release of the cantilever can be accomplished by KOH etching from the front-side, provided that the platform and passivation layers are not affected by the KOH solution. The final step is application of the binding element to the exposed gold or platinum area using attachment chemistries discussed earlier.

Each of these three microsensor structures (cantilever, bridge and membrane) has a different behavior and sensitivity to the attachment of a mass. The response of the cantilever is dependent on several material and geometrical characteristics. For instance, the natural frequency (f) is dependent on the elastic modulus (E) of the cantilever material as well as its thickness (t) and length (L), as seen in the following relation:

$$f = \frac{\lambda_1^2}{2\pi} \frac{t}{L^2} \sqrt{\frac{E}{12\rho}} \quad (9)$$

where ρ is the density of the material and $\lambda_1$ is the first root solution of $\cos \lambda_i \cosh \lambda_i + 1 = 0$ which dictates the boundary conditions of the oscillating fixed-free cantilever. Solutions of $\lambda_i$ include: $\lambda_1 = 1.875$, $\lambda_2 = 4.694$, $\lambda_3 = 7.855$, etc.

Each of the microsensor structures has sensitivity to mass attachment whereby the natural frequency shifts as a result. Analytical expressions for this behavior are given in Table 5 for each structure.

TABLE 5

Resonant state and effect of added mass for three microsensor structures

| Structure | Resonant State | Effect of Mass Added |
|---|---|---|
| Cantilever | $f_1 = \dfrac{\lambda_1^2}{2\pi} \dfrac{t}{L^2} \sqrt{\dfrac{E}{12\rho}}$ | $f_1 = \dfrac{\lambda_1^2}{2\pi} \sqrt{\dfrac{Ewt^2}{12 \cdot L^3(M_c + 0.24 M_{add})}}$ |
| Bridge | $f_1 = \dfrac{4\lambda_1^2}{\pi} \dfrac{t}{L^2} \sqrt{\dfrac{E}{12\rho}}$ | $f_1 = \dfrac{4\lambda_1^2}{\pi} \sqrt{\dfrac{Ewt^2}{12 \cdot L^3(M_c + 0.37 M_{add})}}$ |
| Circular Membrane | $f_{11} = \dfrac{\lambda_{11}^2}{2\pi r^2} \sqrt{\dfrac{Et^3}{12\rho(1-v)^2}}$ | $f_{11} = \dfrac{10.22 - 24\dfrac{M_{add}}{M_c}}{\pi r^2} \sqrt{\dfrac{Et^3}{3\rho(1-v)^2}}$ |

The operation of the microsensor involves generation of a modulated magnetic field via a magnetic induction coil or other source. The field generated by the coil causes the magnetostrictive cantilever, bridge or membrane to be actuated and respond mechanically to the field in a manner similar to the MSP of the same invention. This actuation stores elastic energy from straining that is released during the field wells in the modulated signal and generates itself, a modulated magnetic field proportional to the induced straining that is received by the coil. When the frequency of the coil generated field matches the natural frequency of the structure, the induced strain is at a maximum and, correspondingly, so is the magnitude of the induced microsensor signal. The frequency at which the structure resonates is a function of its dimensions, the mass attached to it and the damping of the environment. Therefore, by either reading the device response before and after mass attachment or by fabricating a reference device with identical behavior before mass attachment, the qualification and quantification of the presence of a hazardous species can be determined.

Microscale sensing platforms of the nature described above have ubiquitous application in sensing since they can be easily configured to detect different biological and chemical species by merely exchanging the sensing probe for that species. For instance, an antibody selective only to *Salmonella typhimurium* can be swapped for an antibody selective to *E. coli* without any alteration of the sensor platform.

The following examples are intended to illustrate various embodiments and principles of the present invention rather than to limit the invention.

EXPERIMENTAL

Example 1

Biosensor Based on Strip-Like Magnetostrictive Particles

MLSDs were created by attaching antibodies to the surface of magnetostrictive particles to form a sensor device that would respond to the binding of bacteria. Magnetostrictive strip resonators were made from Metglas® solution 2826 MB that was 28 micrometers thick (Metglas®, Inc., 440 Allied Drive, Conway, S.C., USA). These magnetostrictive strips were coated with a layer of gold and an anti-*Salmonella* antibody was then immobilized onto the surface of the gold-coated strip using the Langrnuir-Blodgett (LB) technique. At each step of the MLSD fabrication process, the resonance frequency of the particles was measured. The MLSD was then exposed to different solutions of water containing different concentrations of *Salmonella typhimurium* bacteria; measurements were conducted in air after the MLSD was removed from the bacterial solution. FIG. 13 shows the measured resonance behavior at different stages in the experimental process (see also schematic explanation in FIG. 8). The first resonance curve was obtained from the gold-coated magnetostrictive particle. The resonance behavior was again measured after immobilizing antibody onto the surface of the particle. As anticipated, there was very little change in the particle resonance frequency (<20 Hz) because the mass of the monolayer and antibody are negligible.

After exposure to and binding with *Salmonella* bacteria, the sensor shows a shift of 310 Hz in resonance frequency. To confirm the binding of *Salmonella* and to quantify the number of bacteria bound onto the surface of the sensor, the sensor was exposed for 30 minutes to $OsO_4$ vapor to fix the bacteria for viewing with a Scanning Electron Microscope (SEM); the SEM images obtained are shown in FIG. 14. The SEM photomicrograph shown in FIG. 14(b) is for the sensor whose resonance frequency shift measurements are shown in FIG. 13. Very consistent results were obtained between the SEM images and the shift in resonance frequency of the MLSD.

The specificity of the sensor was confirmed by exposing a control sensor (coated with gold and anti-*Salmonella* antibody, as described above) to a solution containing $10^9$ cells/ml of *E. coli* bacteria and examining the sensor surface under SEM. No shift in frequency was observed and no attachment of *E. coli* was found.

Example 2

Demonstration of Multiple-Particle MLSD Use

Ten magnetostrictive particles ("MSPs") were prepared to be nearly identical in size and were coated with gold. These particles (resonators), with no mass load, were placed together and simultaneously measured to assess the performance of an MLSD comprising a collection of MSPs. The top graph shown in FIG. 15 represents data obtained for these ten particles with no mass load. The particles showed similar resonance frequencies clustering over a narrow range of frequencies. One resonator was then removed and a mass was added to this resonator. It was replaced into the group and measurements were taken again. The lower curve shown in FIG. 15 illustrates the appearance of one peak at a lower frequency (due to the mass loading). This experiment shows that, when the MLSD is properly designed, it is very easy to identify a shift in resonance frequency for a single particle in a group or collection of particles.

Example 3

Demonstration of Simultaneous Detection of Multiple Ligands

An MLSD comprising a collection of two sets of particles was fabricated; each set contained two particles. The characteristic resonance frequencies of the two sets of particles were designed to be at different frequencies (here, 87 and 94 kHz). As shown in FIG. 16, the difference in resonance frequency between the sets of particles is large enough to identify a shift in resonance frequency due to a mass load (here, the binding of bacteria to a particle). The data represented at the bottom shows the results for this multiple target system when no mass load was present. When one of the two sensors in each set of particles was loaded with a mass, the response of the multiple target system was changed as shown.

Example 4

Demonstration of Micro-Cantilever

Unimorph-like devices were created by bonding a magnetostrictive film with a metal film. The length/width ratio of the cantilever was about 4 to 5, while the width/thickness ratio of the cantilever was 10 to 20. The relationship between the resonance frequency (f in kHz) and the length (L in mm) of the cantilever is shown in FIG. 17, where the thickness of magnetostrictive film is 30 μm. The resonance behavior of a micro-cantilever is shown in FIG. 18. The Q-value, which is defined here as the resonance frequency divided by the width of resonance peak, is more than 200. This micro-cantilever worked well in both liquid and air (gas), as shown in FIG. 19.

Example 5

Sensor Systems Comprising MSPs

Two sensor systems were constructed to characterize the performance of MLSDs comprising MSPs. One system had the capability to characterize MSPs at frequencies lower than 500 kHz, while the other system was used to characterize MSPs with resonance frequencies higher than 500 kHz. The low frequency system was based on one 24" Helmholtz coil. A home-made coil was used to pick up the signal generated by the MSP and a lock-in amplifier was used to measure the signal from the pick-up coil. Both amplitude and phase delay were recorded as shown in FIGS. 13, 15 and 26. The high frequency system used a network analyzer (HP 8751A, Hewlett Packard USA, 20555 SH 249, Houston, Tex.). The MSPs were placed within a dual induction coil. The primary coil was driven by the Network Analyzer and a response in the analysis coil was used to characterize the resonance behavior of the MSP as shown in FIGS. 23, 27 and 28.

As a wireless/remote sensor, the distance between driving coil and MSP was a variable. This raised a question whether the resonance frequency of the MSP changed with the strength of the driving magnetic field. As shown in FIG. 26, the resonance frequency of the MSP was independent of the strength of the driving magnetic field.

Example 6

MLSDs for Detection of *Bacillus anthracis* Spores

Very high specificity and selectivity of phages binding to target proteins has been routinely confirmed in all selection experiments with phage display libraries in the art. See also, Petrenko and Vodyanoy (2003) *J. Microbiol. Meth.* 53: 243-252 and Smith and Petrenko (1997) *Chem. Rev.* 97: 391-410. In contrast to antibodies, the phage structure is extraordinary stable and robust, being resistant to: heat (up to 80° C.) (see, e.g., Holliger et al. (1999) *J. Mol. Biol.* 288: 649); organic solvents (e.g., acetonitrile) (see, e.g., Olofsson et al. (2001) *Chemistry & Biology* 8: 661); urea (up to 6 M); acid; alkali and other chemicals. Purified phage can be stored indefinitely at moderate temperatures without losing infectivity and probe-binding activity. FIG. 29 compares the stability of Dr. Petrenko's phage, commercial monoclonal antibody (mAb) and commercial polyclonal antibody (pAb) specific to beta-galactosidase after storage at a temperature of 37° C. The data shown in FIG. 29 illustrate that the phage produced a much larger binding signal in an ELISA binding assay than either the mAb or pAb. The phage retained its binding activity even after 21 weeks of exposure at 37° C. The binding activity of mAb dropped significantly after six weeks of exposure at 37° C. The polyclonal antibodies demonstrated very low binding from the start of the experiment and the results fluctuated at the background level throughout the test. There was some deviation in the data that is natural for the ELISA evaluation format used to determine binding. However, the data clearly show that phage binding is more stable than either mAb or pAb at elevated temperatures.

In the experiments described in this example, phage selected for their ability to bind spores of *Bacillus anthracis* Sterne strain were immobilized onto the gold-coated surface of MSPs. This method had previously been employed for immobilization of a wide range of molecules including human serum albumin and viral proteins. The MSPs were exposed to *Bacillus anthracis* Sterne strain spores; electron microscopy confirmed that the spores were bound to the MSPs. The response of the MLSD was characterized.

Specifically, an MLSD of the invention was prepared using an MSP that was 1000 μm×100 μm×20 μm in size. The resonance frequency of the biosensor was measured in air and filtered water prior to exposure to filtered water containing *Bacillus anthracis* Sterne strain spores. The filtered water used in all experiments was obtained from a Millipore Stericup system. In this experiment, 4 μl of spore solution (with a concentration of $2.5\times10^8$ spore/ml) was used. After exposure to the spore solution, the resonance frequency of the MLSD was found to continuously decrease as spores were recognized and became bound to the surface. The test was stopped when a resonance frequency shift of 7.134 kHz was obtained and the biosensor was removed for examination by electron microscopy. A point count measurement of 10 different regions of the sensor surface yielded a value of 45,000 spores that had attached to the sensor surface. This is in good agreement with a calculated 52,000 spores (based upon mass attachment) that would theoretically be needed to achieve the measured 7.134 kHz shift.

FIG. 28 shows the result of a second similar experiment. This experiment was a dynamic experiment in which the resonance frequency of an MLSD comprising an MSP resonator was measured as a function of time. This MSP resonator was 500 μm×100 μm×20 μm in size. In this experiment, the MLSD was exposed to 2 μl of spore solution (with a concentration of $5\times10^8$ spores/ml). The data shown in FIG. 28 illustrate that there was an initial linear change in resonance frequency with time until the biosensor saturated at a value of 31.5 kHz (~3000 s). A theoretical calculation shows that about 57,000 spores would be needed to achieve the measured 31.5 kHz shift.

After completion of the experiment, the MLSD was examined using scanning electron microscopy (SEM) to determine the number of spores that had attached to the MSP sensor surface. The top surface of the sensor (500×100 micron surface area) was photographed and a spore count performed. This number was then divided by the area of the surface to obtain a surface area density and this density was multiplied by the surface area of the sensor to obtain the total number of spores. The total number of spores that attached to the sensor surface was experimentally determined to be approximately 63,000 spores. Thus, frequency shifts of as little as 100 Hz can be identified using this size MSP. Only 200 spores would be required to cause a 100 Hz shift in the resonance frequency. Stability studies have been conducted with this size MSP biosensor in filtered water for as long as four hours. Over this time period, this MLSD shows a drift of less than 50 Hz.

Example 7

Detection of a Single Bacterium Using an MLSD

Extrapolating from the results presented in Example 6, it is expected that by decreasing the size of the MSP to 100×20×2.51 μm, the attachment of one *Bacillus anthracis* spore would result in a frequency shift of 1100 Hz. Thus, an MSP with a length of about 10 μm is predicted to be able to detect mass of less than a femtogram ($10^{-15}$ gram). A bacterium or spore weighs approximately one picogram. Thus, the MLSDs of the invention should enable the detection of a single bacterium/spore and even smaller biological agents, such as, for example, a virus, in both air and water.

FIG. 30 shows a diagram of the sensitivity of MSPs of different thicknesses and sizes, as calculated from equation 12. This diagram indicates that very high sensitivity can be achieved in MSP-based sensors. Thus, for example, for an MSP of 1 μm×100 nm×10 nm, a femtogram mass load would result in a frequency shift of about 200 MHz, or 10% of its resonance frequency. Such high sensitivity would make possible the identification of a single virus as well as a small number of molecules of some chemicals/toxins based on the masses shown in Tables 3 and 4.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A magnetostrictive ligand sensor device for detecting a target species present in a sample, the device comprising:
   a) a collection chamber configured for receiving the sample and mixing the sample with liquid to prepare a liquid sample;
   b) a detection chamber configured for receiving the liquid sample from the collection chamber, the detection chamber comprising magnetostrictive particles;
   c) at least one binding element that is bound to at least one of the magnetostrictive particles and that binds to the target species, wherein alteration of the binding element via binding to the target species produces a resonance response of the magnetostrictive particles;
   d) a magnetic field generator configured for generating a varying electromagnetic field, wherein the varying electromagnetic field stirs the magnetostrictive particles in the liquid sample in the detection chamber, prevents adhesion of the magnetostrictive particles to any wall of the detection chamber, and enhances binding of the magnetostrictive particles to the target species in the liquid sample in the detection chamber;
   e) a driver configured to induce the resonance response of the magnetostrictive particles in the detection chamber, wherein the driver is separate from the magnetic field generator; and
   f) a measurement device for detecting the resonance response of the magnetostrictive particles.

2. The magnetostrictive ligand sensor device according to claim 1, wherein the collection chamber comprises a concentrator.

3. The magnetostrictive ligand sensor device according to claim 2, wherein the concentrator is an air-to-liquid concentrator.

4. The magnetostrictive ligand sensor device of claim 1, wherein the at least one binding element comprises a binding agent that is selected from the group consisting of peptides, phages, and antibodies.

5. The magnetostrictive ligand sensor device of claim 1, wherein the magnetostrictive particles exhibit Q values in liquid that are above 5.

6. The magnetostrictive ligand sensor device of claim 1, wherein the binding element consists of a chemically-sensitive coating.

7. The magnetostrictive ligand sensor device of claim 4, wherein the binding agent is a peptide.

8. The magnetostrictive ligand sensor device of claim 4, wherein the magnetostrictive particles comprises a first magnetostrictive particle with a binding element comprising a binding agent that is a first peptide and a second magnetostrictive particle with a binding element comprising a binding agent that is a second peptide, wherein the first peptide and the second peptide are different peptides.

9. The magnetostrictive ligand sensor device of claim 4, wherein the binding agent comprises engineered phage.

10. The magnetostrictive ligand sensor device according to claim 1, wherein the magnetic field generator comprises a coil configured to produce the magnetic field to remotely distribute and manipulate the magnetostrictive particle in the sample.

11. The magnetostrictive ligand sensor device according to claim 1, wherein the driver is a coil configured to apply a time-varying magnetic field to the magnetostrictive particle and wherein the resonance response is a time-varying magnetic field.

12. The magnetostrictive ligand sensor device according to claim 11, wherein the measurement device includes a pick-up coil configured to detect the time-varying magnetic field from the magnetostrictive particle.

13. The magnetostrictive ligand sensor device according to claim 1 wherein the measurement device further includes:
   a) a filter device;
   b) an amplifier;
   c) a fast Fourier transform device;
   d) a plurality of memory registers;
   e) a central processing unit; and
   f) a display.

14. The magnetostrictive ligand sensor device according to claim 1, wherein the driver is a coil configured to apply a first continuous magnetic field to the magnetostrictive particle and wherein the resonance response is a second continuous magnetic field having a phase delay with respect to the first continuous magnetic field.

15. The magnetostrictive ligand sensor device according to claim 1, wherein the measurement device includes a pick-up coil configured to detect the phase delay.

16. The magnetostrictive ligand sensor device according to claim 1, wherein the binding element comprises a binding agent selected from the group consisting of:
   a) monoclonal antibodies;
   b) polyclonal antibodies;
   c) phage;
   d) skinned phage;
   f) DNA;
   g) RNA;
   h) peptides; and
   i) combinations thereof.

17. The magnetostrictive ligand sensor device according to claim 1, wherein the magnetostrictive particle is a substantially rectangular magnetostrictive strip.

18. The magnetostrictive ligand sensor device according to claim 1, wherein the magnetostrictive particle has a structure selected from the group consisting of:
   a) microcantilevers;
   b) bridges; and
   c) membranes.

19. The magnetostrictive ligand sensor device according to claim 1, further comprising a switch valve located downstream of the detection chamber, wherein if no target species are detected in the liquid sample the switch valve shunts the liquid sample through a modular filter to remove all particulates from the liquid sample and recycle the liquid back to the collection chamber, and if the magnetostrictive particles of the detection chamber exhibit a change in resonance response the liquid sample is passed to a second detection chamber comprising magnetostrictive particles, wherein the magnetostrictive particles of the second detection chamber comprise at least one binding element that is bound to at least one of the magnetostrictive particles and that binds to the target species, and alteration of the binding element via binding to the target species produces a resonance response of the magnetostrictive particles of the second detection chamber.

20. The magnetostrictive ligand sensor device according to claim 19, wherein the magnetostrictive particles of the first detection chamber and the magnetostrictive particles of the second detection chamber differ in mass and length.

21. The magnetostrictive ligand sensor device according to claim 19, further comprising a specimen archive chamber for collecting magnetostrictive particles and target species bound thereto in the liquid sample.

22. The magneto strictive ligand sensor device according to claim 21, further comprising a coil providing a magnetic field for holding and remotely manipulating the magnetostrictive particles in the specimen archive chamber.

23. The magnetostrictive ligand sensor device according to claim 21, further comprising a switch valve wherein the switch valve shunts the liquid sample of the specimen archive chamber through a modular filter to remove all particulates from the liquid sample and recycle the liquid back to the collection chamber.

* * * * *